United States Patent
Eastwood et al.

(10) Patent No.: US 7,625,889 B2
(45) Date of Patent: Dec. 1, 2009

(54) SUBSTITUTED BIS ARYL AND HETEROARYL COMPOUNDS AS SELECTIVE $5HT_{2A}$ ANTAGONISTS

(75) Inventors: Paul Robert Eastwood, Barcelona (ES); Hazel Hunt, Harlow (GB); David Mark Fink, Lebanon, NJ (US); Helen Katherine Smith, Harlow (GB); Richard Simon Todd, Harlow (GB)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 11/782,923

(22) Filed: Jul. 25, 2007

(65) Prior Publication Data

US 2007/0265309 A1   Nov. 15, 2007

Related U.S. Application Data

(63) Continuation of application No. PCT/US2006/004879, filed on Feb. 10, 2006.

(60) Provisional application No. 60/651,911, filed on Feb. 10, 2005.

(51) Int. Cl.
| | |
|---|---|
| A61K 31/551 | (2006.01) |
| A61K 31/496 | (2006.01) |
| C07D 263/58 | (2006.01) |
| C07D 277/68 | (2006.01) |
| C07D 413/14 | (2006.01) |
| C07D 417/14 | (2006.01) |
| C07D 231/56 | (2006.01) |
| C07D 235/06 | (2006.01) |
| C07D 249/18 | (2006.01) |
| C07D 401/14 | (2006.01) |
| C07D 498/04 | (2006.01) |

(52) U.S. Cl. ............... 514/218; 514/252.11; 514/253.1; 514/254.02; 540/575; 544/357; 544/364; 544/368; 544/105; 544/238; 544/285; 544/333; 544/362; 544/366; 544/370; 544/371; 544/373; 544/405; 546/113; 546/121; 546/194; 546/197; 546/199; 546/201; 546/271.7; 546/275.7; 546/277.4; 548/165; 548/171; 548/221; 548/257; 548/260; 548/306.4; 548/309.7; 548/361.1; 548/467; 548/469; 548/503

(58) Field of Classification Search ........................ None
See application file for complete search history.

(56) References Cited

U.S. PATENT DOCUMENTS 4,621,084 A * 11/1986 Takaya et al. ............ 514/224.2
6,348,485 B1 * 2/2002 Ohkawa et al. ............. 514/394

FOREIGN PATENT DOCUMENTS

| WO | WO 01/07435 | 2/2001 |
| WO | WO 01/53268 A2 | 7/2001 |
| WO | WO 2005/040131 | 5/2005 |
| WO | WO 2006/015259 | 2/2006 |

* cited by examiner

*Primary Examiner*—Emily Bernhardt
(74) *Attorney, Agent, or Firm*—Balaram Gupta

(57) ABSTRACT

The present invention relates to a series of substituted bis aryl and heteroaryl compounds of formula (I):

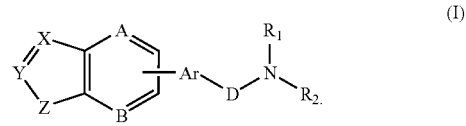

Wherein X, Y, Z, A, B, D, Ar, $R_1$ and $R_2$ are as defined herein. The compounds of this invention are selective $5HT_{2A}$ antagonists, and are therefore, useful in treating a variety of diseases including but not limited to a wide variety of sleep disorders as disclosed and claimed herein.

12 Claims, No Drawings

SUBSTITUTED BIS ARYL AND HETEROARYL COMPOUNDS AS SELECTIVE 5HT$_{2A}$ ANTAGONISTS

CROSS REFERENCE TO RELATED APPLICATIONS

This application is a continuation of International application No. PCT/US2006/004,879, filed Feb. 10, 2006, which is incorporated herein by reference in its entirety; which claims the benefit of U.S. Provisional Application No. 60/651,911, filed Feb. 10, 2005.

BACKGROUND OF THE INVENTION

1. Field of the Invention

The present invention relates to a series of substituted bis aryl and heteroaryl compounds as described herein. More specifically, the present invention relates to a series of dialkylamino, piperidinyl or piperazinyl substituted his aryl and heteroaryl derivatives. This invention also relates to methods of making these compounds. The compounds of this invention are selective serotonin, 5HT$_{2A}$, antagonists and are, therefore, useful as pharmaceutical agents, especially in the treatment and/or prevention of a variety of diseases including diseases associated with the central nervous system. More specifically, the compounds of this invention are useful in the treatment of a variety of sleep disorders.

2. Description of the Art

Chronic insomnia among adults in the United States has been estimated to be present in ten percent of the adult population, and the annual cost for its treatment is estimated at $10.9 billion. *JAMA* 1997; 278: 2170-2177 at 2170. Chronic insomniacs report elevated levels of stress, anxiety, depression and medical illnesses. The most common class of medications for treating insomnia are the benzodiazepines, but the adverse effect profile of benzodiazepines include daytime sedation, diminished motor coordination, and cognitive impairments. Furthermore, the National Institutes of Health Consensus conference on Sleeping Pills and Insomnia in 1984 have developed guidelines discouraging the use of such sedative-hypnotics beyond 4-6 weeks because of concerns raised over drug misuse, dependency, withdrawal and rebound insomnia. *JAMA* 1997; 278: 2170-2177 at 2170. Therefore, it is desirable to have a pharmacological agent for the treatment of insomnia which is more effective and/or has fewer side effects than those currently used.

The prevalence of obstructive sleep apnea is estimated to be approximately 1-10% in the adult population, but may be higher in elderly individuals; Diagnostic and Statistical Manual of Mental Disorders 4$^{th}$ ed., American Psychiatric Association, Washington D.C. (1994). Preliminary evidence suggests that having obstructive sleep apnea may contribute to increased susceptibility to cardiovascular complications such as hypertension, cardiac arrhythmias, stroke, and myocardial infarction. Excessive daytime sleepiness is also a major complication.

Currently, the therapies used to treat obstructive sleep apnea include weight loss for the obese patient, Nasal-continuous positive Airway Pressure (a facemask used at night which produces a positive pressure within the upper airway), pharyngeal surgery and the administration of a variety of pharmacologic agents which have not been proven to be entirely successful. *Chest* 109 (5):1346-1358 (May 1996) entitled Treatment of Obstructive Sleep Apnea, a Review, hereby incorporated by reference. These agents include Acetazolamide, Medroxyprogesterone, Opioid Antagonists, Nicotine, Angiotensin-Converting Enzyme Inhibitors and Psychotropic Agents (including those that prevent the reuptake of biogenic amines such as norepinephrine, dopamine and serotonin). Id. At 1353. Many of these pharmacological agents used also have a ventilatory depressant action (such as benzodiazepines) or other side effects such as urinary hesitancy and/or impotence in men (Protriptyline) so that a new agent with fewer side effects is needed for the treatment of obstructive sleep apnea. Even though serotonin is a sleep-inducing agent and may be a ventilatory stimulant (Id. At 1354), 5HT$_{2A}$ receptor antagonists have been found useful in treating obstructive sleep apnea. See also *Am. J. Respir Crit Care Med* (153) pp 776-786 (1996) where serotonin antagonists exacerbated sleep apnea produced in English bulldogs. But compare, *Journal of Physiology* (466) pp 367-382 (1993), where it is postulated that an excess of serotonin due to dysfunction of the serotonin biosynthesis mechanisms might set up conditions which favor obstructive apneas; *European Journal of Pharmacology* (259):71-74 (1994) further work on rat model with 5HT$_2$ antagonist.

EP 1 262 197 discloses a method of treating sleep disorders including sleep apnea by administering to a patient in need of such a treatment a 5HT$_{1A}$ antagonist or an alpha-2-adrenergic antagonist in combination with an antidepressant such as serotonin reuptake inhibitor (SRI). Such a combination exhibits an improvement in efficacy.

U.S. Pat. No. 6,143,792 discloses that a specific 5HT$_{2A}$ receptor antagonist is useful in the treatment of the sleep apnea syndrome. Similarly, U.S. Pat. No. 6,576,670 discloses that a specific 5HT$_{2A}$ and 5HT$_{2A/C}$ receptor antagonist is useful in the treatment of snoring and upper airway high resistance syndrome.

U.S. Pat. No. 6,277,864 discloses that a specific 5HT$_{2A}$ receptor antagonist is useful in the treatment of a variety of sleep disorders.

All of the references described herein are incorporated herein by reference in their entirety.

However, there is still a need for developing a compound that not only exhibits selective 5HT$_{2A}$ antagonistic activity but also exhibits improved safety properties with no or minimal side-effects.

Accordingly, it is an object of this invention to provide a series of dialkylamino, piperidinyl or piperazinyl substituted bis aryl and heteroaryl derivatives which are potent, selective serotonin, 5HT$_{2A}$, antagonists.

It is also an object of this invention to provide processes for the preparation of the dialkylamino, piperidinyl or piperazinyl substituted bis aryl and heteroaryl derivatives as disclosed herein.

Other objects and further scope of the applicability of the present invention will become apparent from the detailed description that follows.

SUMMARY OF THE INVENTION

Thus in accordance with this invention there is provided a compound, including enantiomers, stereoisomers, and tautomers of said compound and pharmaceutically acceptable salts, solvates or derivatives thereof, with said compound having the general structure shown in formula I:

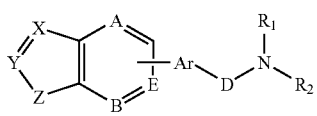

wherein:

denotes either a single or double bond between X and Y;
X is CR, CHR, CO, N, O or S;
Y is CR, CHR, CO, S(O)$_2$, N or NR;
Z is NR, CO—NR, S(O)$_2$—NR;
A, B and E are the same or different and independently from each other are CR or N;
D is either CH$_2$ or CO;
Ar is substituted or unsubstituted aryl or heteroaryl;
each R is independently chosen from hydrogen, halogen, CN, C(O)NR$_3$R$_4$, C$_{1-4}$alkyl, C$_{1-4}$alkoxy, C$_{1-4}$alkenyl, aryl, heteroaryl, arylC$_{1-4}$alkyl, heteroarylC$_{1-4}$alkyl, fluoroalkyl or fluoroalkoxy of the formula C$_n$H$_x$F$_y$ or OC$_n$H$_x$F$_y$ wherein n is an integer from 1 to 4, x is an integer from 0 to 8, y is an integer from 1 to 9 and sum of x and y is 2n+1; wherein
R$_3$ and R$_4$ are hydrogen or C$_{1-4}$alkyl; or
R$_3$ and R$_4$ taken together with the nitrogen atom to which they are attached form an unsubstituted or at least monosubstituted heterocycle; and
with the proviso that R is not benzimidazol-2-yl or phenyl;
R$_1$ and R$_2$ are the same or different and selected independently of each other from substituted or unsubstituted aryl, heteroaryl, aryloyl, heteroaryloyl, arylsulfonyl, heteroarylsulfonyl, arylC$_{1-4}$alkyl, heteroarylC$_{1-4}$alkyl, aminoC$_{1-4}$alkyl, C$_{1-4}$alkylaminoC$_{1-4}$alkyl, C$_{3-8}$cycloalkylaminoC$_{1-4}$alkyl, diC$_{3-8}$cycloalkylamino C$_{1-4}$alkyl, C$_{3-8}$cycloalkylC$_{1-4}$alkylaminoC$_{1-4}$alkyl, diC$_{1-4}$alkylaminoalkyl, heterocycle, heterocycle C$_{1-4}$alkyl, C$_{1-4}$alkylheterocycleC$_{1-4}$alkyl; or
R$_1$ and R$_2$ taken together with the nitrogen atom to which they are attached form an unsubstituted or at least monosubstituted heterocycle; and wherein
the substituents are selected from the group consisting of substituted or unsubstituted aryl, heteroaryl, arylC$_{1-4}$alkyl, heteroarylC$_{1-4}$alkyl, heterocycle, C$_{3-8}$cycloalkyl, C$_{1-4}$alkyl, C$_{1-4}$alkoxy, C$_{1-4}$alkenyl, fluoroalkyl or fluoroalkoxy of the formula C$_n$H$_x$F$_y$ or OC$_n$H$_x$F$_y$ wherein n is an integer from 1 to 4, x is an integer from 0 to 8, y is an integer from 1 to 9 and sum of x and y is 2n+1, —NO$_2$, —NH$_2$, —NH(C$_{1-4}$alkyl), —N(C$_{1-4}$alkyl)$_2$, —CN, —C(O)R$_5$, —NHC(O)(C$_{1-4}$alkyl), —SO$_2$Cl, —SO$_2$(C$_{1-4}$alkyl), halogen and hydroxy; wherein
R$_5$ is hydroxy, C$_{1-3}$alkoxy, —O-phenyl, —NH$_2$, —NH(C$_{1-3}$alkyl), —N(C$_{1-3}$alkyl)$_2$ or phenyl;
heteroaryl is a 5 to 10-membered, aromatic, mono- or bicyclic heterocycle containing one or more heteroatoms selected from the group consisting of N, O and S;
aryl is a 6 to 10-membered, aromatic mono- or bicyclic ring; and
heterocycle is a 3 to 10-membered, non-aromatic, mono- or bicyclic heterocycle containing one or more heteroatoms selected from the group consisting of N, O and S.

The compounds of this invention can be formulated into pharmaceutical compositions and are useful in treating a variety of disease states. Especially, the compounds of this invention are selective serotonin, 5HT$_{2A}$, antagonists and are, therefore, useful in the treatment of a wide variety of diseases associated with the central nervous system. More particularly, the compounds of this invention are useful in the treatment of a wide variety of sleep disorders including but not limited to insomnia and obstructive sleep apnea.

DETAILED DESCRIPTION OF THE INVENTION

The terms as used herein have the following meanings:

As used herein, the expression "C$_{1-6}$alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "C$_{1-4}$alkoxy", "C$_{1-4}$thioalkyl" "C$_{1-4}$alkoxyC$_{1-4}$alkyl", "hydroxyC$_{1-4}$alkyl", "C$_{1-4}$alkylcarbonyl", "C$_{1-4}$alkoxycarbonylC$_{1-4}$alkyl", "C$_{1-4}$alkoxycarbonyl", "aminoC$_{1-4}$alkyl", "C$_{1-4}$alkylamino", "C$_{1-4}$alkylcarbamoylC$_{1-6}$alkyl", "C$_{1-4}$dialkylcarbamoylC$_{1-4}$alkyl" "mono- or di-C$_{1-4}$alkylaminoC$_{1-4}$alkyl", "aminoC$_{1-4}$alkylcarbonyl" "diphenylC$_{1-4}$alkyl", "phenylC$_{1-4}$alkyl", "phenylcarboyl C$_{1-4}$alkyl" and "phenoxyC$_{1-4}$alkyl" are to be construed accordingly.

As used herein, the expression "C$_{2-6}$alkenyl" includes ethenyl and straight-chained or branched propenyl, butenyl, pentenyl and hexenyl groups. Similarly, the expression "C$_{2-6}$alkynyl" includes ethynyl and propynyl, and straight-chained or branched butynyl, pentynyl and hexynyl groups.

As used herein the expression "C$_{1-4}$acyl" shall have the same meaning as "C$_{1-6}$alkanoyl", which can also be represented structurally as "R—CO—," where R is a C$_{1-3}$alkyl as defined herein. Additionally, "C$_{1-3}$alkylcarbonyl" shall mean same as C$_{1-4}$acyl. Specifically, "C$_{1-4}$acyl" shall mean formyl, acetyl or ethanoyl, propanoyl, n-butanoyl, etc. Derived expressions such as "C$_{1-4}$acyloxy" and "C$_{1-4}$acyloxyalkyl" are to be construed accordingly.

As used herein, the expression "C$_{1-6}$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "C$_{1-6}$ perfluoroalkoxy", is to be construed accordingly.

As used herein, the expression "aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, "arylsulfonyl," is to be construed accordingly. Specific examples of arylsulfonyl include benzenesulfonyl, p-toluenesulfonyl, and the like.

As used herein, the expression "C$_{6-12}$arylC$_{1-4}$alkyl" means that the C$_{6-12}$aryl as defined herein is further attached to C$_{1-4}$alkyl as defined herein. Representative examples include benzyl, phenylethyl, 2-phenylpropyl, 1-naphthylmethyl, 2-naphthylmethyl and the like.

As used herein, the expression "heteroaryl" includes all of the known heteroatom containing aromatic radicals. Representative 5-membered heteroaryl radicals include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, benzimidazolyl, indazolyl, pyridofuranyl, pyridothienyl, and the like radicals.

Similarly, the expression "heteroaryl$C_{1-4}$alkyl" means that the heteroaryl as defined herein is further attached to $C_{1-4}$alkyl as defined herein. Representative examples include furanylmethyl, thienylethyl, 2-(thiophenyl)propyl, pyrrolylmethyl, isopyrrolylethyl, pyrazolylmethyl, imidazolylmethyl, and the like.

As used herein, the expression "heterocycle" includes all of the known reduced heteroatom containing cyclic radicals. Representative 5-membered heterocycle radicals include tetrahydrofuranyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, thiomorpholinyl, and the like. Various other heterocycle radicals include, without limitation, aziridinyl, azepanyl, diazepanyl, diazabicyclo[2.2.1]hept-2-yl, and triazocanyl, and the like. Derived expression "heterocycle$C_{1-4}$alkyl" is to be construed accordingly. Specific examples of heterocycle$C_{1-4}$alkyl include without any limitation the following: N-pyrrolidinylmethyl, N-pyrrolidinylethyl, pyrrolidinyl-2-methyl, 2-pyrrolidinyl-2-ethyl, and the like. Similarly, the expression "$C_{1-4}$alkylheterocycle $C_{1-4}$alkyl" should be construed accordingly. Representative examples include without any limitation the following: N-ethylpyrrolidinyl-N'-methyl, 2-ethyl-N-pyrrolidinylethyl, N-ethyl-pyrrolidinyl-2-methyl, 2-pyrrolidinylethyl-2-ethyl, and the like.

"Halogen" or "halo" means chloro, fluoro, bromo, and iodo.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

The term "solvate" as used herein means that an aggregate that consists of a solute ion or molecule with one or more solvent molecules. Similarly, a "hydrate" means that an aggregate that consists of a solute ion or molecule with one or more water molecules.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$alkyl, $C_{2-6}$alkenyl, $C_{1-6}$ perfluoroalkyl, phenyl, hydroxy, —$CO_2H$, an ester, an amide, $C_1$-$C_6$alkoxy, $C_1$-$C_6$thioalkyl, $C_1$-$C_6$ perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the compound which is effective in treating the named disease, disorder or condition.

The term "treating" refers to:
(i) preventing a disease, disorder or condition from occurring in a patient that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Thus, in accordance with the practice of this invention there is provided a compound including enantiomers, stereoisomers, and tautomers of said compound and pharmaceutically acceptable salts, solvates or derivatives thereof, with said compound having the general structure shown in formula I:

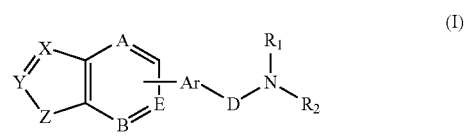

(I)

wherein:

$$X=Y$$

denotes either a single or double bond between X and Y;
X is CR, CHR, CO, N, O or S;
Y is CR, CHR, CO, S(O)$_2$, N or NR;
Z is NR, CO—NR, S(O)$_2$—NR;
A, B and E are the same or different and independently from each other are CR or N;
D is either CH$_2$ or CO;
Ar is substituted or unsubstituted aryl or heteroaryl;
each R is independently chosen from hydrogen, halogen, CN, C(O)NR$_3$R$_4$, C$_{1-4}$alkyl, C$_{1-4}$alkoxy, C$_{1-4}$alkenyl, aryl, heteroaryl, arylC$_{1-4}$alkyl, heteroarylC$_{1-4}$alkyl, fluoroalkyl or fluoroalkoxy of the formula C$_n$H$_x$F$_y$ or OC$_n$H$_x$F$_y$, wherein n is an integer from 1 to 4, x is an integer from 0 to 8, y is an integer from 1 to 9 and sum of x and y is 2n+1; wherein
R$_3$ and R$_4$ are hydrogen or C$_{1-4}$alkyl; or
R$_3$ and R$_4$ taken together with the nitrogen atom to which they are attached form an unsubstituted or at least monosubstituted heterocycle; and
with the proviso that R is not benzimidazol-2-yl or phenyl;
R$_1$ and R$_2$ are the same or different and selected independently of each other from substituted or unsubstituted aryl, heteroaryl, aryloyl, heteroaryloyl, arylsulfonyl, heteroarylsulfonyl, arylC$_{1-4}$alkyl, heteroarylC$_{1-4}$alkyl, aminoC$_{1-4}$alkyl, C$_{1-4}$alkylaminoC$_{1-4}$alkyl, C$_{3-8}$cycloalkylaminoC$_{1-4}$alkyl, diC$_{3-8}$cycloalkylamino C$_{1-4}$alkyl, C$_{3-8}$cycloalkylC$_{1-4}$alkylaminoC$_{1-4}$alkyl, diC$_{1-4}$alkylaminoalkyl, heterocycle, heterocycle C$_{1-4}$alkyl, C$_{1-4}$alkylheterocycleC$_{1-4}$alkyl; or
R$_1$ and R$_2$ taken together with the nitrogen atom to which they are attached form an unsubstituted or at least monosubstituted heterocycle; and wherein
the substituents are selected from the group consisting of substituted or unsubstituted aryl, heteroaryl, arylC$_{1-4}$alkyl, heteroarylC$_{1-4}$alkyl, heterocycle, C$_{3-8}$cycloalkyl, C$_{1-4}$alkyl, C$_{1-4}$alkoxy, C$_{1-4}$alkenyl, fluoroalkyl or fluoroalkoxy of the formula C$_n$H$_x$F$_y$ or OC$_n$H$_x$F$_y$ wherein n is an integer from 1 to 4, x is an integer from 0 to 8, y is an integer from 1 to 9 and sum of x and y is 2n+1, —NO$_2$, —NH$_2$, —NH(C$_{1-4}$alkyl), —N(C$_{1-4}$alkyl)$_2$, —CN, —C(O)R$_5$, —NHC(O)(C$_{1-4}$alkyl), —SO$_2$Cl, —SO$_2$(C$_{1-4}$alkyl), halogen and hydroxy; wherein
R$_5$ is hydroxy, C$_{1-3}$alkoxy, —O-phenyl, —NH$_2$, —NH(C$_{1-3}$alkyl), —N(C$_{1-3}$alkyl)$_2$ or phenyl;
heteroaryl is a 5 to 10-membered, aromatic, mono- or bicyclic heterocycle containing one or more heteroatoms selected from the group consisting of N, O and S;
aryl is a 6 to 10-membered, aromatic mono- or bicyclic ring; and
heterocycle is a 3 to 10-membered, non-aromatic, mono- or bicyclic heterocycle containing one or more heteroatoms selected from the group consisting of N, O and S.

In one aspect of this invention, the compounds of formula (I) having the following substituents are preferred:
D is CH$_2$;
Ar is substituted or unsubstituted phenyl, pyridinyl, pyrazinyl, furanyl or thiophenyl; wherein the substituents are selected from the group consisting of fluorine, chlorine, C$_{1-4}$alkyl, C$_{1-4}$alkoxy and —CF$_3$;
each R is independently chosen from hydrogen, CN or C$_{1-4}$alkyl;
R$_1$ and R$_2$ are the same or different and selected independently of each other from substituted or unsubstituted benzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, phenylC$_{0-4}$alkyl, thiophenyl C$_{1-4}$alkyl, aza-bicyclo[2.2.2]octylC$_{0-4}$alkyl, aza-bicyclo[3.2.1]octylC$_{0-4}$alkyl, piperidinylC$_{0-4}$alkyl, pyrrolidinylC$_{0-4}$alkyl, C$_{1-4}$alkylaminoC$_{1-4}$alkyl and diC$_{1-4}$alkylaminoC$_{1-4}$alkyl; wherein the substituted moieties may be substituted with one or more substituents selected from the group consisting of fluorine, chlorine, C$_{1-4}$alkyl, C$_{3-8}$cycloalkyl, C$_{1-4}$alkoxy, OCF$_3$ and CF$_3$; or
R$_1$ and R$_2$ taken together with the nitrogen atom to which they are attached form an unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and C$_{1-4}$alkyl.

In a further aspect of this invention, the compounds of formula (I) with the following substituents are preferred:

$$X=Y$$

denotes a double bond between X and Y;
X is CR;
Y is CR;
Z is NR;
A, B and E are the same or different and independently from each other are CH or N;
Ar is phenyl, fluorophenyl, chlorophenyl, pyridinyl, pyrazinyl, furanyl or thiophenyl;
each R is independently chosen from hydrogen, CN, methyl, ethyl, methoxy, fluorine, CF$_3$ or OCF$_3$;
R$_1$ and R$_2$ are the same or different and selected independently of each other from benzyl, fluorobenzyl, fluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, aza-bicyclo[2.2.2] octyl, aza-bicyclo[2.2.2]octylmethyl, N-methyl-piperidinyl, pyrrolidinylmethyl, pyrrolidinylethyl, pyrrolidinylpropyl and dimethylaminoethyl;
or
R$_1$ and R$_2$ taken together with the nitrogen atom to which they are attached form an unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Examples of compounds encompassed within the above noted embodiment without any limitations include the following:
N-benzyl-N-[3-(1H-indol-5-yl)-benzyl]-N',N'-dimethyl-ethane-1,2-diamine;
4-fluoro-N-[2-fluoro-5-(1H-indol-5-yl)-benzyl]-N-(2-pyrrolidin-1-yl-ethyl)-benzamide;

N-(2-dimethylamino-ethyl)-4-fluoro-N-[2-fluoro-5-(2-methyl-1H-indol-5-yl)-benzyl]-benzamide;
N-(2-dimethylamino-ethyl)-4-fluoro-N-[2-fluoro-5-(1H-indol-5-yl)-benzyl]-benzamide;
4-fluoro-N-[3-(1H-indol-5-yl)-benzyl]-N-(1-methyl-piperidin-4-yl)-benzamide;
thiophene-2-carboxylic acid [3-(1H-indol-5-yl)-benzyl]-(1-methyl-piperidin-4-yl)-amide;
thiophene-2-carboxylic acid [2-fluoro-5-(1H-indol-5-yl)-benzyl]-(1-methyl-piperidin-4-yl)-amide;
thiophene-2-carboxylic acid (2-dimethylamino-ethyl)-[2-fluoro-5-(1H-indol-5-yl)-benzyl]-amide;
4-fluoro-N-[2-fluoro-5-(1H-indol-5-yl)-benzyl]-N-(1-methyl-piperidin-4-yl)-benzamide;
N-(1-aza-bicyclo[2.2.2]oct-4-ylmethyl)-4-fluoro-N-[2-fluoro-5-(1H-indol-5-yl)-benzyl]-benzamide trifluoro-acetate;
4-fluoro-N-[5-(1H-indol-5-yl)-pyridin-3-ylmethyl]-N-(2-pyrrolidin-1-yl-ethyl)-benzamide;
4-fluoro-N-[4-fluoro-3-(1H-indol-5-yl)-benzyl]-N-(1-methyl-piperidin-4-yl)-benzamide;
4-fluoro-N-[4-(1H-indol-5-yl)-thiophen-2-ylmethyl]-N-(2-pyrrolidin-1-yl-ethyl)-benzamide acetate;
(4-fluoro-benzyl)-[2-fluoro-5-(1H-indol-5-yl)-benzyl]-(1-methyl-piperidin-4-yl)-amine;
N-(4-fluoro-benzyl)-N-[2-fluoro-5-(1H-indol-5-yl)-benzyl]-N',N'-dimethyl-ethane-1,2-diamine;
(1-aza-bicyclo[2.2.2]oct-4-ylmethyl)-(4-fluoro-benzyl)-[2-fluoro-5-(1H-indol-5-yl)-benzyl]-amine acetate;
N-(2-dimethylamino-ethyl)-4-fluoro-N-[5-(1H-indol-5-yl)-pyridin-3-ylmethyl]-benzamide trifluoroacetate;
4-fluoro-N-[5-(1H-indol-5-yl)-thiophen-2-ylmethyl]-N-(2-pyrrolidin-1-yl-ethyl)-benzamide;
4-fluoro-N-[4-(1H-indol-5-yl)-furan-2-ylmethyl]-N-(1-methyl-piperidin-4-yl)-benzamide;
N-(1-aza-bicyclo[2.2.2]oct-3R-yl)-4-fluoro-N-[2-fluoro-5-(1H-indol-6-yl)-benzyl]-benzamide;
pyrimidine-4-carboxylic acid [2-fluoro-5-(1H-indol-5-yl)-benzyl]-(1-methyl-piperidin-4-yl)-amide;
pyrimidine-2-carboxylic acid [2-fluoro-5-(1H-indol-5-yl)-benzyl]-(1-methyl-piperidin-4-yl)-amide;
pyridazine-3-carboxylic acid [2-fluoro-5-(1H-indol-5-yl)-benzyl]-(1-methyl-piperidin-4-yl)-amide;
pyridazine-4-carboxylic acid [2-fluoro-5-(1H-indol-5-yl)-benzyl]-(1-methyl-piperidin-4-yl)-amide;
2,3-dihydro-benzo[1,4]dioxine-6-carboxylic acid [2-fluoro-5-(1H-indol-5-yl)-benzyl]-(1-methyl-piperidin-4-yl)-amide;
N-[2-fluoro-5-(1H-indol-5-yl)-benzyl]-4-isopropoxy-N-(1-methyl-piperidin-4-yl)-benzamide;
N-[2-fluoro-5-(1H-indol-5-yl)-benzyl]-3-isopropoxy-N-(1-methyl-piperidin-4-yl)-benzamide;
N-[2-fluoro-5-(1H-indol-5-yl)-benzyl]-N-(1-methyl-piperidin-4-yl)-4-trifluoromethoxy-benzamide;
4-chloro-N-[2-fluoro-5-(1H-indol-5-yl)-benzyl]-N-(1-methyl-piperidin-4-yl)-benzamide;
benzo[1,3]dioxole-5-carboxylic acid [2-fluoro-5-(1H-indol-5-yl)-benzyl]-(1-methyl-piperidin-4-yl)-amide;
N-[2-fluoro-5-(1H-indol-5-yl)-benzyl]-N-(1-methyl-piperidin-4-yl)-4-trifluoromethyl-benzamide;
4-fluoro-N-[2-fluoro-5-(1H-indol-5-yl)-benzyl]-N-(1-methyl-piperidin-4-yl)-3-trifluoromethyl-benzamide;
N-[2-fluoro-5-(1H-indol-5-yl)-benzyl]-N-(1-methyl-piperidin-4-yl)-isonicotinamide;
N-[3-(1H-indol-5-yl)-benzyl]-N-(1-methyl-piperidin-4-yl)-4-trifluoromethyl-benzamide;
4-fluoro-N-[4-fluoro-3-(1H-indol-5-yl)-benzyl]-N-(2-pyrrolidin-1-yl-ethyl)-benzamide;
N-[2-fluoro-5-(1H-indol-5-yl)-benzyl]-N-(2-pyrrolidin-1-yl-ethyl)-4-trifluoromethyl-benzamide;
4-fluoro-N-[3-fluoro-5-(1H-indol-5-yl)-benzyl]-N-(2-pyrrolidin-1-yl-ethyl)-benzamide;
N-[3-(1H-indol-5-yl)-benzyl]-N-(2-pyrrolidin-1-yl-ethyl)-4-trifluoromethyl-benzamide;
N-[3-(1H-indol-5-yl)-benzyl]-N-(2-pyrrolidin-1-yl-ethyl)-isonicotinamide;
N-[4-fluoro-3-(1H-indol-5-yl)-benzyl]-N-(2-pyrrolidin-1-yl-ethyl)-4-trifluoromethyl-benzamide;
N-[3-(1H-indol-5-yl)-benzyl]-N-(3-pyrrolidin-1-yl-propyl)-isonicotinamide;
N-[4-fluoro-3-(1H-indol-5-yl)-benzyl]-N-(3-pyrrolidin-1-yl-propyl)-isonicotinamide;
pyridine-2-carboxylic acid [3-(1H-indol-5-yl)-benzyl]-(3-pyrrolidin-1-yl-propyl)-amide;
N-[3-(1H-indol-5-yl)-benzyl]-N-(3-pyrrolidin-1-yl-propyl)-4-trifluoromethyl-benzamide;
pyridine-2-carboxylic acid [4-fluoro-3-(1H-indol-5-yl)-benzyl]-(3-pyrrolidin-1-yl-propyl)-amide;
pyridine-2-carboxylic acid [4-(1H-indol-5-yl)-thiophen-2-ylmethyl]-(3-pyrrolidin-1-yl-propyl)-amide;
N-[4-(1H-indol-5-yl)-thiophen-2-ylmethyl]-N-(3-pyrrolidin-1-yl-propyl)-4-trifluoromethyl-benzamide;
N-[4-(1H-indol-5-yl)-thiophen-2-ylmethyl]-N-(2-pyrrolidin-1-yl-ethyl)-isonicotinamide;
pyridine-2-carboxylic acid [4-(1H-indol-5-yl)-thiophen-2-ylmethyl]-(2-pyrrolidin-1-yl-ethyl)-amide;
N-[4-(1H-indol-5-yl)-thiophen-2-ylmethyl]-N-(2-pyrrolidin-1-yl-ethyl)-4-trifluoromethyl-benzamide;
pyridine-2-carboxylic acid [4-(1H-indol-5-yl)-furan-2-ylmethyl]-(3-pyrrolidin-1-yl-propyl)-amide;
N-[4-(1H-indol-5-yl)-furan-2-ylmethyl]-N-(3-pyrrolidin-1-yl-propyl)-4-trifluoromethyl-benzamide;
N-[4-(1H-indol-5-yl)-furan-2-ylmethyl]-N-(2-pyrrolidin-1-yl-ethyl)-isonicotinamide;
pyridine-2-carboxylic acid [4-(1H-indol-5-yl)-furan-2-ylmethyl]-(2-pyrrolidin-1-yl-ethyl)-amide;
N-[4-(1H-indol-5-yl)-furan-2-ylmethyl]-N-(2-pyrrolidin-1-yl-ethyl)-4-trifluoromethyl-benzamide;
N-[4-(1H-indol-5-yl)-thiophen-2-ylmethyl]-N-(3-pyrrolidin-1-yl-propyl)-isonicotinamide;
N-[4-(1H-indol-5-yl)-furan-2-ylmethyl]-N-(3-pyrrolidin-1-yl-propyl)-isonicotinamide;
N-[2-chloro-5-(1H-indol-5-yl)-benzyl]-N-(1-methyl-piperidin-4-yl)-isonicotinamide;
pyridine-2-carboxylic acid [2-fluoro-5-(1H-indol-5-yl)-benzyl]-(1-methyl-piperidin-4-yl)-amide;
N-[2-fluoro-5-(1H-indol-5-yl)-benzyl]-N-(1-methyl-piperidin-4-yl)-nicotinamide;
N-[2-fluoro-5-(1H-indol-5-yl)-benzyl]-N-(1-methyl-piperidin-4-yl)-3-trifluoromethoxy-benzamide;
N-[2-fluoro-5-(1H-indol-5-yl)-benzyl]-N-(2-pyrrolidin-1-yl-ethyl)-isonicotinamide;
N-[4-fluoro-3-(1H-indol-5-yl)-benzyl]-N-(2-pyrrolidin-1-yl-ethyl)-isonicotinamide;
N-[4-fluoro-3-(1H-indol-5-yl)-benzyl]-N-(2-pyrrolidin-1-yl-ethyl)-4-trifluoromethoxy-benzamide acetate;
N-[3-(1H-indol-5-yl)-benzyl]-N-(1-methyl-piperidin-4-yl)-isonicotinamide;
pyrazine-2-carboxylic acid [2-fluoro-5-(1H-indol-5-yl)-benzyl]-(1-methyl-piperidin-4-yl)-amide;
5-[4-fluoro-3-(4-methyl-2-pyridin-3-yl-piperazin-1-ylmethyl)-phenyl]-1H-indole acetate;

5-{4-fluoro-3-[4-methyl-2-(4-trifluoromethyl-phenyl)-piperazin-1-ylmethyl]-phenyl}-1H-indole;
5-[4-fluoro-3-(4-methyl-2-pyridin-2-yl-piperazin-1-ylmethyl)-phenyl]-1H-indole acetate;
5-{5-[2S-(4-fluoro-phenyl)-4-methyl-piperazin-1-ylmethyl]-pyridin-3-yl}-1H-indole acetate;
5-{4-fluoro-3-[2S-(4-fluoro-phenyl)-4-methyl-piperazin-1-ylmethyl]-phenyl}-1H-indole;
5-[4-fluoro-3-(2-furan-2-yl-4-methyl-piperazin-1-ylmethyl)-phenyl]-1H-indole;
5-{5-[2S-(4-fluoro-phenyl)-4-methyl-piperazin-1-ylmethyl]-furan-3-yl}-1H-indole trifluoro-acetate;
5-{5-[2S-(4-fluoro-phenyl)-piperazin-1-ylmethyl]-pyridin-3-yl}-1H-indole acetate;
5-{5-[2S-(4-fluoro-phenyl)-piperazin-1-ylmethyl]-furan-3-yl}-1H-indole;
5-[3-(4-methyl-piperazin-1-ylmethyl)-phenyl]-1H-indole;
5-[4-fluoro-3-(4-methyl-2-pyridin-4-yl-piperazin-1-ylmethyl)-phenyl]-1H-indole;
5-{3-[2S-(4-fluoro-phenyl)-4-methyl-piperazin-1-ylmethyl]-phenyl}-1H-indole;
5-{6-[2S-(4-fluoro-phenyl)-4-methyl-piperazin-1-ylmethyl]-pyrazin-2-yl}-1H-indole acetate;
5-{4-fluoro-3-[2S-(4-fluoro-phenyl)-piperazin-1-ylmethyl]-phenyl}-1H-indole acetate;
5-{4-fluoro-3-[2S-(4-fluoro-phenyl)-4-methyl-piperazin-1-ylmethyl]-phenyl}-1H-indole-3-carbonitrile;
5-[3-(4-methyl-[1,4]diazepan-1-ylmethyl)-phenyl]-1H-indole;
5-{4-fluoro-3-[2S-(4-fluoro-phenyl)-4-methyl-piperazin-1-ylmethyl]-phenyl}-3-methyl-1H-indole;
N-[5-(3-cyano-1H-indol-5-yl)-2-fluoro-benzyl]-N-(2-dimethylamino-ethyl)-4-fluoro-benzamide;
5-{4-fluoro-3-[2S-(4-fluoro-phenyl)-piperazin-1-ylmethyl]-phenyl}-1H-indole-3-carbonitrile;
5-(3-{[(2-dimethylamino-ethyl)-(4-fluoro-benzyl)-amino]-methyl}-4-fluoro-phenyl)-1H-indole-3-carbonitrile trifluoro-acetate;
4-fluoro-N-[2-fluoro-5-(1H-pyrrolo[3,2-b]pyridin-5-yl)-benzyl]-N-(2-pyrrolidin-1-yl-ethyl)-benzamide;
5-{4-fluoro-3-[2-(4-fluoro-phenyl)-4-methyl-piperazin-1-ylmethyl]-phenyl}-1H-pyrrolo[3,2-b]pyridine; and
4-fluoro-N-[2-fluoro-5-(1H-pyrrolo[2,3-c]pyridin-5-yl)-benzyl]-N-(2-pyrrolidin-1-yl-ethyl)-benzamide;
or a pharmaceutically acceptable salt thereof or an optical or stereoisomer thereof.

In yet another embodiment of this invention, the compounds of formula (I) having the following substituents are also preferred:

denotes a double bond between X and Y;
X is CR;
Y is N;
Z is NR;
A, B and E are CH;
Ar is phenyl, fluorophenyl, chlorophenyl, pyridinyl, pyrazinyl, furanyl or thiophenyl;
each R is independently chosen from hydrogen, methyl, ethyl, methoxy, fluorine, $CF_3$ or $OCF_3$;
$R_1$ and $R_2$ are the same or different and selected independently of each other from benzyl, fluorobenzyl, fluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, N-methyl-aza-bicyclo[2.2.2]octyl, aza-bicyclo[2.2.2]octyl, aza-bicyclo[2.2.2]octylmethyl, N-methyl-piperidinyl, piperidinyl, N-methyl-pyrrolidinyl, pyrrolidinylmethyl, pyrrolidinylethyl, pyrrolidinylpropyl, methylaminoethyl, and dimethylaminoethyl;
or
$R_1$ and $R_2$ taken together with the nitrogen atom to which they are attached form an unsubstituted or at least mono-substituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Examples of compounds within the scope of this embodiment without any limitations may be enumerated as follows:
N-benzyl-N-[3-(1H-indazol-5-yl)-benzyl]-N',N'-dimethyl-ethane-1,2-diamine hydrochloride;
N-(4-fluoro-benzyl)-N-[5-(1H-indazol-5-yl)-pyridin-3-ylmethyl]-N',N'-dimethyl-ethane-1,2-diamine acetate;
(4-fluoro-benzyl)-[2-fluoro-5-(1H-indazol-5-yl)-benzyl]-pyrrolidin-2S-ylmethyl-amine;
(4-fluoro-benzyl)-[2-fluoro-5-(1H-indazol-5-yl)-benzyl]-piperidin-4-yl-amine;
N-(4-fluoro-benzyl)-N-[2-fluoro-5-(1H-indazol-5-yl)-benzyl]-N'-methyl-ethane-1,2-diamine;
(4-fluoro-benzyl)-[2-fluoro-5-(1H-indazol-5-yl)-benzyl]-(1-methyl-piperidin-4-yl)-amine;
(4-fluoro-benzyl)-[4-(1H-indazol-5-yl)-furan-2-ylmethyl]-(1-methyl-piperidin-4-yl)-amine;
4-fluoro-N-[2-fluoro-5-(1H-indazol-5-yl)-benzyl]-N-(2-pyrrolidin-1-yl-ethyl)-benzamide;
4-fluoro-N-[2-fluoro-5-(1H-indazol-5-yl)-benzyl]-N-(exo-8-methyl-8-aza-bicyclo[3.2.1]oct-3-yl)-benzamide;
4-fluoro-N-[2-fluoro-5-(1H-indazol-5-yl)-benzyl]-N-(endo-8-methyl-8-aza-bicyclo[3.2.1]oct-3-yl)-benzamide;
4-fluoro-N-[2-fluoro-5-(1H-indazol-5-yl)-benzyl]-N-(1-methyl-piperidin-3-yl)-benzamide;
4-fluoro-N-[2-fluoro-5-(1H-indazol-5-yl)-benzyl]-N-(1-methyl-piperidin-3S-yl)-benzamide trifluoro-acetate;
4-fluoro-N-[2-fluoro-5-(1H-indazol-5-yl)-benzyl]-N-(1-methyl-pyrrolidin-3R-yl)-benzamide trifluoro-acetate;
4-fluoro-N-[2-fluoro-5-(1H-indazol-5-yl)-benzyl]-N-(1-methyl-pyrrolidin-3S-yl)-benzamide trifluoro-acetate;
4-fluoro-N-[2-fluoro-5-(1H-indazol-5-yl)-benzyl]-N-(3-pyrrolidin-1-yl-propyl)-benzamide;
4-fluoro-N-[2-fluoro-5-(1H-indazol-5-yl)-benzyl]-N-(1-methyl-piperidin-4-yl)-benzamide;
N-(1-aza-bicyclo[2.2.2]oct-3R-yl)-4-fluoro-N-[2-fluoro-5-(1H-indazol-5-yl)-benzyl]-benzamide;
chiral N-[2-fluoro-5-(1H-indazol-5-yl)-benzyl]-N-(1-methyl-pyrrolidin-3R-yl)-4-trifluoromethyl-benzamide;
4-fluoro-N-[4-(1H-indazol-5-yl)-furan-2-ylmethyl]-N-(1-methyl-piperidin-4-yl)-benzamide;
5-{4-fluoro-3-[2-(4-fluoro-phenyl)-piperazin-1-ylmethyl]-phenyl}-1H-indazole;
5-[4-fluoro-3-(2S-thiophen-2-yl-piperazin-1-ylmethyl)-phenyl]-1H-indazole acetate;
5-[4-fluoro-3-(2-thiophen-2-yl-piperazin-1-ylmethyl)-phenyl]-1H-indazole;
chiral 5-[4-fluoro-3-(2-thiophen-2-yl-piperazin-1-ylmethyl)-phenyl]-1H-indazole acetate;

5-{4-fluoro-3-[2S-(4-fluoro-phenyl)-4-methyl-piperazin-1-ylmethyl]-phenyl}-1H-indazole;

5-{5-[2S-(4-fluoro-phenyl)-4-methyl-piperazin-1-ylmethyl]-pyridin-3-yl}-1H-indazole;

5-{5-[2S-(4-fluoro-phenyl)-piperazin-1-ylmethyl]-pyridin-3-yl}-1H-indazole;

5-{5-[2S-(4-fluoro-phenyl)-piperazin-1-ylmethyl]-furan-3-yl}-1H-indazole;

5-[4-fluoro-3-(4-methyl-2R-thiophen-2-yl-piperazin-1-ylmethyl)-phenyl]-1H-indazole acetate;

5-[4-fluoro-3-(4-methyl-2S-thiophen-2-yl-piperazin-1-ylmethyl)-phenyl]-1H-indazole acetate; and 5-{5-[2S-(4-fluoro-phenyl)-4-methyl-piperazin-1-ylmethyl]-furan-3-yl}-1H-indazole;

or a pharmaceutically acceptable salt thereof or an optical or stereoisomer thereof.

In another embodiment of this invention, compounds of formula (I) having the following substituents are preferred:

$$X=Y$$

denotes a double bond between X and Y;

X is N;
Y is CR;
Z is NR;
A, B and E are CH;
Ar is phenyl, fluorophenyl, chlorophenyl, pyridinyl, pyrazinyl, furanyl or thiophenyl;
each R is independently chosen from hydrogen, methyl, ethyl, methoxy, $CF_3$ or $OCF_3$;
$R_1$ and $R_2$ are the same or different and selected independently of each other from benzyl, fluorobenzyl, fluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, N-methyl-aza-bicyclo[2.2.2]octyl, aza-bicyclo[2.2.2]octyl, aza-bicyclo[2.2.2]octylmethyl, N-methyl-piperidinyl, piperidinyl, N-methyl-pyrrolidinyl, pyrrolidinylmethyl, pyrrolidinylethyl, pyrrolidinylpropyl, methylaminoethyl, dimethylaminoethyl and dimethylaminopropyl;
or
$R_1$ and $R_2$ taken together with the nitrogen atom to which they are attached form an unsubstituted or at least mono-substituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Specific examples of compounds within the scope of this embodiment without any limitations are listed as follows:

N-[3-(1H-benzoimidazol-5-yl)-benzyl]-N-benzyl-N',N'-dimethyl-ethane-1,2-diamine hydrochloride; and N-[3-(1H-benzoimidazol-5-yl)-benzyl]-N-benzyl-N',N'-dimethyl-propane-1,3-diamine hydrochloride;

or a pharmaceutically acceptable salt thereof or an optical or stereoisomer thereof.

In another embodiment of this invention the compound of formula (I) is having the following substituents:

$$X=Y$$

denotes a double bond between X and Y;

X is N;
Y is N;
Z is NR;
A, B and E are CH;
Ar is phenyl, fluorophenyl, chlorophenyl, pyridinyl, pyrazinyl, furanyl or thiophenyl;
R is hydrogen, methyl or ethyl;
$R_1$ and $R_2$ are the same or different and selected independently of each other from benzyl, fluorobenzyl, fluorobenzoyl, difluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, thiophenylmethyl, N-methyl-aza-bicyclo[2.2.2]octyl, aza-bicyclo[2.2.2]octyl, aza-bicyclo[2.2.2]octylmethyl, N-methyl-piperidinyl, N-isopropyl-piperidinyl, N-cyclopropyl-piperidinyl, piperidinyl, N-methyl-pyrrolidinyl, N-ethyl-pyrrolidinylmethyl, pyrrolidinylmethyl, pyrrolidinylethyl, pyrrolidinylpropyl, methylaminoethyl, dimethylaminoethyl and dimethylaminopropyl;
or
$R_1$ and $R_2$ taken together with the nitrogen atom to which they are attached form an unsubstituted or at least mono-substituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Examples of compounds of formula (I) falling within the scope of the above noted embodiment include without any limitations the following:

N-[3-(1H-benzotriazol-5-yl)-benzyl]-N-benzyl-N',N'-dimethyl-propane-1,3-diamine;

[5-(1H-benzothiazol-5-yl)-2-fluoro-benzyl]-(4-fluoro-benzyl)-pyrrolidin-2R-ylmethyl-amine trihydrochloride;

[5-(1H-benzotriazol-5-yl)-2-fluoro-benzyl]-piperidin-4-yl-thiophen-2-ylmethyl-amine;

[5-(1H-benzotriazol-5-yl)-2-fluoro-benzyl]-(4-fluoro-benzyl)-piperidin-4-yl-amine;

N-[5-(1H-benzotriazol-5-yl)-2-fluoro-benzyl]-N-(4-fluoro-benzyl)-N'-methyl-ethane-1,2-diamine;

[5-(1H-benzotriazol-5-yl)-2-fluoro-benzyl]-(1-ethyl-pyrrolidin-2S-ylmethyl)-(4-fluoro-benzyl)-amine hydrochloride;

[5-(1H-benzotriazol-5-yl)-2-fluoro-benzyl]-(4-fluoro-benzyl)-(1-methyl-piperidin-4-yl)-amine hydrochloride;

N-[3-(1H-benzotriazol-5-yl)-benzyl]-N-benzyl-N',N'-dimethyl-ethane-1,2-diamine hydrochloride;

N-[5-(1H-benzotriazol-5-yl)-2-fluoro-benzyl]-N-(1-ethyl-pyrrolidin-2S-ylmethyl)-4-fluoro-benzamide;

N-[3-(1H-benzotriazol-5-yl)-benzyl]-4-fluoro-N-(2-pyrrolidin-1-yl-ethyl)-benzamide hydrochloride;

thiophene-2-carboxylic acid [5-(1H-benzotriazol-5-yl)-2-fluoro-benzyl]-(2-pyrrolidin-1-yl-ethyl)-amide hydrochloride;

N-[5-(1H-benzotriazol-5-yl)-2-fluoro-benzyl]-2,4-difluoro-N-(2-pyrrolidin-1-yl-ethyl)-benzamide hydrochloride;

N-[5-(1H-benzotriazol-5-yl)-2-fluoro-benzyl]-4-fluoro-N-(2-pyrrolidin-1-yl-ethyl)-benzamide;
N-[5-(1H-benzotriazol-5-yl)-2-fluoro-benzyl]-4-fluoro-N-piperidin-4-yl-benzamide;
N-[5-(1H-benzotriazol-5-yl)-2-fluoro-benzyl]-4-fluoro-N-(1-isopropyl-piperidin-4-yl)-benzamide;
N-[5-(1H-benzotriazol-5-yl)-2-fluoro-benzyl]-N-(1-cyclopropyl-piperidin-4-yl)-4-fluoro-benzamide;
N-[5-(1H-benzotriazol-5-yl)-2-fluoro-benzyl]-N-(1-methyl-piperidin-4-yl)-4-fluoro-benzamide;
5-[3-(4-methyl-piperazin-1-ylmethyl)-phenyl]-1H-benzotriazole;
5-[4-fluoro-3-(4-methyl-piperazin-1-ylmethyl)-phenyl]-1H-benzotriazole; and
5-{4-fluoro-3-[2S-(4-fluoro-phenyl)-piperazin-1-ylmethyl]-phenyl}-1H-benzotriazole;
or a pharmaceutically acceptable salt thereof or an optical or stereoisomer thereof.

In yet another embodiment of this invention the compound of formula (I) is having the following substituents:

$$X=Y$$

denotes a single bond between X and Y;
X is CHR;
Y is CHR;
Z is NR;
A, B and E are CH;
Ar is phenyl, fluorophenyl, chlorophenyl, pyridinyl, pyrazinyl, furanyl or thiophenyl;
each R is independently chosen from hydrogen, methyl, ethyl or $CF_3$;
$R_1$ and $R_2$ are the same or different and selected independently of each other from benzyl, fluorobenzyl, fluorobenzoyl, difluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, thiophenylmethyl, N-methyl-aza-bicyclo[2.2.2]octyl, aza-bicyclo[2.2.2]octyl, aza-bicyclo[2.2.2]octylmethyl, N-methyl-piperidinyl, N-isopropyl-piperidinyl, N-cyclopropyl-piperidinyl, piperidinyl, N-methyl-pyrrolidinyl, N-ethyl-pyrrolidinylmethyl, pyrrolidinylmethyl, pyrrolidinylethyl, pyrrolidinylpropyl, methylaminoethyl, dimethylaminoethyl and dimethylaminopropyl;
or
$R_1$ and $R_2$ taken together with the nitrogen atom to which they are attached form a unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

An example of a compound of formula (I) falling within the scope of the above noted embodiment includes without any limitations the following:
N-[5-(2,3-dihydro-1H-indol-5-yl)-2-fluoro-benzyl]-N-(2-dimethylamino-ethyl)-4-fluoro-benzamide;
or a pharmaceutically acceptable salt thereof or an optical or stereoisomer thereof.

In yet another embodiment of this invention the compound of formula (I) is having the following substituents:

$$X=Y$$

denotes a single bond between X and Y;
X is O, S or NR;
Y is CO;
Z is NR;
A, B and E are CH;
Ar is phenyl, fluorophenyl, chlorophenyl, pyridinyl, pyrazinyl, furanyl or thiophenyl;
each R is independently chosen from hydrogen, methyl or ethyl;
$R_1$ and $R_2$ are the same or different and selected independently of each other from benzyl, fluorobenzyl, benzoyl, fluorobenzoyl, difluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, thiophenylmethyl, N-methyl-aza-bicyclo[2.2.2]octyl, aza-bicyclo[2.2.2]octyl, aza-bicyclo[2.2.2]octylmethyl, N-methyl-piperidinyl, N-isopropyl-piperidinyl, N-cyclopropyl-piperidinyl, piperidinyl, N-methyl-pyrrolidinyl, N-ethyl-pyrrolidinylmethyl, pyrrolidinylmethyl, pyrrolidinylethyl, pyrrolidinylpropyl, methylaminoethyl, dimethylaminoethyl and dimethylaminopropyl;
or
$R_1$ and $R_2$ taken together with the nitrogen atom to which they are attached form a unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Examples of compounds of formula (I) falling within the scope of the above noted embodiment include without any limitations the following:
6-(3-{[benzyl-(2-dimethylamino-ethyl)-amino]-methyl}-phenyl)-3H-benzothiazol-2-one hydrochloride;
N-(2-dimethylamino-ethyl)-N-[3-(2-oxo-2,3-dihydro-benzothiazol-6-yl)-benzyl]-benzamide hydrochloride;
4-chloro-N-(2-dimethylamino-ethyl)-N-[3-(2-oxo-2,3-dihydro-benzothiazol-6-yl)-benzyl]-benzamide hydrochloride;
N-(3-dimethylamino-propyl)-N-[3-(2-oxo-2,3-dihydro-benzothiazol-6-yl)-benzyl]-benzamide; hydrochloride;
6-(3-{[benzyl-(2-dimethylamino-ethyl)-amino]-methyl}-phenyl)-3H-benzooxazol-2-one hydrochloride;
6-(5-{[(2-dimethylamino-ethyl)-(4-fluoro-benzyl)-amino]-methyl}-pyridin-3-yl)-3H-benzooxazol-2-one;
6-(5-{[(2-dimethylamino-ethyl)-(4-fluoro-benzyl)-amino]-methyl}-furan-3-yl)-3H-benzooxazol-2-one;
6-(3-{[(1-ethyl-pyrrolidin-2R-ylmethyl)-(4-fluoro-benzyl)-amino]-methyl}-4-fluoro-phenyl)-3H-benzooxazol-2-one trifluoro-acetate;
6-(4-fluoro-3-{[(4-fluoro-benzyl)-(1-methyl-piperidin-4-yl)-amino]-methyl}-phenyl)-3H-benzooxazol-2-one;
6-(5-{[(4-fluoro-benzyl)-(1-methyl-piperidin-4-yl)-amino]-methyl}-furan-3-yl)-3H-benzooxazol-2-one;

4-fluoro-N-[2-fluoro-5-(2-oxo-2,3-dihydro-benzooxazol-6-yl)-benzyl]-N-(2-pyrrolidin-1-yl-ethyl)-benzamide;
N-(2-dimethylamino-ethyl)-N-[3-(2-oxo-2,3-dihydro-benzooxazol-6-yl)-benzyl]-benzamide hydrochloride;
N-(1-ethyl-pyrrolidin-2-ylmethyl)-4-fluoro-N-[2-fluoro-5-(2-oxo-2,3-dihydro-benzooxazol-6-yl)-benzyl]-benzamide;
4-chloro-N-(2-dimethylamino-ethyl)-N-[3-(2-oxo-2,3-dihydro-benzooxazol-6-yl)-benzyl]-benzamide hydrochloride;
N-(1-ethyl-pyrrolidin-2R-ylmethyl)-4-fluoro-N-[2-fluoro-5-(2-oxo-2,3-dihydro-benzooxazol-6-yl)-benzyl]-benzamide trifluoro-acetate;
4-fluoro-N-[2-fluoro-5-(2-oxo-2,1-dihydro-benzooxazol-6-yl)-benzyl]-N-(1-methyl-piperidin-4-yl)-benzamide;
N-(1-aza-bicyclo[2.2.2]oct-3S-yl)-4-fluoro-N-[2-fluoro-5-(2-oxo-2,3-dihydro-benzooxazol-6-yl)-benzyl]-benzamide hydrochloride;
N-(1-aza-bicyclo[2.2.2]oct-3R-yl)-4-fluoro-N-[2-fluoro-5-(2-oxo-2,3-dihydro-benzooxazol-6-yl)-benzyl]-benzamide hydrochloride;
N-(2-dimethylamino-ethyl)-4-fluoro-N-[2-fluoro-5-(2-oxo-2,3-dihydro-benzooxazol-6-yl)-benzyl]-benzamide;
6-[3-(4-methyl-piperazin-1-ylmethyl)-phenyl]-3H-benzooxazol-2-one;
6-{5-[2R-(4-fluoro-phenyl)-4-methyl-piperazin-1-ylmethyl]-furan-3-yl}-3H-benzooxazol-2-one;
6-{5-[2S-(4-fluoro-phenyl)-4-methyl-piperazin-1-ylmethyl]-furan-2-yl}-3H-benzooxazol-2-one;
6-{5-[2S-(4-fluoro-phenyl)-4-methyl-piperazin-1-ylmethyl]-thiophen-3-yl}-3H-benzooxazol-2-one;
6-[4-fluoro-3-(2-thiophen-2-yl-piperazin-1-ylmethyl)-phenyl]-3H-benzooxazol-2-one;
6-{5-[2S-(4-fluorophenyl)-4-methylpiperazine-1-ylmethyl]-furan-3-yl}-3H-benzooxazol-2-one;
6-{5-[2S-(4-fluoro-phenyl)-piperazin-1-ylmethyl]-furan-3-yl}-3H-benzooxazol-2-one acetate;
6-{4-fluoro-3-[2S-(4-fluoro-phenyl)-4-methyl-piperazin-1-ylmethyl]-phenyl}-3H-benzooxazol-2-one;
6-{5-[2S-(4-fluoro-phenyl)-4-methyl-piperazin-1-ylmethyl]-pyridin-3-yl}-3H-benzooxazol-2-one acetate; and
5-(3-{[benzyl-(2-dimethylamino-ethyl)-amino]-methyl}-phenyl)-1,3-dihydro-benzoimidazol-2-one hydrochloride;
or a pharmaceutically acceptable salt thereof or an optical or stereoisomer thereof.

In yet another embodiment of this invention the compound of formula (I) is having the following substituents:

$$X=Y$$

denotes a single bond between X and Y;
X is O or CO;
Y is CHR or NR;
Z is CONR;
A, B and E are the same or different and independently from each other are CH or N;
Ar is phenyl, fluorophenyl, chlorophenyl, pyridinyl, pyrazinyl, furanyl or thiophenyl;
each R is independently chosen from hydrogen, methyl or ethyl;
$R_1$ and $R_2$ are the same or different and selected independently of each other from benzyl, fluorobenzyl, benzoyl, fluorobenzoyl, difluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydrobenzo[1,4]dioxinylcarbonyl, benzo[1,3]dioxolylcarbonyl, thiophenylmethyl, N-methyl-aza-bicyclo[2.2.2]octyl, aza-bicyclo[2.2.2]octyl, aza-bicyclo[2.2.2]octylmethyl, N-methyl-piperidinyl, N-isopropyl-piperidinyl, N-cyclopropyl-piperidinyl, piperidinyl, N-methyl-pyrrolidinyl, N-ethyl-pyrrolidinylmethyl, pyrrolidinylmethyl, pyrrolidinylethyl, pyrrolidinylpropyl, methylaminoethyl, dimethylaminoethyl and dimethylaminopropyl;
or
$R_1$ and $R_2$ taken together with the nitrogen atom to which they are attached form a unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Examples of compounds of formula (I) falling within the scope of the above noted embodiment include without any limitations the following:

6-(3-{[benzyl-(2-dimethylamino-ethyl)-amino]-methyl}-phenyl)-3-methyl-1H-quinazoline-2,4-dione hydrochloride; and
7-(3-{[benzyl-(2-dimethylamino-ethyl)-amino]-methyl}-phenyl)-4H-pyrido[3,2-b][1,4]oxazin-3-one hydrochloride;
or a pharmaceutically acceptable salt thereof or an optical or stereoisomer thereof.

In yet another embodiment of this invention the compound of formula (I) is having the following substituents:

$$X=Y$$

denotes a double bond between X and Y;
X is CR;
Y is CR;
Z is NR;
A, B and E are the same or different and independently from each other are CH or N;
D is CO;
Ar is phenyl, fluorophenyl, chlorophenyl, pyridinyl, pyrazinyl, furanyl or thiophenyl;
each R is independently chosen from hydrogen, methyl, ethyl, methoxy, fluorine, $CF_3$ or $OCF_3$;
$R_1$ and $R_2$ are the same or different and selected independently of each other from benzyl, fluorobenzyl, benzoyl, fluorobenzoyl, difluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydrobenzo[1,4]dioxinylcarbonyl, benzo[1,3]dioxolylcarbonyl, thiophenylmethyl, N-methyl-aza-bicyclo[2.2.2]octyl, aza-bicyclo[2.2.2]octyl, aza-bicyclo[2.2.2]octylmethyl, N-methyl-piperidinyl, N-isopropyl-piperidinyl, N-cyclopropyl-piperidinyl, piperidinyl, N-methyl-pyrrolidinyl, N-ethyl-pyrrolidinylmethyl, pyrrolidinylmethyl, pyrrolidinylethyl, pyrrolidinylpropyl, methylaminoethyl, dimethylaminoethyl and dimethylaminopropyl;

or

R$_1$ and R$_2$ taken together with the nitrogen atom to which they are attached form a unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

An example of a compound of formula (I) falling within the scope of the above noted embodiment includes without any limitations the following:

[2-fluoro-5-(1H-indol-5-yl)-phenyl]-[2S-(4-fluoro-phenyl)-4-methyl-piperazin-1-yl]-methanone;

or a pharmaceutically acceptable salt thereof or an optical or stereoisomer thereof.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein.

More specifically, the compounds disclosed herein can be synthesized according to the following procedures of Schemes 1-10, wherein the X, Y, Z, A, B, D, E, Ar, R$_1$ and R$_2$ are as defined for Formula I unless otherwise indicated.

Schemes 1 and 2 illustrate synthesis of a key intermediate II used in the preparation of compounds of formula I. However, the intermediate aldehyde II can be synthesized by any of the methods known in the art.

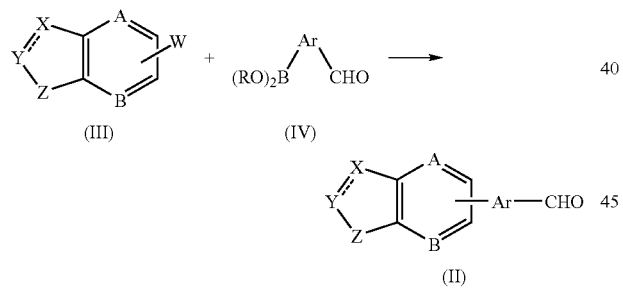

As shown in Scheme 1, the aldehyde II is prepared starting from a compound of the formula III, wherein W is halogen or trifluoromethanesulfonate (triflate). As illustrated, III is reacted with boronic acid or ester of the formula IV (wherein R is hydrogen, C$_{1-4}$alkyl or the two R's taken together with the oxygen atoms to which they are attached form a five or six membered ring) to obtain aldehyde intermediate II. This reaction can be carried out by any of the methods known in the art. For example, such addition reactions are carried out in the presence of a suitable catalyst such as palladium compounds. Examples of palladium compounds suitable for such coupling reactions include tetrakis(triphenylphosphine)palladium chloride or PdCl$_2$(dppf) (dppf=1,1'bis(diphenylphosphino)ferrocene), and the like. The reaction is also generally carried out in the presence of a suitable base, such as for example, cesium carbonate and the like. Further, any groups that may interfere with this addition reaction may need to be protected. For instance, when Z=NH, the nitrogen may be suitably protected before carrying out this coupling reaction. Any of the known nitrogen protecting groups can be employed as long as such protecting groups do not interfere with this reaction. Such protecting groups are described in T. W. Greene, Protective Groups in Organic Synthesis, J. Wiley-Interscience Publication (1999). The reaction can further be carried out in a suitable solvent preferably an organic solvent such as dioxane, dimethylsulfoxide, dimethylformamide, or the like, or in the presence of water as a co-solvent, and at subambient to superambient temperature conditions. Normally, the reaction is carried out at elevated temperatures, for example, at the reflux temperature of the solvent and preferably in an inert atmosphere. The reaction mixture can be heated using conventional methods or alternatively using microwave irradiation. However, as noted above, any of the other known methods can also be used to bring about this coupling reaction to form the aldehyde II.

Alternatively, the aldehyde II can also be prepared using a boronic acid or ester of formula V and an aromatic aldehyde of formula VI as illustrated in Scheme 2. This coupling reaction can essentially be carried out under similar conditions as described above in order to obtain the aldehyde II.

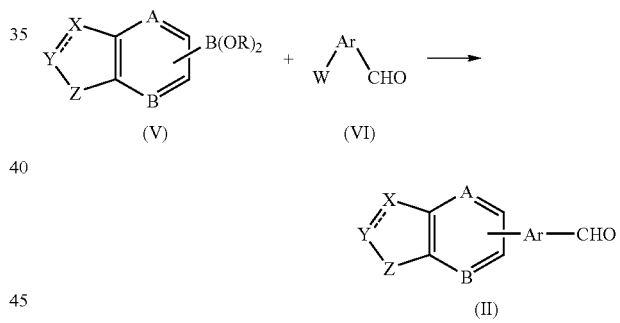

Scheme 3 illustrates preparation of a series of compounds of formula I wherein D is CH$_2$ and R$_2$ is either Ar'CH$_2$ or Ar'CO and wherein Ar' is aryl or heteroaryl as described herein.

In Scheme 3, the intermediate aldehyde II is reacted with a desirable amine under reductive alkylation conditions to form compound of formula VIII. This amine coupling reaction can be carried out using any of the known methods in the art. Generally such reductive amination can be carried out using a reducing agent such as sodiumcyanoborohydride, or sodium triacetoxyborohydride, (NaB(O$_2$CCH$_3$)$_3$H), and the like in a suitable reaction medium, such as tetrahydrofuran or dichloroethane. Alternatively, the reaction of the aldehyde and amine can be carried out in the presence of a dehydrating agent, such as, for example, molecular sieves, in an organic solvent such as methanol, followed by addition of a reducing agent such as sodium borohydride.

Scheme 3

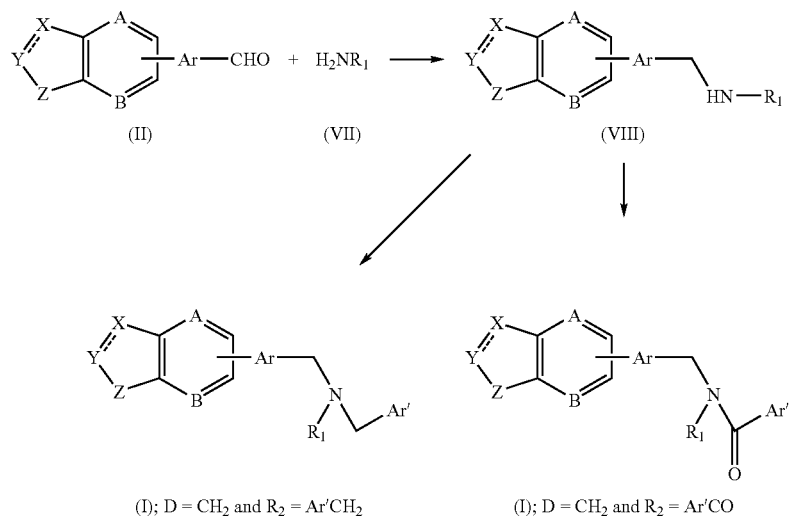

The intermediate amino compound VIII thus formed is then subjected to another reductive alkylation reaction using a suitable aromatic aldehyde to form compounds of formula I wherein D=CH$_2$ and R$_2$=Ar'CH$_2$. This alkylation reaction can also be carried out under essentially similar conditions as described above. That is, compound of formula VIII is reacted with Ar'CHO in the presence of a suitable reducing agent such as sodium triacetoxyborohydride (NaB(O$_2$CCH$_3$)$_3$H) to form the corresponding compound of formula I. The compound of formula VIII can be reacted with a suitable aromatic carboxylic acid of formula Ar'CO$_2$H or carboxylic acid chloride to form compound of formula I wherein D=CH$_2$ and R$_2$=Ar'CO. This reaction can again be carried out using any of the methods known in the art. For instance such acylation reactions with carboxylic acid chlorides are carried out in the presence of a suitable base such as triethylamine or diisopropylethylamine in an organic solvent such as dichloromethane. Alternatively reaction of the compound of formula VIII with a carboxylic acid and an amine coupling reagent such as, for example, O-(7-azabenzotriazol-1-yl)-N,N,N',N'-tetramethyluronium hexafluorophosphate (HATU) in the presence of a base such as diisopropylethylamine also affords compounds of formula 1.

Scheme 4

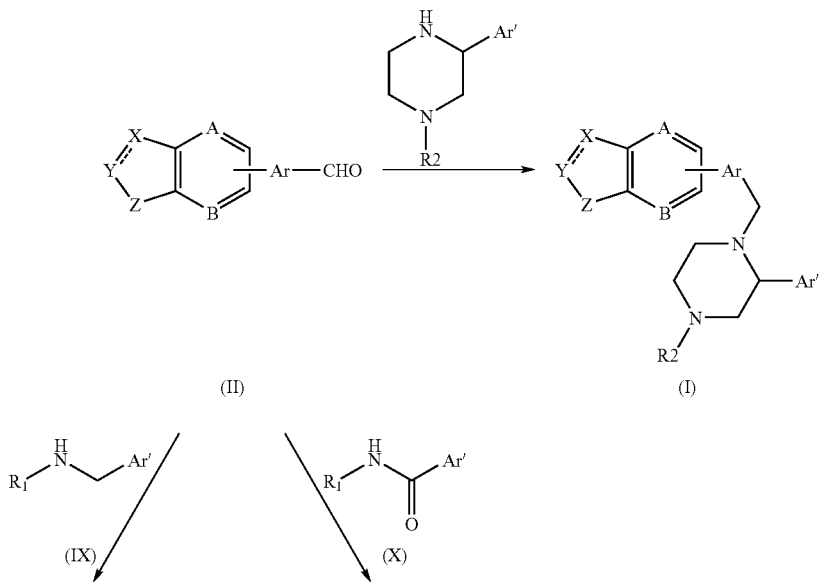

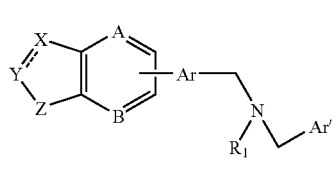
(I); D = CH₂ and R₂ = Ar'CH₂

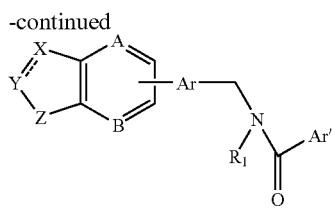
(I); D = CH₂ and R₂ = Ar'CO

Alternatively, compounds of formula I of the types shown in Scheme 3 can also be prepared starting from the aldehyde II and a suitable amino compound IX or X as illustrated in Scheme 4. The compound of formula II can also be reacted with cyclic amines such as piperidine derivatives shown to form the corresponding compounds of formula I. Again this amination reaction can be carried out under similar conditions as described above. That is, the aldehyde II is reacted with suitable amine IX or piperidine derivative or suitable amide X in the presence of a suitable reducing agent such as sodium triacetoxyborohydride (NaB(O₂CCH₃)₃H) to form the corresponding compounds of formula I.

Scheme 5 illustrates further variation of a synthetic method for the preparation of compounds of formula I. In this approach, halo-aromatic aldehyde of formula VI is first reacted with an amine to form compound of formula XI, which is reacted either with aralkyl halide or aromatic carboxylic acid to form corresponding compounds of formula XII and XIII. The latter compounds are finally reacted with boronic acids or esters of formula V to form the corresponding compounds of formula I wherein D=CH₂ and R₂ is either Ar'CH₂ or Ar'CO.

Scheme 5

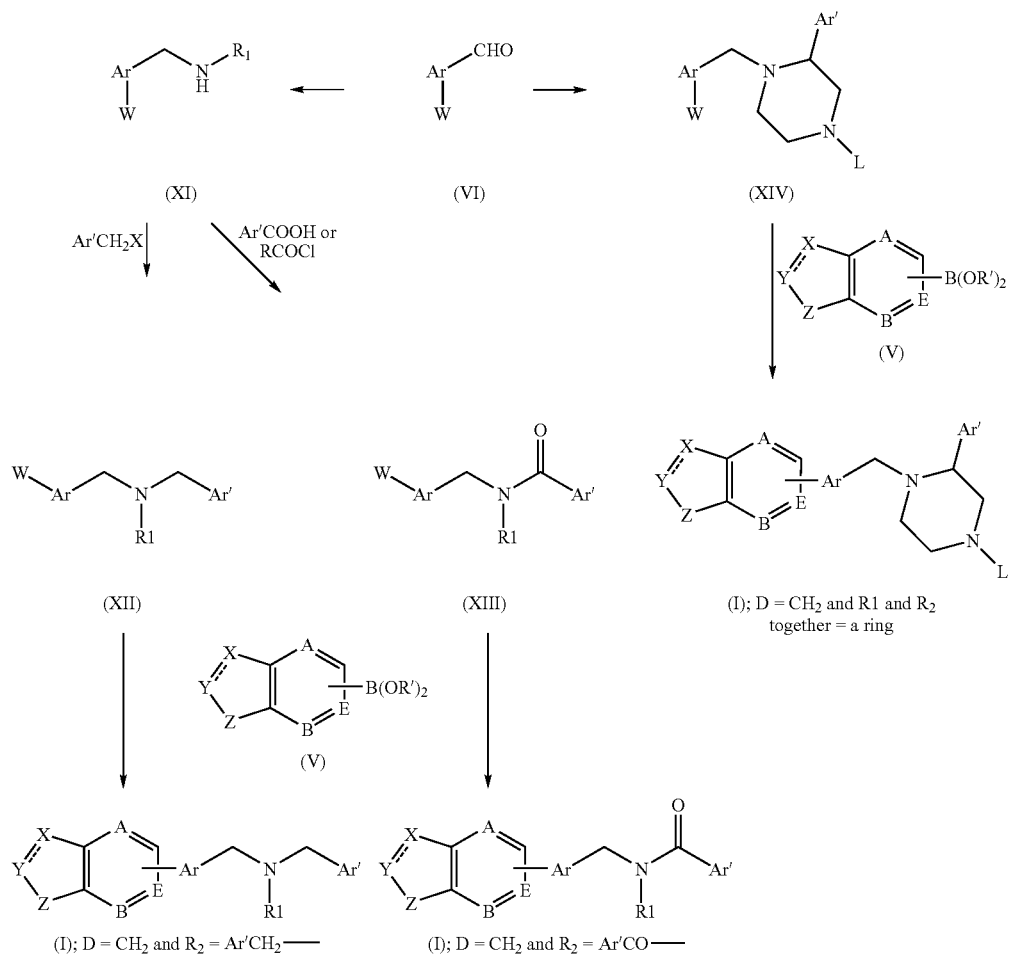

Similar reaction conditions can be employed for various steps set forth in Scheme 5 as described above. For instance, the reductive amination reaction of the halo-aromatic aldehyde VI with the amine is affected under reductive conditions in the presence of a reducing agent such as sodium triacetoxyborohydride as discussed above for similar reductive amination reactions. The amino compound XI so formed is then subjected to arylation or aroylation by reacting respectively with aralkyl halide such as arylmethylhalide of formula Ar'CH$_2$-halo or an aromatic carboxylic acid such as Ar'CO$_2$H under conditions as described in scheme 4 to obtain the corresponding compounds of formula XII and XIII. Finally, each of which is reacted with the boron compound V to form the corresponding compound of formula I.

The compounds of formula I may also be prepared as outlined in Scheme 6, using the methods described above. For example, the reductive alkylation reaction of the boranyl-aromatic aldehyde XV with an amine is affected under reductive conditions in the presence of a reducing agent such as sodium triacetoxyborohydride as discussed above for similar reductive alkylation reactions. Further treatment of the amine obtained with an aldehyde under similar conditions then provides the boranyl-amine XVI. This boronic acid or ester can then be coupled to an aryl or heteroaryl halide or trifluoromethanesulfonate, in the presence of a suitable organometallic coupling agent as described earlier to afford compounds of formula I.

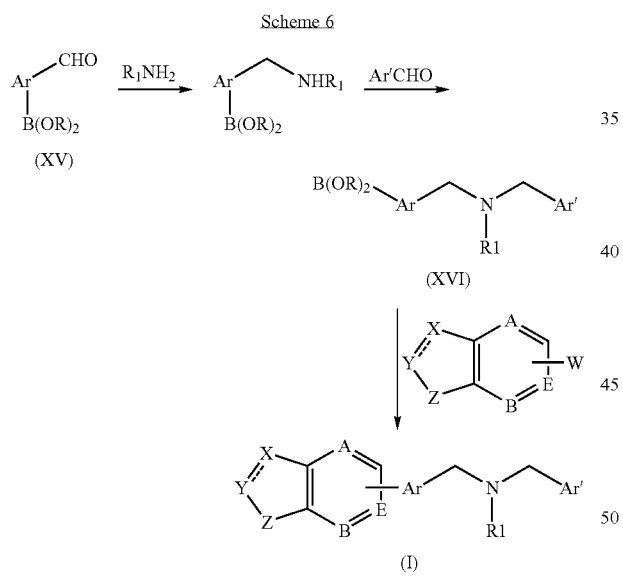

In a similar fashion, as shown in Scheme 7, the boranyl-amine XVII may be prepared by treatment of an amino substituted aryl halide or triflate with a borylating agent such as bis(pinacolato)diboron in the presence of an organometallic coupling agent such as Pd(dppf).DCM in an organic solvent such as dioxane, dimethylsulfoxide or dimethylformamide at elevated temperature. This boronic acid or ester can then be coupled with an aryl halide or trifluoromethanesulfonate under the conditions described above, or for example using fibreCat 1001 in the presence of a phase transfer catalyst such as tetrabutylammonium bromide, a base such as cesium carbonate in a mixture of an organic solvent such as dioxane and water at elevated temperatures.

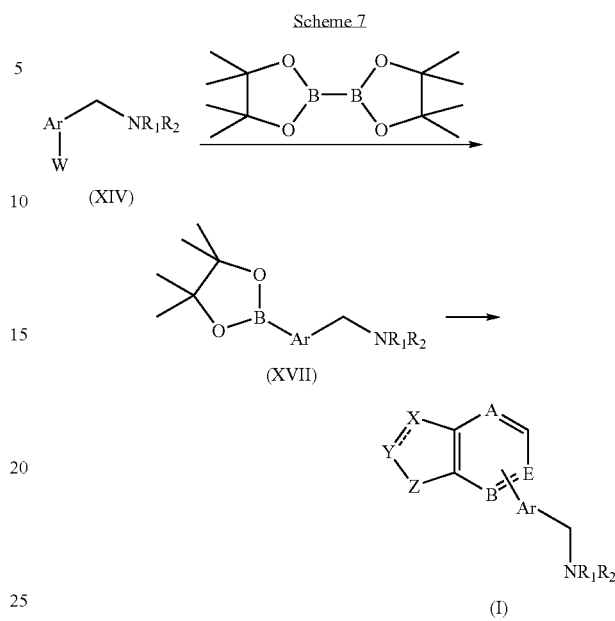

Compounds of formula I may also be prepared as outlined in Scheme 8. Carboxylic acids or esters may be prepared as described for aldehydes in Schemes 1 and 2. Reduction of the acids or esters to the alcohols XIX may be carried out by any number of methods known in the art, including the use of, for example, hydride reducing agents such as lithium aluminum hydride in an appropriate solvent such as diethyl ether or THF. The alcohols so prepared can be activated by transformation into a halide, a mesylate, triflate or nosylate. For example mesylates may be prepared by treating the alcohols with methanesulfonyl chloride or methanesulfonyl anhydride in the presence of a base such as triethyl amine or diisopropylethylamine in an appropriate solvent such as DCM or DCE. Compounds XX can then be transformed to the targets of formula I by treatment with an appropriate amine.

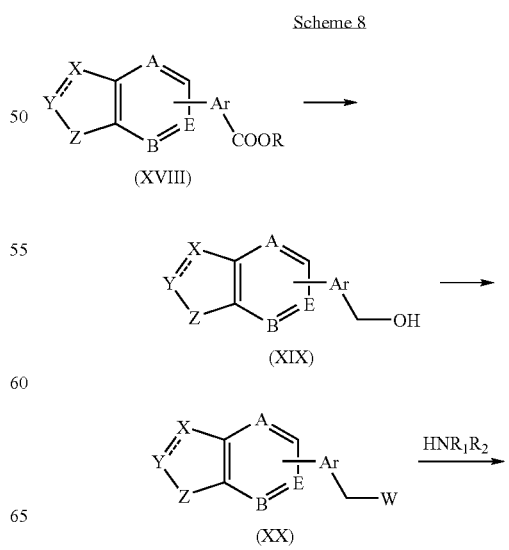

-continued

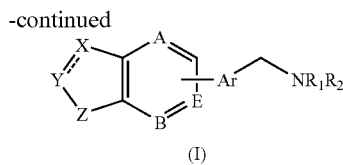

(I)

Compounds of formula I in which D=CO may be prepared by methods similar to those described above, replacing a reductive alkylation with an amide forming reaction. For example (Scheme 9), in a method related to the one described in Scheme 5, amidation of a carboxylic acid or carboxylic acid derivative can be accomplished by many known methods. For example amides XXII may be obtained by treatment of carboxylic acids XXI (R″=H) upon treatment with an amine in the presence of a coupling agent, such as HOBT, HOAT or HATU, with a base such as triethylamine or diisopropylamine in an appropriate solvent, for example dimethylformamide or dichloromethane. Subsequent organometallic coupling as described above provides compounds of formula I (D=CO).

Scheme 9

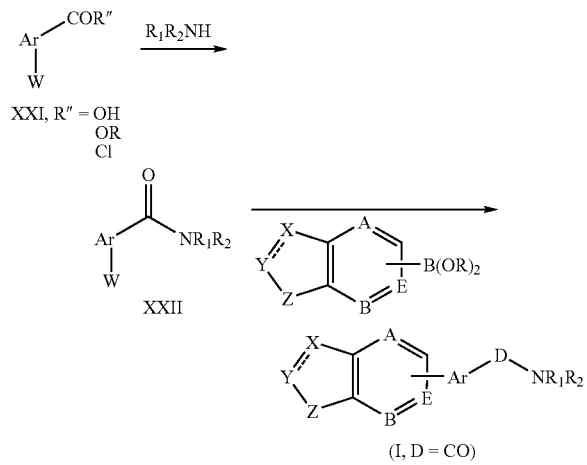

In an alternative approach to the preparation of the compounds of this invention, the heterocyclic ring formed by X, Y, and Z may be prepared by any of a variety of methods known in the art. For example, as shown in Scheme 10, an indole may be prepared from a suitably substituted biaryl or heteroaryl (prepared by the methods described above). Treatment of the nitro compound XXI with dimethylformamide dimethylacetal in a suitable solvent, such as dimethylformamide, followed by hydrogenation using a Pd or Pt catalyst (for example 10% Pd supported on carbon) provides an compound of formula I where X, Y, and Z are C=C—N and are part of an indole.

Scheme 10

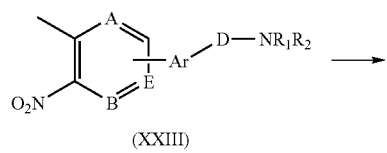

(XXIII)

-continued

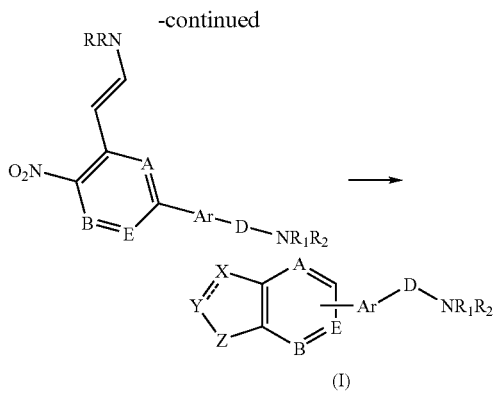

(I)

As noted above, various modifications can be made to the above described schemes in order to prepare various other compounds of formula I employing suitable starting materials and using other methods known in the art. A wide variety of such specific synthetic examples are further provided below.

In another aspect of this invention, a specific disease, a disorder or a condition that can be treated with the compound of this invention include, without any limitation a wide variety of sleep disorders. In addition, the compounds of this invention are selective serotonin antagonists particularly the compounds of this invention are selective antagonists at the $5HT_{2A}$ receptor.

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease caused by the effects of $5HT_{2A}$ receptor. That is, as noted above, the compounds of the present invention are selective $5HT_{2A}$ antagonists and thus may be effectively administered to ameliorate any disease state which is mediated all or in part by $5HT_{2A}$ receptor.

All of the various embodiments of the compounds used in the methods of this invention as disclosed herein can be used in the method of treating various disease states as described herein. As stated herein, the compounds used in the method of this invention are capable of antagonizing the effects of $5HT_{2A}$ receptor and thereby alleviating the effects and/or conditions caused due to the activity of $5HT_{2A}$ receptor.

In a specific embodiment of this invention the compounds of this invention are particularly suitable for the treatment of a variety of sleep disorders. The term "sleep disorder" as used herein shall mean all of the description as delineated in the Diagnostic and Statistical Manual of Mental Disorders, 4th Edition (1994), hereafter referred to as DSM-IV, published by the American Psychiatric Association. Specific sleep disorders that can be treated in accordance with this invention include without any limitation insomnia, primary insomnia, sleep disorder related to another mental disorder, substance induced sleep disorder and obstructive sleep apnea. Further description and discussion of sleep disorders are found in the International Classification of Sleep Disorders: Diagnostic and Coding Manual (1990), published by the American Sleep Disorders Association.

The term "insomnia" as used herein includes all sleep disorders, which are not caused due to other factors such as mental disorders, other medical conditions and substance induced sleep disorders. Insomnia as used herein shall also mean primary sleep disorders as defined in DSM-IV, which includes two sub-categories, namely, dyssomnias and parasomnias.

The term "primary insomnia" shall mean all of the definitions provided in DSM-IV. In addition, "primary insomnia" as used herein also includes "sleep maintenance insomnia." The DSM-IV lists the diagnostic criteria for primary insomnia as follows:

A. The predominant complaint is difficulty initiating or maintaining sleep, or nonrestorative sleep, for at least one month.
B. The sleep disturbance (or associated day time fatigue) causes clinically significant distress or impairment in social, occupational, or other important areas of functioning.
C. The sleep disturbance does not occur exclusively during the course of narcolepsy, breathing-related sleep disorder, circadian rhythm sleep disorder, or a parasomnia.
D. The disturbance does not occur exclusively during the course of another mental disorder (e.g., major depressive disorder, generalized anxiety disorder, a delirium).
E. The disturbance is not due to the direct physiological effects of a substance (e.g., a drug of abuse, a medication) or a general medical condition.

The term "sleep disorder related to another mental disorder" as used herein includes both insomnia and hypersomnia related to another mental disorder. The DSM-IV lists the diagnostic criteria for insomnia related to another mental disorder as follows:

A. The predominant complaint is difficulty initiating or maintaining sleep, or nonrestorative sleep, for at least one month that is associated with daytime fatigue or impaired daytime functioning.
B. The sleep disturbance (or daytime sequelae) causes clinically significant distress or impairment in social, occupational, or other important areas of functioning.
C. The insomnia is judged to be related to another axis I or axis II disorder (e.g., major depressive disorder, generalized anxiety disorder, adjustment disorder with anxiety, schizophrenia, etc.), but is sufficiently severe to warrant independent clinical attention.
D. The disturbance is not better accounted for by another sleep disorder (e.g., narcolepsy, breathing-related sleep disorder, a parasomnia).
E. The disturbance is not due to the direct physiological effects of a substance (e.g., a drug of abuse, a medication) or a general medical condition.

Similarly, the DSM-IV lists the diagnostic criteria for hypersomnia related to another mental disorder as follows:

A. The predominant complaint is excessive sleepiness for at least one month as evidenced by either prolonged sleep episodes or daytime sleep episodes that occur almost daily.
B. The excessive sleepiness causes clinically significant distress or impairment in social, occupational, or other important areas of functioning.
C. The hypersomnia is judged to be related to another axis I or axis II disorder (e.g., major depressive disorder, dysthymic disorder, schizophrenia, etc.), but is sufficiently severe to warrant independent clinical attention.
D. The disturbance is not better accounted for by another sleep disorder (e.g., narcolepsy, breathing-related sleep disorder, a parasomnia) or by an inadequate amount of sleep.
E. The disturbance is not due to the direct physiological effects of a substance (e.g., a drug of abuse, a medication) or a general medical condition.

The term "substance induced sleep disorder" as used herein means a prominent disturbance in sleep that is sufficiently severe to warrant independent clinical attention and is judged to be due to the direct physiological effects of a substance (i.e., a drug of abuse, a medication, or toxin exposure). Specific examples of drug of abuse, a medication or toxin exposure as referred to herein include without any limitations caffeine, alcohol, amphetamine, opioids, sedatives, hypnotics, anxiolytics, and the like. The DSM-IV lists the diagnostic criteria for substance induced sleep disorder as follows:

A. A prominent disturbance in sleep that is sufficiently severe to warrant independent clinical attention.
B. There is evidence from the history, physical examination, or laboratory findings of either (1) or (2): (1) the symptoms in criterion A developed during, or within a month of, substance intoxication or withdrawal; (2) medication use is etiologically related to the sleep disturbance.
C. The disturbance is not better accounted for by a sleep disorder that is not substance induced. Evidence that the symptoms are better accounted for by a sleep disorder that is not substance induced might include the following: the symptoms precede the onset of the substance use (or medication use); the symptoms persist for a substantial period of time (e.g., about a month) after the cessation of acute withdrawal or severe intoxication, or are substantially in excess of what would be expected given the type or amount of the substance used or the duration of use; or there is evidence that suggests the existence of an independent non-substance-induced sleep disorder (e.g., a history of recurrent non-substance-related episodes).
D. The disturbance does not occur exclusively during the course of a delirium.
E. The sleep disturbance causes clinically significant distress or impairment in social, occupational, or other important areas of functioning.

As used herein "withdrawal" refers to a syndrome characterized by untoward physical changes that occur following cessation of or reduction in substance use, or administration of a pharmacologic antagonist (or medication).

The term "obstructive sleep apnea" as used herein is breathing related sleep disorder as defined in DSM-IV. It is also referred to as upper airway resistance syndrome and generally involves repeated episodes of upper-airway obstruction during sleep and is normally characterized by loud snores or brief gasps that alternate with episodes of silence. The DSM-IV lists the diagnostic criteria for breathing related sleep disorder as follows:

A. Sleep disruption, leading to excessive sleepiness or insomnia, that is judged to be due to a sleep-related breathing condition (e.g., obstructive sleep or central sleep apnea syndrome or central alveolar hypoventilation syndrome).
B. The disturbance is not better accounted for by another mental disorder and is not due to the direct physiological effects of a substance (e.g., a drug of abuse, a medication) or another general medical condition (other than a breathing related disorder).

Subjective and Objective Determinations of Sleep Disorders: There are a number of ways to determine whether the onset, duration or quality of sleep (e.g. non-restorative or restorative sleep) is impaired or improved. One method is a subjective determination of the patient, e.g., do they feel drowsy or rested upon waking. Other methods involve the observation of the patient by another during sleep, e.g., how long it takes the patient to fall asleep, how many times does the patient wake up during the night, how restless is the patient during sleep, etc. Another method is to objectively measure the stages of sleep.

Polysomnography is the monitoring of multiple electrophysiological parameters during sleep and generally includes measurement of electro-encephalogram (EEG) activity, electroculographic activity and electromyographic activity (EMG), as well as other measurements. These results, along with observations, can measure not only sleep latency (the amount of time required to fall asleep), but also sleep continuity (overall balance of sleep and wakefulness) which may be an indication of the quality of sleep.

There are five distinct sleep stages which can be measured by polysomnography: rapid eye movement (REM) sleep and four stages of no-rapid eye movement (NREM) sleep (stages 1, 2, 3 and 4). Stage 1 NREM sleep is a transition from wakefulness to sleep and occupies about 5% of time spent asleep in healthy adults. Stage 2 NREM sleep, which is characterized by specific EEG waveforms (sleep spindles and K complexes), occupies about 50% of time spent asleep. Stages 3 and 4 NREM sleep (also known collectively as slow-wave sleep) are the deepest levels of sleep and occupy about 10-20% of sleep time. REM sleep, during which the majority of typical story like dreams occur, occupies about 20-25% of total sleep.

These sleep stages have a characteristic temporal organization across the night. NREM stages 3 and 4 tend to occur in the first one-third to one-half of the night and increase in duration in response to sleep deprivation. REM sleep occurs cyclically through the night, alternating with NREM sleep about every 80-100 minutes. REM sleep periods increase in duration toward the morning. Human sleep also varies characteristically across the life span. After relative stability with large amounts of slow-wave sleep in childhood and early adolescence, sleep continuity and depth deteriorate across the adult age range. This deterioration is reflected by increased wakefulness and stage 1 sleep and decreased stages 3 and 4 sleep.

In general, the compounds of this invention improve quality of sleep through serotonergic mechanisms (acting at the $5HT_{2A}$ receptor site) when administered to a patient suffering from any of the sleep disorders as described hereinabove. That is, in general, it has been found that the administration of compounds of this invention increases the duration of stages 3 and 4 of slow wave sleep (SWS, measured as NREM sleep). This is also measured by decrease in wake after sleep onset (WASO), the primary efficacy measure in the clinical trial. In addition, enhancement of SWS in older adults may also yield increases in cognition and enhanced quality of life. SWS could play an important role in the regulation of cognitive processes in older adults. It has been shown that there is a direct relationship between the SWS amount and performance on daily cognitive testing. Thus, it has now been found that compounds of this invention are useful in increasing cognition and thereby enhancing quality of life in a patient, preferably in older adults.

The improvement in sleep quality is measured by polysomnography. The results of polysomnographic and sleep EEG studies in small numbers of young and aged healthy volunteers, and in patients with primary insomnia have shown an increase of SWS, and a decrease in WASO.

In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal or topical route.

Finally, in yet another embodiment of this invention, there is also provided a pharmaceutical composition comprising a pharmaceutically acceptable carrier and a compound, including enantiomers, stereoisomers, and tautomers of said compound and pharmaceutically acceptable salts, solvates or derivatives thereof, with said compound having the general structure shown in formula I as described herein.

As described herein, the pharmaceutical compositions of this invention feature $5HT_{2A}$ antagonistic activity and thus are useful in treating any disease, condition or a disorder caused due to the effects of $5HT_{2A}$ in a patient. Again, as described above, all of the preferred embodiments of the compounds of this invention as disclosed herein can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the fatty acid salt, for example stearate, etc. may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof.

Similarly, the pharmaceutical compositions of this invention can also be mixed with a wide variety of pharmaceutically acceptable excipients. Examples of pharmaceutically acceptable excipients include without any limitation acacia, acesulfame potassium, albumin, aliphatic polyesters, aspartame, bentonite, butylparaben, calcium stearate, canola oil, carbomer, carboxymethylcellulose, cellulose acetate, dextrin, guar gum, hydroxyethyl cellulose, maltodextrin, starch, and the like.

When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.001 to 250 mg/kg per day, preferably about 0.005 to 100 mg/kg per day, and especially about 0.05 to 20 mg/kg per day. The compounds may be administered on a regimen of 1 to 4 times per day.

More specifically, the dosage range at which the compounds of this invention exhibit its ability to treat sleep disorders, including each specific type of sleep disorder, can vary depending upon the specific disorder, its severity, the patient, any underlying disease states that the patient is suffering from, and other medications that may be concurrently administered to the patient. Generally though, as noted above, the compounds of this invention will exhibit its ability to treat sleep disorders at a range of from about 0.0011 mg/kg/day to about 100 mg/kg/day.

This invention is further illustrated by the following examples which are provided for illustration purposes and in no way limit the scope of the present invention.

EXAMPLES

General

Reactions generally are run under an inert atmosphere. All commercial chemicals and solvents are reagent grade and were used without further purification unless otherwise specified. All reactions except those in aqueous solution or otherwise noted were carried out with the use of standard techniques for the exclusion of moisture. Flash chromatography was carried out using silica gel 60 (35-70 um) according to the literature procedure (Still, W. C.; Kahn, M; Mitra, A. *J. Org. Chem.* 1978 43, 2923) or a variation of this method using commercially available silica gel cartridges (for example Isco Redi Sep) Reactions using focused or single mode microwave irradiation were performed on instruments from CEM Corporation or Personal Chemistry. The $^1$H NMR spectra are run at 300 MHz or 400 MHz on a Gemini 300, Varian VXR 300 or Varian Inova-400 spectrometer and are determined in a deuterated solvent, such as DMSO-$D_6$ or $CDCl_3$ unless otherwise noted. Chemical shifts values are indicated in parts per million (ppm) with reference to tetramethylsilane (TMS) as the internal standard. Liquid chromatography with mass spectral analysis (LC/MS) is recorded on a Platform LC Mass Spectrometer with electrospray source operating in positive and negative ion mode and an HP1100 with inline HP1100 DAD detection and SEDEX ELS detection using a Waters XTerra MS C18 3.5 µm 4.6×30 mm or a Phenomenex Luna C18(2) 30×4.6 mm column eluting with 0.1% formic acid in water/acetonitrile (short LC/MS), or a Finnigan TSQ700 Mass Spectrometer with electrospray source operating in positive ion mode and an HP1050 system with inline HP1050 Single Wavelength UV detector at 254 nm using a Higgins Clipeus C18 5 um 100×3.0 mm column eluting with 0.1% formic acid in water/acetonitrile (long LC/MS), or a Micromass LCTAPI LC-TOF (time of flight) Mass Spectrometer and Masslynx Data System. Ionization mode=electrospray (esi), values are determined for the protonated molecular ions ($M^+ +1$) using a Synergi 2U HYDRO-RP 20×4 mm column, eluting with 0.1% trifluoroacetic acid (TFA) in water/acetonitrile (method 3)

As used in the examples and preparations that follow, the terms used therein shall have the meanings indicated: "kg" refers to kilograms, "g" refers to grams, "mg" refers to milligrams, "µg" refers to micrograms, "pg" refers to picograms, "lb" refers to pounds, "oz" refers to ounces, "mol" refers to moles, "mmol" refers to millimoles, "µmole" refers to micromoles, "nmole" refers to nanomoles, "L" refers to liters, "mL" or "ml" refers to milliliters, "µL" refers to microliters, "gal" refers to gallons, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "dppf" refers to 1,1' bis(diphenylphosphino)ferrocene, "THF" refers to tetrahydrofuran, "DMF" refers to dimethylformamide, "DMAP" refers to dimethylaminopyridine; "DMSO" refers to dimethylsulfoxide; "NMP" refers to 1-methyl-2-pyrrolidinone, "DCM" refers to dichloromethane, "DCE" refers to dichloroethane, "EtOAc" refers to ethyl acetate, "MeOH" refers to methanol, "HOAc" or "AcOH" refers to acetic acid, "$H_2O$" refers to water; "NaOH" refers to sodium hydroxide, "HCl" refers to hydrochloric acid, "$Cs_2CO_3$" refers to cesium carbonate, "$MgSO_4$" refers to magnesium sulfate, "$Na_2SO_4$" refers to sodium sulfate, "brine" refers to a saturated aqueous sodium chloride solution, "HATU" refers to O-(7-azabenzotriazol-1-yl)-1,1,3,3-tetramethyluronium hexafluorophosphate, "M" refers to molar, "mM" refers to millimolar, "µM" refers to micromolar, "nM" refers to nanomolar, "N" refers to normal, "TLC" refers to thin layer chromatography, "HPLC" refers to high performance liquid chromatography, "HRMS" refers to high resolution mass spectrum, "L.O.D." refers to loss on drying, "µCi" refers to microcuries, "i.p." refers to intraperitoneally, "i.v." refers to intravenously, anhyd=anhydrous; aq=aqueous; min=minute; hr=hour; d=day; sat.=saturated; s=singlet, d=doublet; t=triplet; q=quartet; m=multiplet; dd=doublet of doublets; br=broad; LC=liquid chromatograph; MS=mass spectrograph; ESI/MS=electrospray ionization/mass spectrograph; RT=retention time; M=molecular ion.

The following examples describe the procedures used in the preparation of the compounds of this invention.

Example 1

N-Benzyl-N-[3-(1H-indol-5-yl)-benzyl]-N',N'-dimethyl-ethane-1,2-diamine

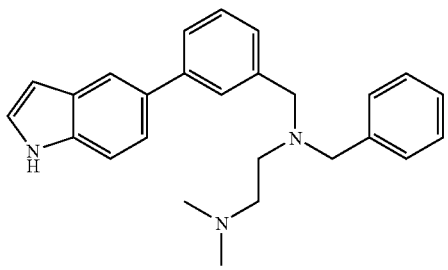

Step 1: 3-(1H-Indol-5-yl)-benzaldehyde: A mixture of 5-bromo-indole (8.7 g, 44.4 mmol), 3-formylbenzeneboronic acid (10 g, 66.7 mmol), cesium carbonate in water (2M, 88.8 mL, 178 mmol) in 450 mL of dioxane was degassed (evacuate in vacuo and pressurize with nitrogen, 3 times) $PdCl_2$(dppf).DCM (1.1 g, 1.3 mmol) was added and the mixture degassed one more time as described above. The resulting mixture was heated at 100° C. for 3 h, then it was allowed to cool to room temperature and partitioned between diethyl ether and water. The aqueous phase was extracted with diethyl ether and the combined organic phases were washed with water, brine, dried over $MgSO_4$, filtered and evaporated to give the crude product. Chromatography on silica gel (elution with ethyl acetate/heptane) afforded 5.6 g of the desired product.

Step 2: N-Benzyl-N-[3-(1H-indol-5-yl)-benzyl]-N',N'-dimethyl-ethane-1,2-diamine: Sodium triacetoxyborohydride (480 mg, 2.3 mmol) was added to a solution of 3-(1H-indol-5-yl)-benzaldehyde (250 mg, 1.1 mmol) and N'-benzyl-N,N-dimethyl-ethane-1,2-diamine (600 mg, 3.4 mmol) and acetic acid (204 mg, 3.4 mmol) in 8 mL of tetrahydrofuran. The mixture was stirred at ambient temperature overnight, and then it was diluted with ethyl acetate, and neutralized with the careful addition of saturated sodium bicarbonate solution. The layers were separated and the organic phase was treated with polystyrene supported isocyanate resin (1.49 mmol/g, 1.7 g) for 2 h. The mixture was filtered and the filtrate was washed with 1M sodium carbonate solution. The aqueous phase was extracted into ethyl acetate, and the combined organic phases were dried over magnesium sulfate, filtered and concentrated to leave 290 mg of the title compound. LC/MS (short method): retention time, 2.61 min; (M+H)=384.

$^1$H NMR (400 MHz, chloroform-D) δ ppm: 2.20 (s, 6H) 2.49-2.55 (m, 2H), 2.65-2.68 (m, 2H) 3.66 (s, 2H) 3.69 (s, 2H) 6.61 (br s, 1H) 7.21-7.26 (m, 3H) 7.28-7.34 (m, 3H) 7.35-7.41 (m, 3H) 7.45 (s, 2H) 7.52 (d, 1 H, J=7.6 Hz), 7.64 (s, 1H) 7.85 (s, 1H) 8.26 (s, 1H).

Examples 2 to 16

Example 1 was substantially repeated in Examples 2 to 16 with the exception of utilizing the respective starting materials and reagents in appropriate quantities in order to prepare the Examples 2 to 16 as tabulated in Table 1. Also summarized in Table 1 are the observed LC/MS data for Examples 2 to 16.

TABLE 1

| Example No. | Chemical Structure and Chemical Name | LC/MS Data RT (mins.) | M + H |
|---|---|---|---|
| 2 | 6-(3-{[Benzyl-(2-dimethylamino-ethyl)-amino]-methyl}-phenyl)-3H-benzothiazol-2-one hydrochloride. | 2.5$^a$ | 418 |
| 3 | 6-(3-{[Benzyl-(2-dimethylamino-ethyl)-amino]-methyl}-phenyl)-3H-benzooxazol-2-one hydrochloride. | 2.41$^a$ | 402 |

TABLE 1-continued

| Example No. | Chemical Structure and Chemical Name | LC/MS Data RT (mins.) | M + H |
|---|---|---|---|
| 4 | 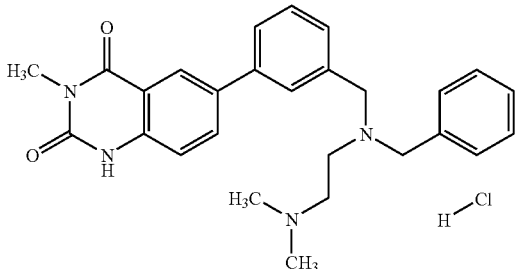<br>6-(3-{[Benzyl-(2-dimethylamino-ethyl)-amino]-methyl}-phenyl)-3-methyl-1H-quinazoline-2,4-dione hydrochloride. | 2.38$^a$ | 443 |
| 5 | 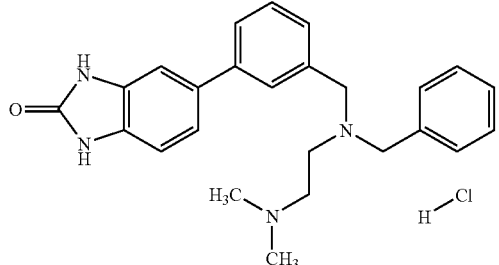<br>5-(3-{[Benzyl-(2-dimethylamino-ethyl)-amino]-methyl}-phenyl)-1,3-dihydro-benzoimidazol-2-one hydrochloride. | 2.23$^a$ | 401 |
| 6 | 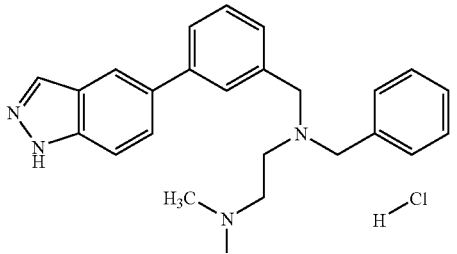<br>N-Benzyl-N-[3-(1H-indazol-5-yl)-benzyl]-N',N'-dimethyl-ethane-1,2-diamine hydrochloride. | 1.53$^a$ | 385 |
| 7 | 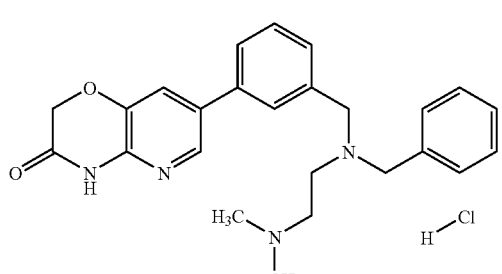<br>7-(3-{[Benzyl-(2-dimethylamino-ethyl)-amino]-methyl}-phenyl)-4H-pyrido[3,2-b][1,4]oxazin-3-one hydrochloride. | 1.47$^a$ | 417 |

TABLE 1-continued

| Example No. | Chemical Structure and Chemical Name | LC/MS Data RT (mins.) | M + H |
|---|---|---|---|
| 8 | 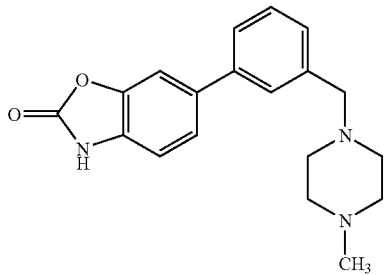<br>6-[3-(4-Methyl-piperazin-1-ylmethyl)-phenyl]-3H-benzooxazol-2-one | 1.75[a] | 324 |
| 9[c] | 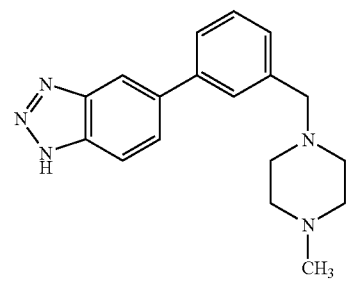<br>5-[3-(4-Methyl-piperazin-1-ylmethyl)-phenyl]-1H-benzotriazole | 1.64[a] | 308 |
| 10 | 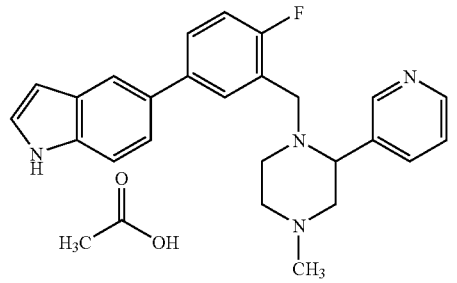<br>5-[4-Fluoro-3-(4-methyl-2-pyridin-3-yl-piperazin-1-ylmethyl)-phenyl]-1H-indole acetate | 2.17[a]<br>5.07[b] | 401 |
| 11 | Chiral<br>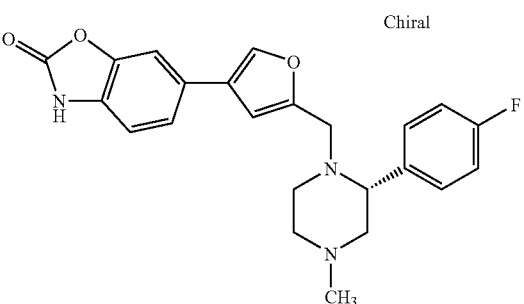<br>6-{5-[2R-(4-Fluoro-phenyl)-4-methyl-piperazin-1-ylmethyl]-furan-3-yl}-3H-benzooxazol-2-one. | 5.69[b] | 408 |

TABLE 1-continued

| Example No. | Chemical Structure and Chemical Name | LC/MS Data RT (mins.) | M + H |
|---|---|---|---|
| 12 | 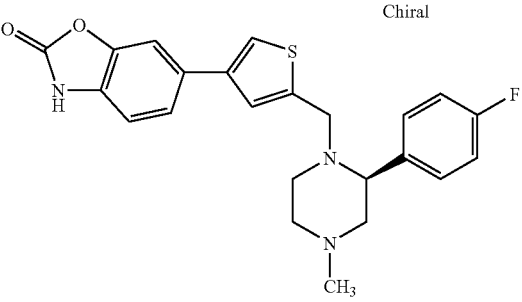 Chiral<br>6-{5-[2S-(4-Fluoro-phenyl)-4-methyl-piperazin-1-ylmethyl]-furan-3-yl}-3H-benzooxazol-2-one | 6.03[b] | 424 |
| 13 | 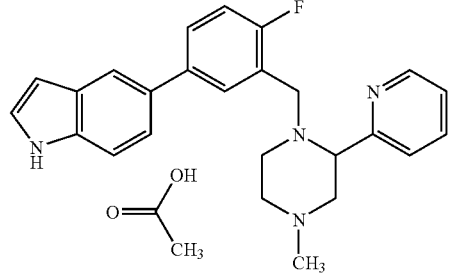<br>5-[4-Fluoro-3-(4-methyl-2-pyridin-2-yl-piperazin-1-ylmethyl)-phenyl]-1H-indole acetate. | 6.18[b] | 401 |
| 14 | 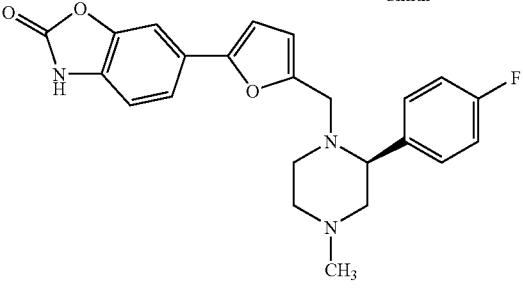 Chiral<br>6-{5-[2S-(4-Fluoro-phenyl)-4-methyl-piperazin-1-ylmethyl]-furan-3-yl}-3H-benzooxazol-2-one | 5.98[b] | 408 |
| 15 | 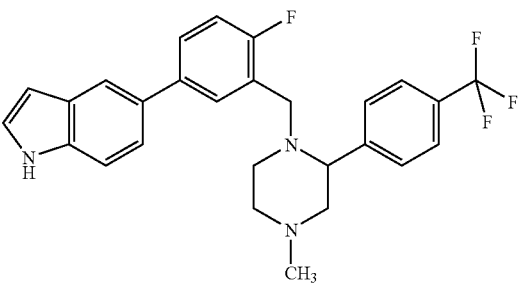<br>5-{4-Fluoro-3-[4-methyl-2-(4-trifluoromethyl-phenyl)-piperazin-1-ylmethyl]-phenyl}-1H-indole | 7.87[b] | 468 |

TABLE 1-continued

| Example No. | Chemical Structure and Chemical Name | LC/MS Data | |
|---|---|---|---|
| | | RT (mins.) | M + H |
| 16[d] | | 1.88[b] | 419 |

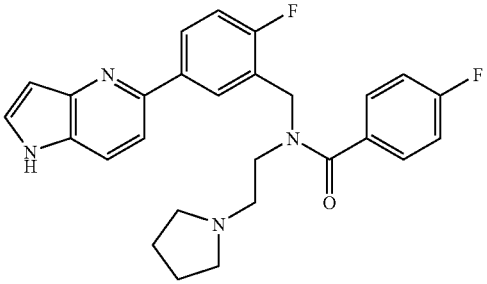

4-Fluoro-N-[2-fluoro-5-(1H-pyrrolo[3,2-b]pyridin-5-yl)-benzyl]-N-(2-pyrrolidin-1-yl-ethyl)-benzamide

[a]short LC/MS method;
[b]long LC/MS method;
[c]this Example 9 was synthesized following the procedures of Example 42;
[d]this Example 16 was synthesized following the procedures of Example 20;
n.a. - not available

Example 17

N-[3-(1H-Benzotriazol-5-yl)-benzyl]-N-benzyl-N',N'-dimethyl-propane-1,3-diamine

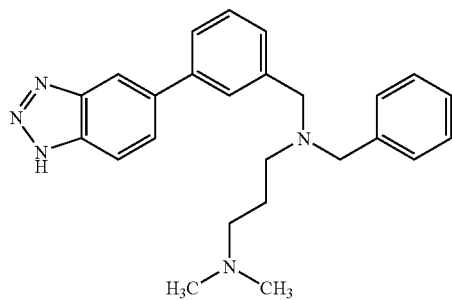

Step 1: N-Benzyl-N-(3-boranyl-benzyl)-N',N'-dimethyl-propane-1,2-diamine: Sodium triacetoxyborohydride (8.84 g, 14.0 mmol) and then 4.5 mL of acetic acid were added to a solution of 3-boranylbenzenecarboxaldehyde (2.0 g, 13.34 mmol) and N'-benzyl-N,N-dimethyl-ethane-1,2-diamine (2.5 g, 40.0 mmol) in 100 mL of 1,2-dichloroethane. The mixture was stirred at ambient temperature overnight, and then it was neutralized with the careful addition of saturated sodium bicarbonate solution. The layers were separated and the aqueous phase extracted into dichloromethane. The combined organic phases were dried over magnesium sulfate, filtered and concentrated to leave the crude product. Trituration with a mixture of diethyl ether and hexane gave 2.9 g of product. LC/MS: Retention time, 1.26 min; (M+H)=313.

Following the procedures as set forth above, N-benzyl-N-(3-boranyl-benzyl)-N',N'-dimethyl-propane-1,3-diamine was prepared starting from N'-benzyl-N,N-dimethyl-propane-1,3-diamine.

Step 2: N-Benzyl-N',N'-dimethyl-N-[3-(1-trityl-1H-benzotriazol-5-yl)-benzyl]-propane-1,3-diamine: A mixture of 5-bromo-1-trityl-1H-benzotriazole (220 mg, 0.5 mmol), N-benzyl-N-(3-boranyl-benzyl)-N',N'-dimethyl-propane-1,3-diamine (180 g, 0.55 mmol), and cesium carbonate solution in water (2M, 1 mL, 2 mmol) taken altogether in 10 mL of dioxane was degassed (evacuate in vacuo and pressurize with argon, two times) and PdCl$_2$(dppf).DCM (21 mg, 0.025 mmol) was added and the mixture was degassed two more times as described above. The resulting mixture was heated at 90° C. for 3 h, then it was allowed to cool to room temperature and the volatiles were removed in vacuo. The residue was partitioned between dichloromethane and water. The aqueous phase was extracted with dichloromethane and the combined organic phases were dried over MgSO$_4$, filtered and evaporated to give the crude product. Chromatography on silica gel (elution with methanol/dichloromethane) followed by trituration of the material obtained with diethyl ether gave 68 mg of the title compound.

Step 3: N-[3-(1H-Benzotriazol-5-yl)-benzyl]-N-benzyl-N',N'-dimethyl-propane-1,3-diamine: N-Benzyl-N',N'-dimethyl-N-[3-(1-trityl-1H-benzotriazol-5-yl)-benzyl]-propane-1,3-diamine (60 mg, 0.093 mmol) was dissolved in a mixture of 5 mL of ethanol, 5 mL of dioxane and 8 mL of 2M aqueous hydrochloric acid solution, and the resulting mixture was stirred at room temperature for 6 h. The volatiles were removed in vacuo and the residue partitioned between diethyl ether and 1M HCl solution. The aqueous phase was washed with diethyl ether and the combined organic phases were concentrated in vacuo to obtain the crude product, which was dissolved in small amount of 1M HCl solution and freeze dried. Purification by HPLC (elution with 30% acetonitrile/ 70% water (containing 0.1% trifluoroacetic acid)) afforded 30 mg of the title compound. LC/MS (short method): Retention time 1.19 min; (M+H)=400.

$^1$H NMR (400 MHz, methanol-$D_4$) δ ppm: 2.28-2.43 (m, 2H) 2.89 (s, 6H) 3.10-3.20 (m, 2H) 3.24-3.30 (m, 2H) 4.47-4.60 (m, 4H) 7.47-7.54 (m, 3H) 7.57-7.68 (m, 4H) 7.83-7.91 (m, 2H) 7.94-8.02 (m, 2H) 8.18 (s, 1H).

Examples 18 and 19

Example 17 was substantially repeated in Examples 18 and 19 with the exception of utilizing the respective starting materials and reagents in appropriate quantities in order to prepare the Examples 18 and 19 as tabulated in Table 2. Also summarized in Table 2 are the observed LC/MS data for Examples 18 and 19.

TABLE 2

| Example No. | Chemical Structure and Chemical Name | LC/MS Data RT (mins.) | M+H |
|---|---|---|---|
| 18 | N-[3-(1H-Benzoimidazol-5-yl)-benzyl]-N-benzyl-N',N'-dimethyl-ethane-1,2-diamine hydrochloride. | 1.26$^a$ | 385 |
| 19 | N-[3-(1H-Benzoimidazol-5-yl)-benzyl]-N-benzyl-N',N'-dimethyl-propane-1,3-diamine hydrochloride. | 1.01$^a$ | 399 |

$^a$short LC/MS method

Example 20

4-Fluoro-N-[2-fluoro-5-(1H-indol-5-yl)-benzyl]-N-(2-pyrrolidin-1-yl-ethyl)-benzamide

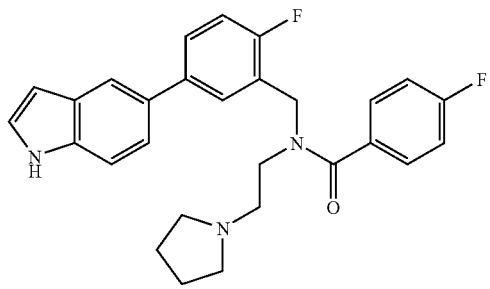

Step 1: [2-Fluoro-5-(1H-indol-5-yl)-benzyl]-(2-pyrrolidin-1-yl-ethyl)-amine. Sodium triacetoxyborohydride (530 g, 2.51 mmol) and then enough acetic acid to bring the pH to 5 were added to a solution of 5-(4-fluoro-3-formylphenyl)-1H-indole (200 mg, 0.84 mmol) and 1-(2-aminoethyl)pyrrolidine (191 mg, 1.67 mmol) in 15 mL of 1,2-dichloroethane. The mixture was stirred at ambient temperature overnight, and then it was diluted with dichloromethane, and neutralized with the careful addition of saturated sodium bicarbonate solution. The layers were separated and the aqueous phase extracted into dichloromethane. The combined organic phases were dried over magnesium sulfate, filtered and concentrated to leave the crude product. Chromatography (elution with methanol/dichloromethane) provided 90 mg of the title compound. LC/MS: Retention time, 0.34 min.

Step 2: 4-Fluoro-N-[2-fluoro-5-(1H-indol-5-yl)-benzyl]-N-(2-pyrrolidin-1-yl-ethyl)-benzamide: 4-Fluorobenzoyl chloride (93 mg, 0.59 mmol) was added to a solution of [2-fluoro-5-(1H-indol-5-yl)-benzyl]-(2-pyrrolidin-1-yl-ethyl)-amine (90 mg, 0.27 mmol) and triethyl amine (81 mg, 0.8 mmol) in 10 ml of dichloromethane at room temperature. The resulting mixture was stirred at ambient temperature for 2 h, and then the volatiles were removed in vacuo and the residue was dissolved in ethyl acetate and washed with 1 M HCl solution and water. The aqueous phase was extracted with ethyl acetate, and the combined organic phases were dried over magnesium sulfate, filtered and concentrated to leave the crude product. Chromatography (elution with methanol/dichloromethane) provided 181 mg of product. This was dissolved in dichloromethane and washed with saturated sodium bicarbonate solution. The organic phase was dried over magnesium sulfate, filtered and concentrated to afford 92 mg of the title compound. LC/MS: Retention time, 2.55 min; (M+H)=460.

$^1$H NMR (400 MHz, chloroform-D) δ ppm: 1.72 (br s, 1H) 2.16 (br s, 3H) 2.38 (br s, 1H) 2.63 (br s, 1H) 2.90-3.34 (m, 4H) 3.44 (br s, 1H) 3.86 (br s, 1H) 4.81 (br s, 2H) 6.56-6.67 (s, 1H) 7.11 (t, J=9.40 Hz, 3H) 7.30-7.43 (m, 3H) 7.46 (d, J=9.40 Hz, 1H) 7.49-7.69 (m, 3H) 7.77 (s, 1H) 8.37 (s, 1H).

Examples 21 to 41

Example 20 was substantially repeated in Examples 21 to 41 with the exception of utilizing the respective starting materials and reagents in appropriate quantities in order to prepare the Examples 21 to 41 as tabulated in Table 3. Also summarized in Table 3 are the observed LC/MS data for Examples 21 to 41.

TABLE 3

| Example No. | Chemical Structure and Chemical Name | LC/MS Data RT (mins.) | M + H |
|---|---|---|---|
| 21 | 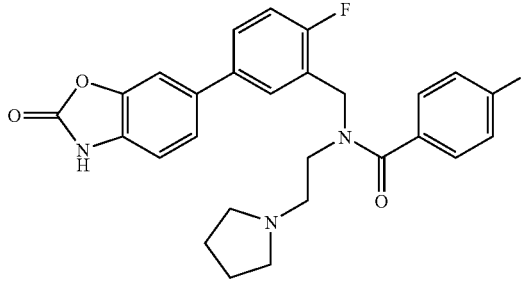<br>4-Fluoro-N-[2-fluoro-5-(2-oxo-2,3-dihydro-benzooxazol-6-yl)-benzyl]-N-(2-pyrrolidin-1-yl-ethyl)-benzamide | 2.43[a] | 478 |
| 22[c] | 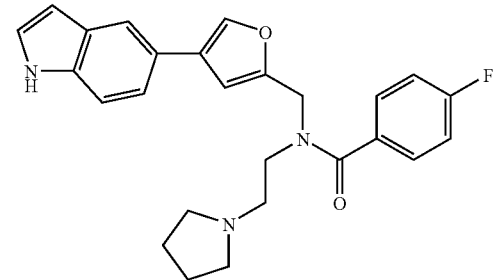<br>4-Fluoro-N-[4-(1H-indol-5-yl)-furan-2-ylmethyl]-N-(2-pyrrolidin-1-yl-ethyl)-benzamide | 5.45[b] | 432 |
| 23 | 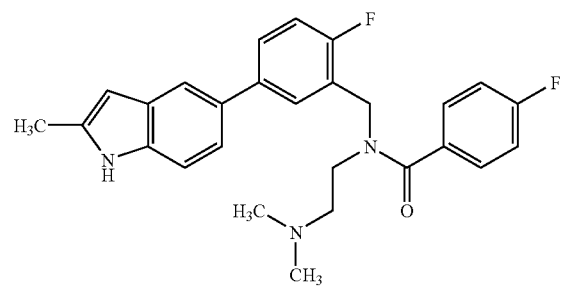<br>N-(2-Dimethylamino-ethyl)-4-fluoro-N-[2-fluoro-5-(2-methyl-1H-indol-5-yl)-benzyl]-benzamide | 6.69[b] | 448 |
| 24 | 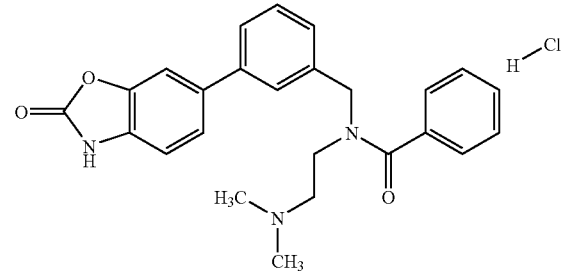<br>N-(2-Dimethylamino-ethyl)-N-[3-(2-oxo-2,3-dihydro-benzooxazol-6-yl)-benzyl]-benzamide hydrochloride. | 2.18[a] | 416 |

TABLE 3-continued

| Example No. | Chemical Structure and Chemical Name | LC/MS Data RT (mins.) | M + H |
|---|---|---|---|
| 25 | 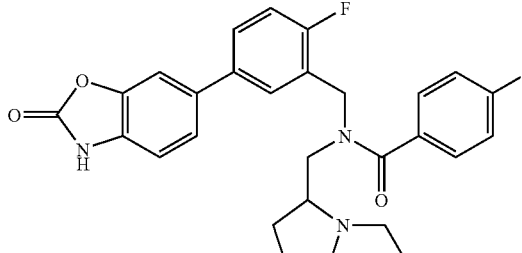<br>N-(1-Ethyl-pyrrolidin-2-ylmethyl)-4-fluoro-N-[2-fluoro-5-(2-oxo-2,3-dihydro-benzooxazol-6-yl)-benzyl]-benzamide. | 2.47$^a$ | 492 |
| 26 | 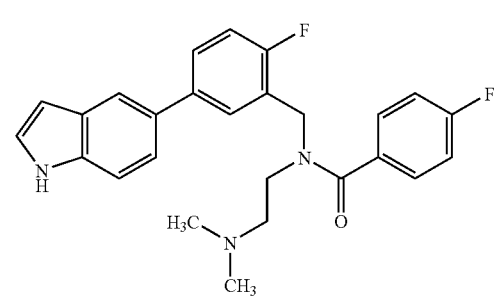<br>N-(2-Dimethylamino-ethyl)-4-fluoro-N-[2-fluoro-5-(1H-indol-5-yl)-benzyl]-benzamide. | 6.5$^b$ | 434 |
| 27 | 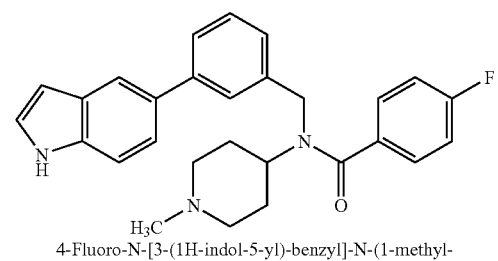<br>4-Fluoro-N-[3-(1H-indol-5-yl)-benzyl]-N-(1-methyl-piperidin-4-yl)-benzamide. | 2.5$^a$ | 442 |
| 28 | 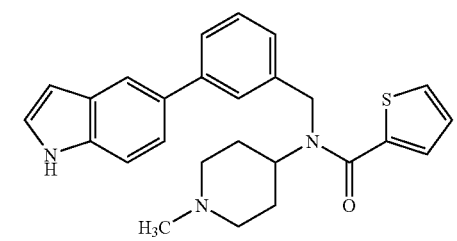<br>Thiophene-2-carboxylic acid [3-(1H-indol-5-yl)-benzyl]-(1-methyl-piperidin-4-yl)-amide. | 2.46$^a$ | 430 |
| 29 | 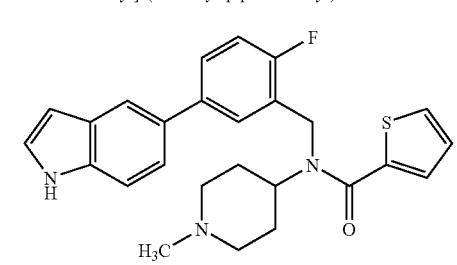<br>Thiophene-2-carboxylic acid [2-fluoro-5-(1H-indol-5-yl)-benzyl]-(1-methyl-piperidin-4-yl)-amide. | 5.17$^b$ | 448 |

TABLE 3-continued

| Example No. | Chemical Structure and Chemical Name | LC/MS Data RT (mins.) | M + H |
|---|---|---|---|
| 30 | 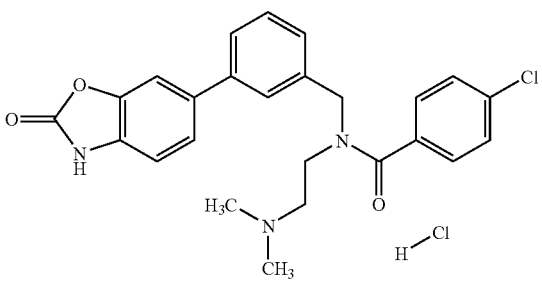 4-Chloro-N-(2-dimethylamino-ethyl)-N-[3-(2-oxo-2,3-dihydro-benzooxazol-6-yl)-benzyl]-benzamide hydrochloride. | 2.37[a] | 450 |
| 31[c] | 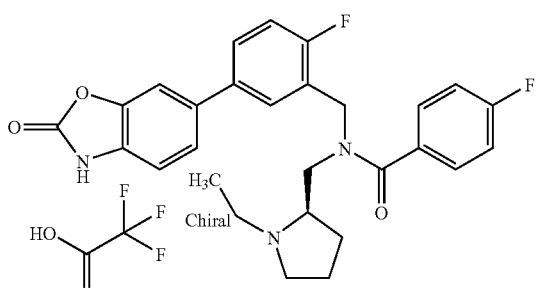 N-(1-Ethyl-pyrrolidin-2R-ylmethyl)-4-fluoro-N-[2-fluoro-5-(2-oxo-2,3-dihydro-benzooxazol-6-yl)-benzyl]-benzamide trifluoro-acetate. | 2.29[a] | 492 |
| 32 | 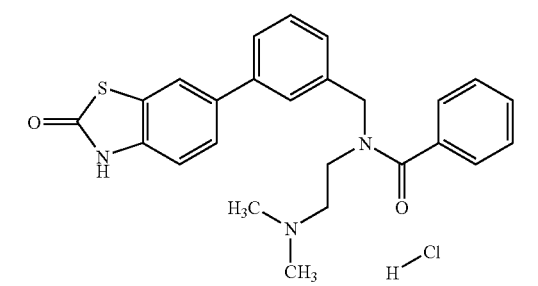 N-(2-Dimethylamino-ethyl)-N-[3-(2-oxo-2,3-dihydro-benzothiazol-6-yl)-benzyl]-benzamide hydrochloride. | 2.27[a] | 432 |
| 33 | 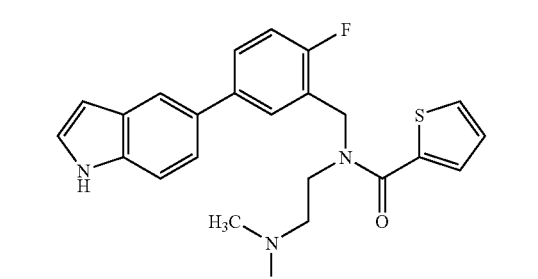 Thiophene-2-carboxylic acid (2-dimethylamino-ethyl)-[2-fluoro-5-(1H-indol-5-yl)-benzyl]-amide | 5.29[b] | 422 |

TABLE 3-continued

| Example No. | Chemical Structure and Chemical Name | LC/MS Data RT (mins.) | M + H |
|---|---|---|---|
| 34 | 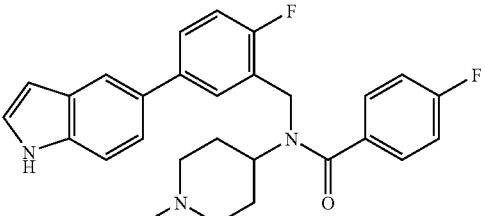<br>4-Fluoro-N-[2-fluoro-5-(1H-indol-5-yl)-benzyl]-N-(1-methyl-piperidin-4-yl)-benzamide | 6.23[b] | 460 |
| 35 | 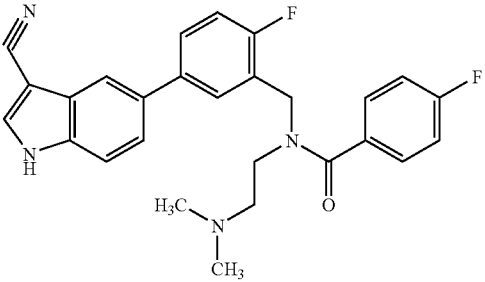<br>N-[5-(3-Cyano-1H-indol-5-yl)-2-fluoro-benzyl]-N-(2-dimethylamino-ethyl)-4-fluoro-benzamide | 5.4[b] | 459 |
| 36 | 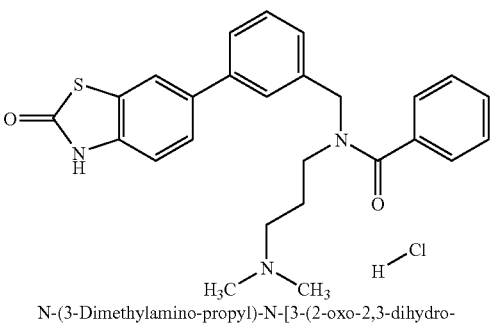<br>N-(3-Dimethylamino-propyl)-N-[3-(2-oxo-2,3-dihydro-benzothiazol-6-yl)-benzyl]-benzamide; hydrochloride | 1.48[a] | 446 |
| 37 | 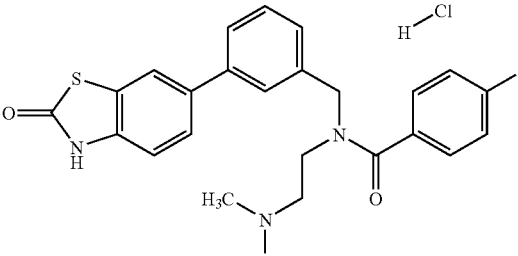<br>4-Chloro-N-(2-dimethylamino-ethyl)-N-[3-(2-oxo-2,3-dihydro-benzothiazol-6-yl)-benzyl]-benzamide hydrochloride. | 2.43[a] | 466 |

TABLE 3-continued

| Example No. | Chemical Structure and Chemical Name | LC/MS Data RT (mins.) | M + H |
|---|---|---|---|
| 38 | 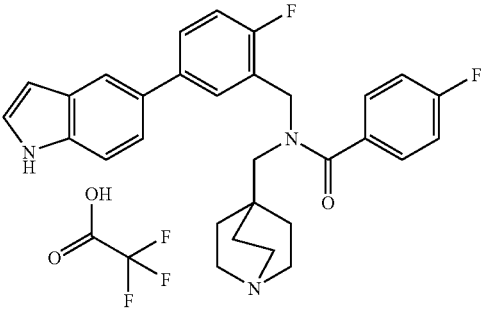<br>N-(1-Aza-bicyclo[2.2.2]oct-4-ylmethyl)-4-fluoro-N-[2-fluoro-5-(1H-indol-5-yl)-benzyl]-benzamide trifluoroacetate | 5.75[b] | 486 |
| 39 | 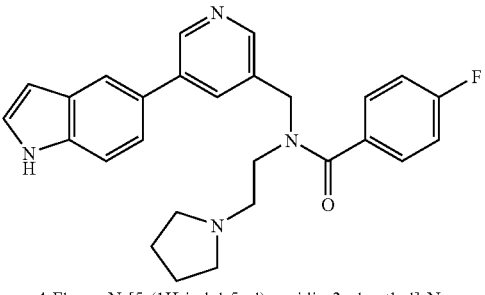<br>4-Fluoro-N-[5-(1H-indol-5-yl)-pyridin-3-ylmethyl]-N-(2-pyrrolidin-1-yl-ethyl)-benzamide. | 4.28[b] | 443 |
| 40 | 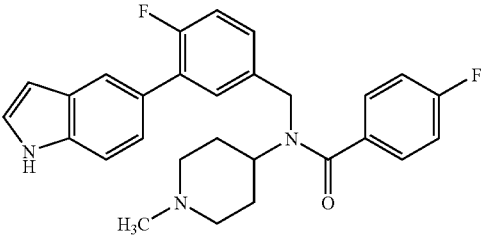<br>4-Fluoro-N-[4-fluoro-3-(1H-indol-5-yl)-benzyl]-N-(1-methyl-piperidin-4-yl)-benzamide | 6.29[b] | 460 |
| 41 | 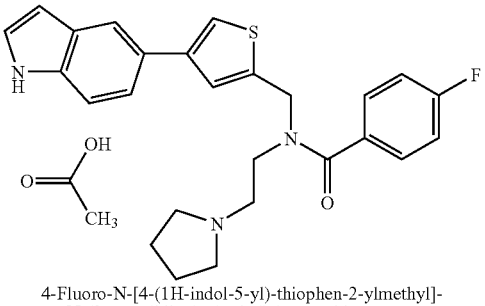<br>4-Fluoro-N-[4-(1H-indol-5-yl)-thiophen-2-ylmethyl]-N-(2-pyrrolidin-1-yl-ethyl)-benzamide acetate. | 6.53[b] | 448 |

[a]short LC/MS method;
[b]long LC/MS method;
[c]this Example was synthesized following the procedures of Example 104.

Example 42

{4-Fluoro-3-[2S-(4-fluoro-phenyl)-piperazin-1-ylmethyl]-phenyl}-1H-indazole

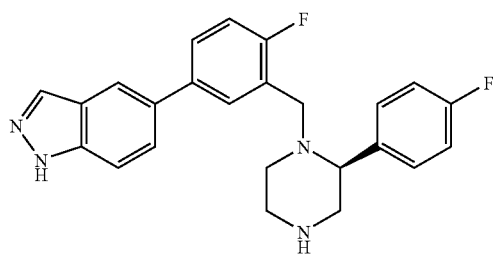

Step 1: 2S-(4-Fluorophenyl)-piperazine: A solution of ethylene diamine (7.4 g, 123.5 mmol) in ethanol (100 mL) was added dropwise over 15 minutes to a stirring solution of 4-fluoroglyoxal (21.0 g, 123.5 mmol) in ethanol (300 mL) and the reaction was left for 4 hours. Sodium borohydride (23.5 g, 622 mmol) was added and the mixture was stirred overnight at room temperature. Water (200 mL) was added and the mixture was stirred for 1 hour after which the majority of the ethanol was removed in vacuo. The concentrated solution was extracted with DCM (4×100 mL) and the combined extracts were combined, washed with brine and dried over $Na_2SO_4$. The solvent was removed in vacuo to yield a pale yellow solid (19.0 g, 86%). 8.8 g of this material was dissolved in methanol (60 mL) and added to a solution of N-acetyl-L-leucine (16.5 g, 95.2 mmol) in methanol (100 mL). Ethyl acetate (550 mL) was added and the mixture was left at room temperature overnight. The precipitate was filtered and dried to give a solid (9.0 g) which was taken up in 4M NaOH aq. (100 mL) and extracted with DCM (4×100 mL). The combined extracts were combined, washed with brine and the solvent was removed in vacuo to yield a solid (3.1 g). This solid was re-crystallized from EtOAc to yield 2.23 g of the S enantiomer (the title compound). The enantiomeric excess was determined by chiral chromatography employing the following chiral chromatographic conditions: Column: Phenomenex Chirex (S)-ICR 250×4.6 mm; solvent: n-heptane:ethanol [80:20]+0.3% TFA; L=254 nm, flow rate=1 mL/min, UV sensitivity=0.1 AUF; ~1 mg of compound in 1 mL of n-heptane:ethanol [75:25] using authentic chiral compounds and racemate as reference.

Step 2: 3S-(4-Fluorophenyl)-piperazine-1-carboxylic acid tert-butyl ester: 2S-(4-Fluorophenyl)-piperazine (3.75 g, 20.83 mmol) was dissolved in dichloromethane and cooled to 0° C. A solution of di-tert-butyl-dicarbonate (4.77 g, 21.87 mmol) in 10 mL of dichloromethane was added and the reaction was left at 0° C. for one hour. The solvent was removed in vacuo to yield a crystalline white solid (5.85 g).

Step 3: 5-Bromo-indazole-1-carboxylic acid tert-butyl ester: Di-tert-butyldicarbonate (11.4 g, 52.21 mmol), triethylamine (6.27 g, 62.16 mmol) and 4-(N,N-dimethylaminopyridine (304 mg, 2.49 mmol) were added sequentially to a solution of 5-bromoindazole (9.8 g, 49.73 mmol) in tetrahydrofuran at room temperature. The mixture was stirred at room temperature for 71.5 h and then it was heated at reflux for 16 h. The volatiles were removed in vacuo and the residue was dissolved in dichloromethane and washed with brine, dried over magnesium sulfate, filtered and concentrated to leave the crude product. Chromatography (elution with diethyl ether/heptane) gave 13.98 g of the title compound. LC: Retention time, 3.93 min.

Step 4: 5-(4-Fluoro-3-formylphenyl)-indazole-1-carboxylic acid tert-butyl ester: A mixture of 5-bromo-indazole-1-carboxylic acid tert-butyl ester (3.37 mmol), 2-fluoro-4-(4,4,5,5-tetramethyl-[1,3]dioxoboran-2-yl)-benzaldehyde (1.01 g, 4.04 mmol)) $PdCl_2$(dppf).DCM (27 mg, 0.03 mmol) in 16 mL of dioxane was degassed (evacuate in vacuo and pressurize with argon, three times); cesium carbonate in water (2M, 6.73 mL, 13.46 mmol) was added and the mixture degassed three more times as described above. The resulting mixture was heated at 85° C. for 6 h, then it was allowed to cool to room temperature and left overnight. The mixture was diluted with dichloromethane and washed with brine. The aqueous phase was extracted with dichloromethane and the combined organic phases were washed with brine, dried over $MgSO_4$, filtered and evaporated to give crude product. Chromatography on silica gel (elution with diethyl ether/heptane) gave 820 mg of the title compound.

Step 5: 5-{4-Fluoro-3-[2S-(4-fluoro-phenyl)-piperazin-1-ylmethyl]-phenyl}-1H-indazole: 3S-(4-Fluorophenyl)-piperazine-1-carboxylic acid tert-butyl ester (150 mg, 0.54 mmol) and 5-(4-fluoro-3-formylphenyl)-indazole-1-carboxylic acid tert-butyl ester (210 mg, 0.62 mmol) was dissolved in DCE (5 mL) and glacial acetic acid was added (32 mg, 0.54 mmol) followed by sodium tris-acetoxyborohyduide (341 mg, 1.6 mmol). The reaction was stirred overnight at room temperature. Dichloromethane was added and the mixture was washed with water and brine and dried over $Na_2SO_4$. The solvent was removed in vacuo to give the crude product. Chromatography (elution with methanol/dichloromethane) provided 200 mg of product. This was treated with 15 mL of 95% aqueous TFA for 1.5 h. The volatiles were removed in vacuo and residue triturated with diethyl ether (3×) leaving 70 mg of product. LC/MS (long run): Retention time, 6.14 min; (M+H)=405.

$^1$H NMR (400 MHz, methanol-$D_4$) δ ppm: 2.57 (td, J=12.64, 2.64 Hz, 1H) 3.09-3.36 (m, 5H) 3.41 (d, J=13.6 Hz, 1H) 3.67 (dd, J=11.43, 3.08 Hz, 1H) 3.77 (d, J=13.6 Hz, 1H) 7.10-7.21 (m, 3H) 7.53-7.62 (m, 6H) 7.94 (t, J=1.32 Hz, 1H) 8.11 (s, 1H).

Examples 43 to 52

Example 42 was substantially repeated in Examples 43 to 52 with the exception of utilizing the respective starting materials and reagents in appropriate quantities in order to prepare the Examples 43 to 52 as tabulated in Table 4. Also summarized in Table 4 are the observed LC/MS data for Examples 43 to 52.

TABLE 4

| Example No. | Chemical Structure and Chemical Name | LC/MS Data RT (mins.) | M + H |
|---|---|---|---|
| 43 | 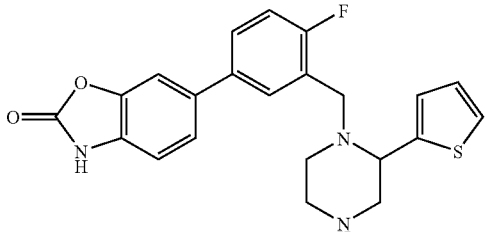<br>6-[4-Fluoro-3-(2-thiophen-2-yl-piperazin-1-ylmethyl)-phenyl]-3H-benzooxazol-2-one | 5.04[b] | 410 |
| 44 | 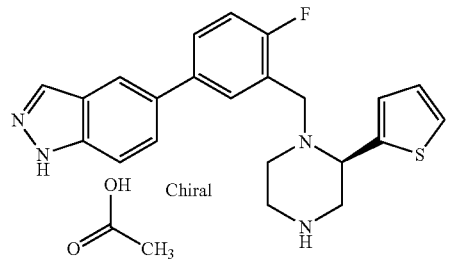<br>5-[4-Fluoro-3-(2S-thiophen-2-yl-piperazin-1-ylmethyl)-phenyl]-1H-indazole acetate | 5.19[b] | 393 |
| 45 | 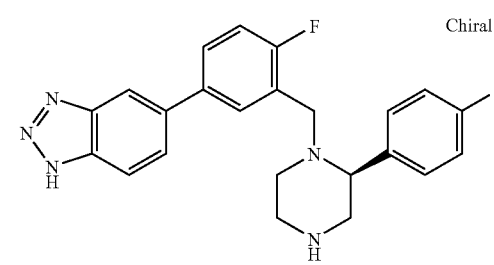<br>5-{4-Fluoro-3-[2S-(4-fluoro-phenyl)-piperazin-1-ylmethyl]-phenyl}-1H-benzotriazole | 5.05[b] | 406 |
| 46 | 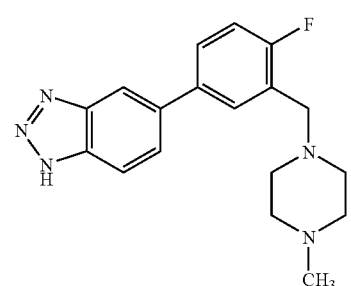<br>5-[4-Fluoro-3-(4-methyl-piperazin-1-ylmethyl)-phenyl]-1H-benzotriazole | 1.88[a] | 326 |
| 47 | 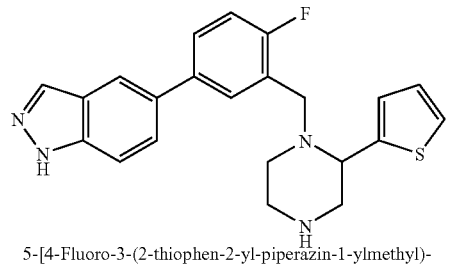<br>5-[4-Fluoro-3-(2-thiophen-2-yl-piperazin-1-ylmethyl)-phenyl]-1H-indazole | 5.86[b] | 393 |

TABLE 4-continued

| Example No. | Chemical Structure and Chemical Name | LC/MS Data RT (mins.) | M + H |
|---|---|---|---|
| 48[c] | 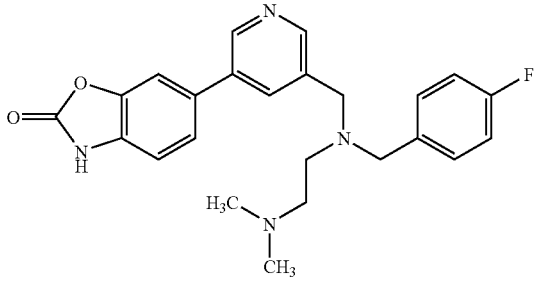<br>6-(5-{[(2-Dimethylamino-ethyl)-(4-fluoro-benzyl)-amino]-methyl}-pyridin-3-yl)-3H-benzooxazol-2-one | 4.02[b] | 421 |
| 49[c] | 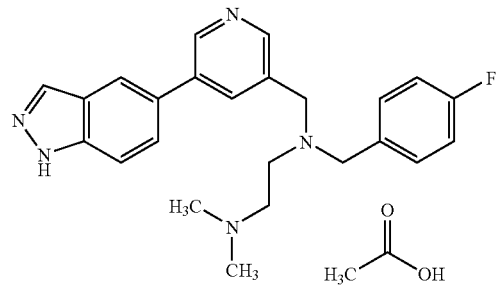<br>N-(4-Fluoro-benzyl)-N-[5-(1H-indazol-5-yl)-pyridin-3-ylmethyl]-N′,N′-dimethyl-ethane-1,2-diamine acetate | 3.72[b] | 404.2 |
| 50[c] | 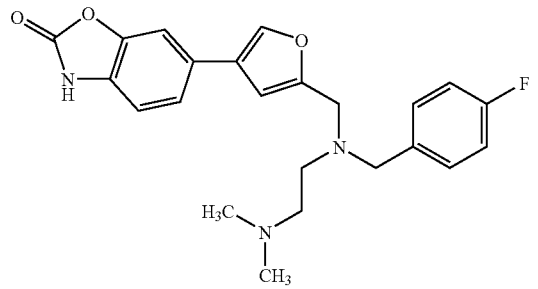<br>6-(5-{[(2-Dimethylamino-ethyl)-(4-fluoro-benzyl)-amino]-methyl}-furan-3-yl)-3H-benzooxazol-2-one | 5.16[b] | 410 |
| 51 | 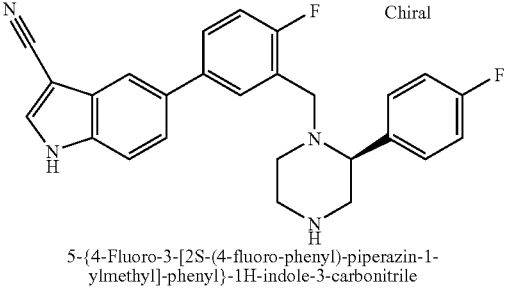<br>5-{4-Fluoro-3-[2S-(4-fluoro-phenyl)-piperazin-1-ylmethyl]-phenyl}-1H-indole-3-carbonitrile | 6.03[b] | 429 |

TABLE 4-continued

| | | LC/MS Data | |
|---|---|---|---|
| Example No. | Chemical Structure and Chemical Name | RT (mins.) | M + H |
| 52 | 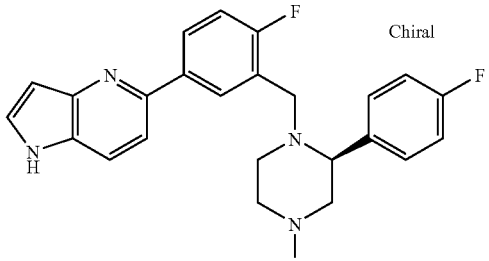5-{4-Fluoro-3-[2-(4-fluoro-phenyl)-4-methyl-piperazin-1-ylmethyl]-phenyl}-1H-pyrrolo[3,2-b]pyridine | 4.49[b] | 419 |

[a]short LC/MS method;
[b]long LC/MS method;
[c]prepared as in Example 113, Step 1.

Example 53

N-[5-(1H-Benzotriazol-5-yl)-2-fluoro-benzyl]-N-(1-ethyl-pyrrolidin-2S-ylmethyl)-4-fluoro-benzamide

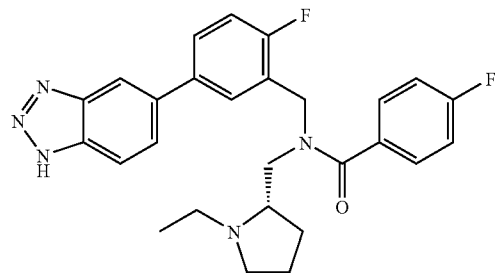

Step 1: (1-Ethyl-pyrrolidin-2S-ylmethyl)-[2-fluoro-5-(1-trityl-1H-benzotriazol-5-yl)-benzyl]-amine: A mixture of 2-fluoro-5-(1-trityl-1H-benzotriazol-5-yl)-benzaldehyde (368 mg, 0.76 mmol), (S)-(+)-1-ethyl-2-aminomethylpyrrolidine (120 mg, 0.83 mmol) and molecular sieves in 10 mL of methanol was stirred at ambient temperature for 3 h. The mixture was cooled to −78° C., and sodium borohydride (72 mg, 1.9 mmol) was added and the mixture was allowed to warm to room temperature and stirred overnight. The volatiles were removed in vacuo and the residue was diluted with dichloromethane and washed with water. The aqueous phase extracted with dichloromethane, and the combined organic phases were washed with brine, dried over magnesium sulfate, filtered and concentrated to leave the crude product. Chromatography (elution with methanol/dichloromethane) gave 255 mg of product.

Step 2: N-(1-Ethyl-pyrrolidin-2S-ylmethyl)-4-fluoro-N-[2-fluoro-5-(1-trityl-1H-benzotriazol-5-yl)-benzyl]-benzamide. HATU (122 mg, 0.32 mmol) was added to a solution of (1-ethyl-pyrrolidin-2-ylmethyl)-[2-fluoro-5-(1-trityl-1H-benzotriazol-5-yl)-benzyl]-amine (127 mg, 0.21 mmol), 4-fluorobenzoic acid (45 mg, 0.32 mmol) and diisopropylethylamine (82 mg, 0.64 mmol) in 1 mL of dimethylformamide, and the resulting mixture stirred at ambient temperature overnight. The mixture was diluted with dichloromethane, and washed with saturated sodium bicarbonate solution and brine, dried over magnesium sulfate, filtered and concentrated to leave the crude product. Chromatography (elution with methanol/dichloromethane) provided 98 mg of product.

LC/MS: Retention time, 3.39 min; (M+H)=718.

Step 3: N-[5-(1H-Benzotriazol-5-yl)-2-fluoro-benzyl]-N-(1-ethyl-pyrrolidin-2S-ylmethyl)-4-fluoro-benzamide: N-(1-Ethyl-pyrrolidin-2-ylmethyl)-4-fluoro-N-[2-fluoro-5-(1-trityl-1H-benzotriazol-5-yl)-benzyl]-benzamide (143 mg, 0.2 mmol) in 4 mL of methanol and 2 mL of 4M HCl in dioxane was stirred at room temperature for 24 h. The solvent was removed in vacuo and the residue purified by HPLC. The material obtained was treated with hydrochloric acid to leave 100 mg of the title compound. LC/MS (long run): Retention time, 5.64 min; (M+H)=476.

$^1$H NMR (400 MHz, methanol-$D_4$) δ ppm: 1.29-1.46 (m, 3H) 1.86-1.99 (m, 1H) 2.04-2.19 (m, 2H) 2.31 (ddd, J=13.19, 7.03 Hz, 1H) 3.08-3.28 (m, 2H) 3.48 (br s, 1H) 3.68-3.78 (m, 2H) 3.85 (dd, J=14.73, 5.49 Hz, 1H) 4.02 (dd, J=14.73, 5.49 Hz 1H) 4.76-4.95 (m, 2H) 7.18-7.32 (m, 3H) 7.51-7.64 (m, 3H) 7.71-7.79 (m, 2H) 7.98 (d, J=8.57 Hz, 1H) 8.06 (s, 1H).

Examples 54 to 65

Example 53 was substantially repeated in Examples 54 to 65 with the exception of utilizing the respective starting materials and reagents in appropriate quantities in order to prepare the Examples 54 to 65 as tabulated in Table 5. Also summarized in Table 5 are the observed LC/MS data for Examples 54 to 65.

TABLE 5

| Example No. | Chemical Structure and Chemical Name | LC/MS Data | |
|---|---|---|---|
| | | RT (mins.) | M + H |
| 54 | 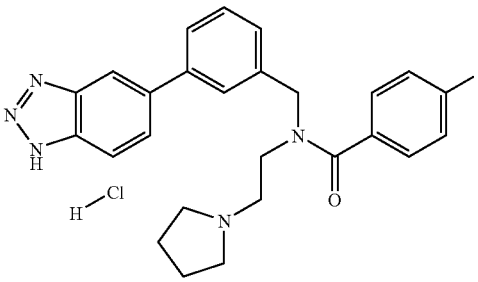<br>N-[3-(1H-Benzotriazol-5-yl)-benzyl]-4-fluoro-N-(2-pyrrolidin-1-yl-ethyl)-benzamide hydrochloride | 5.26[b] | 444 |
| 55 | 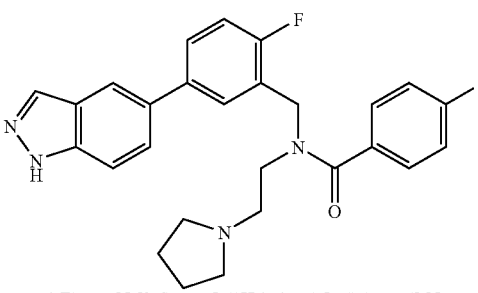<br>4-Fluoro-N-[2-fluoro-5-(1H-indazol-5-yl)-benzyl]-N-(2-pyrrolidin-1-yl-ethyl)-benzamide | 4.82[b] | 461 |
| 56 | 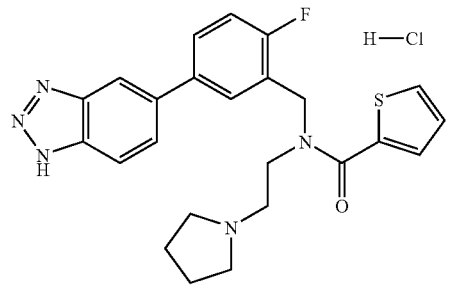<br>Thiophene-2-carboxylic acid [5-(1H-benzotriazol-5-yl)-2-fluoro-benzyl]-(2-pyrrolidin-1-yl-ethyl)-amide hydrochloride | 5.22[b] | 450 |
| 57 | 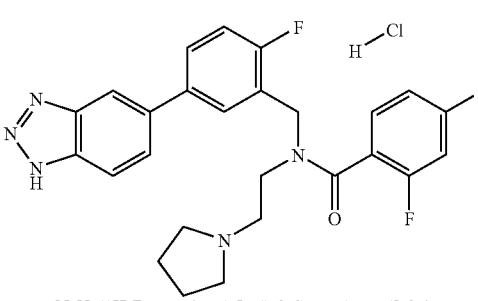<br>N-[5-(1H-Benzotriazol-5-yl)-2-fluoro-benzyl]-2,4-difluoro-N-(2-pyrrolidin-1-yl-ethyl)-benzamide hydrochloride | 5.53[b] | 480 |

TABLE 5-continued

| Example No. | Chemical Structure and Chemical Name | LC/MS Data | |
| --- | --- | --- | --- |
| | | RT (mins.) | M + H |
| 58 | 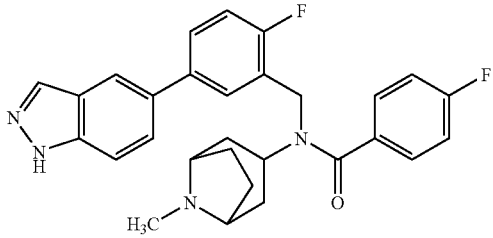

4-Fluoro-N-[2-fluoro-5-(1H-indazol-5-yl)-benzyl]-N-(endo-8-methyl-8-aza-bicyclo[3.2.1]oct-3-yl)-benzamide | 5.09[b] | 487 |
| 59 | 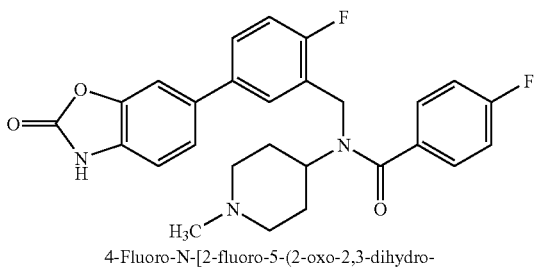

4-Fluoro-N-[2-fluoro-5-(2-oxo-2,3-dihydro-benzooxazol-6-yl)-benzyl]-N-(1-methyl-piperidin-4-yl)-benzamide | 4.79[b] | 478 |
| 60 | 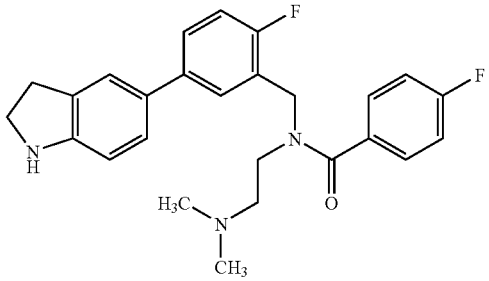

N-[5-(2,3-Dihydro-1H-indol-5-yl)-2-fluoro-benzyl]-N-(2-dimethylamino-ethyl)-4-fluoro-benzamide | 3.91[b] | 436 |
| 61 | 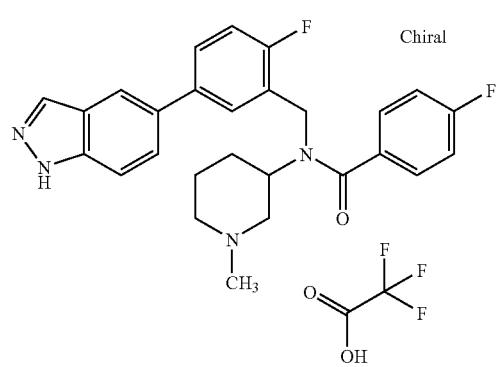

4-Fluoro-N-[2-fluoro-5-(1H-indazol-5-yl)-benzyl]-N-(1-methyl-piperidin-3S-yl)-benzamide trifluoro-acetate | 4.99[b] | 461 |

TABLE 5-continued

| Example No. | Chemical Structure and Chemical Name | LC/MS Data RT (mins.) | M + H |
|---|---|---|---|
| 62 | 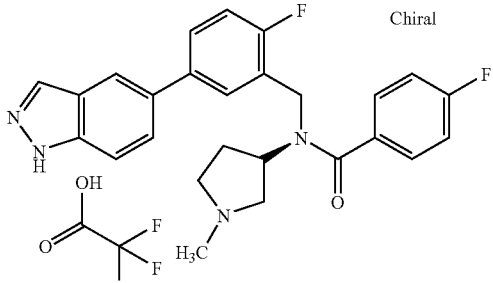 Chiral<br>4-Fluoro-N-[2-fluoro-5-(1H-indazol-5-yl)-benzyl]-N-(1-methyl-pyrrolidin-3R-yl)-benzamide trifluoro-acetate | 4.42[b] | 447 |
| 63 | 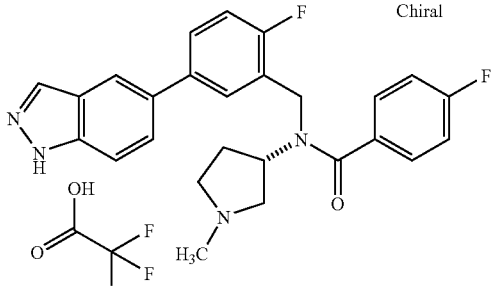 Chiral<br>4-Fluoro-N-[2-fluoro-5-(1H-indazol-5-yl)-benzyl]-N-(1-methyl-pyrrolidin-3S-yl)-benzamide trifluoro-acetate | 4.35[b] | 447 |
| 64 | 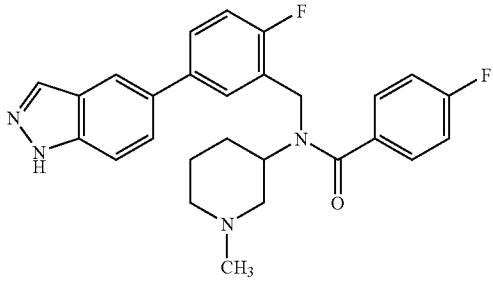<br>4-Fluoro-N-[2-fluoro-5-(1H-indazol-5-yl)-benzyl]-N-(1-methyl-piperidin-3-yl)-benzamide | 4.91[b] | 461 |
| 65 | 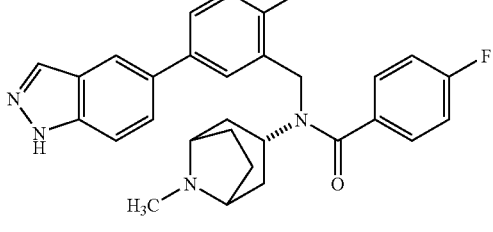 Chiral<br>4-Fluoro-N-[2-fluoro-5-(1H-indazol-5-yl)-benzyl]-N-(exo-8-methyl-8-aza-bicyclo[3.2.1]oct-3-yl)-benzamide | 5.22[b] | 487 |

[a]long LC/MS method

Example 66

N-[5-(1H-Benzothiazol-5-yl)-2-fluoro-benzyl]-4-fluoro-N-piperidin-4-yl-benzamide

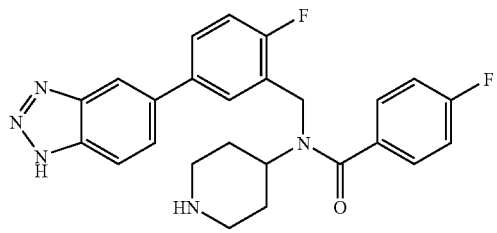

Step 1: 4-Oxo-piperidine-1-carboxylic acid-2-trimethylsilanyl-ethyl ester: Carbonic acid 4-nitro-phenyl ester-2-trimethylsilanyl-ethyl ester (8.33 g, 29.3 mmol), triethylamine (12.3 g, 122 mmol) and DMAP (3.6 g, 29.5 mmol) were added to a room temperature solution of 4-piperidone hydrochloride (4.52 g, 33.4 mmol) in 100 mL of acetonitrile. The resulting mixture was heated at reflux for 2 h, then cooled and the volatiles were removed in vacuo. The residue was dissolved in dichloromethane, washed with water and 1M NaOH solution, and concentrated in vacuo to leave 6.3 g of product.

Step 2: 4-Amino-piperidine-1-carboxylic acid 2-trimethylsilanyl-ethyl ester: A slurry of 10% palladium on carbon (200 mg) in water was added to 4-oxo-piperidine-1-carboxylic acid-2-trimethylsilanyl-ethyl ester (2.42 g, 10 mmol) in 100 mL of methanol. Ammonium formate (6.0 g, 95 mmol) in water was added dropwise, and the mixture stirred vigorously overnight. The mixture was filtered and the filtrate concentrated in vacuo to leave the crude product. Chromatography (elution with methanol-dichloromethane) provided 0.98 g of product.

Step 3: 4-[2-Fluoro-5-(1-trityl-1H-benzotriazol-5-yl)-benzylamino]-piperidine-1-carboxylic acid 2-trimethylsilany-1-ethyl ester: Sodium triacetoxyborohydride (890 mg, 4.2 mmol) and acetic acid (126 mg, 4.2 mmol) were added to a solution of 5-(4-fluoro-3-formylphenyl)-1-trityl-1H-benzotriazole (1.0 mg, 2.1 mmol) and 4-amino-piperidine-1-carboxylic acid 2-trimethylsilanyl-ethyl ester (760 mg, 3.1 mmol) in dichloroethane. The mixture was stirred at ambient temperature overnight, and then it was diluted with dichloromethane, and neutralized with careful addition of 1 M sodium carbonate solution. The layers were separated and the aqueous phase extracted with dichloromethane. The combined organic phases were washed with brine, dried over magnesium sulfate, filtered and concentrated to leave the crude product. Chromatography provided 980 mg of product. LC/MS: Retention time, 3.27 and 3.34 min; (M+H)=712.

Step 4: 4-{(4-Fluoro-benzoyl)-[2-fluoro-5-(1-trityl-1H-benzotriazol-5-yl)-benzyl]-amino}-piperidine-1-carboxylic acid 2-trimethylsilanyl-ethyl ester: HATU was added to a solution of 4-[2-fluoro-5-(1-trityl-1H-benzotriazol-5-yl)-benzylamino]-piperidine-1-carboxylic acid 2-trimethylsilany-1-ethyl ester, 4-fluorobenzoic acid and diisopropylethylamine and the resulting mixture stirred at ambient temperature overnight. The mixture was diluted with ethyl acetate washed with 1 M sodium carbonate solution. The layers were separated and the aqueous phase extracted with ethyl acetate. The combined organic phases were washed with brine, dried over magnesium sulfate, filtered and concentrated to leave the crude product. Chromatography (elution with diethyl ether/hexane, followed by ethyl acetate/hexane) provided 740 mg of product.

Step 5: N-[5-(1H-Benzotriazol-5-yl)-2-fluoro-benzyl]-4-fluoro-N-piperidin-4-yl-benzamide and 4-Fluoro-N-[2-fluoro-5-(1-trityl-1H-benzotriazol-5-yl)-benzyl]-N-piperidin-4-yl-benzamide: Tetrabutylammonium fluoride (1M in THF, 2.6 mL, 2.6 mmol) was added to a mixture of 4-{(4-fluoro-benzoyl)-[2-fluoro-5-(1-trityl-1H-benzotriazol-5-yl)-benzyl]-amino}-piperidine-1-carboxylic acid 2-trimethylsilanyl-ethyl ester (730 mg, 0.88 mmol) and 4 angstrom molecular sieves in 5 mL of THF. After 3 h the mixture was filtered and the solvent was removed in vacuo. The residue was eluted through an SCX cation exchange column (elution with dichloromethane, followed by 1-2% ammonia in methanol) to give a mixture of products. Chromatography (elution with methanol/dichloromethane, followed by methanol/dichloromethane with a small amount of 1-2% ammonia in methanol) gave 110 mg of 4-fluoro-N-[2-fluoro-5-(1-trityl-1H-benzotriazol-5-yl)-benzyl]-N-piperidin-4-yl-benzamide (LC/MS: Retention time, 3.03 min; (M+H)=690) and 170 mg of N-[5-(1H-benzotriazol-5-yl)-2-fluoro-benzyl]-4-fluoro-N-piperidin-4-yl-benzamide (LCMS: Retention time, 2.22 min; (M+H)=448).

$^1$H NMR (400 MHz, methanol-D$_4$) δ ppm: 1.72-2.11 (m, 5H) 2.36-2.73 (m, 2H) 3.03-3.24 (m, 2H) 3.82-4.17 (m, 1H) 4.74-4.84 (m, 1H) 7.12-7.29 (m, 3H) 7.47-7.56 (m, 2H) 7.58-7.69 (m, 8H) 7.93 (d, 1H, J=8.6 Hz) 7.98 (s, 1H).

Example 67

N-[5-(1H-Benzotriazol-5-yl)-2-fluoro-benzyl]-4-fluoro-N-(1-isopropyl-piperidin-4-yl)-benzamide

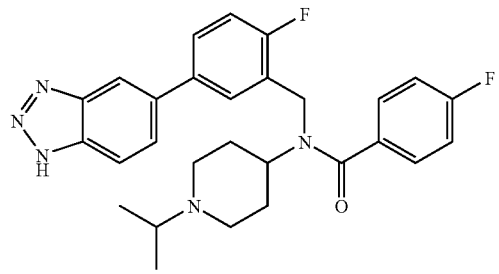

Step 1: 4-Fluoro-N-[2-fluoro-5-(1-trityl-1H-benzotriazol-5-yl)-benzyl]-N-(1-isopropyl-piperidin-4-yl)-benzamide: A mixture of 4-Fluoro-N-[2-fluoro-5-(1-trityl-1H-benzotriazol-5-yl)-benzyl]-N-piperidin-4-yl-benzamide (25 mg, 0.04 mmol), isopropyl iodide (34 mg, 0.2 mmol) and potassium carbonate (28 mg, 0.2 mmol) in 2 mL of DMF was heated at 40° C. for 3 h when additional isopropyl iodide (34 mg, 0.2 mmol) was added. The mixture was heated for an additional 2 h and then left at ambient temperature for 10 days. The mixture was diluted with water and the product extracted into ethyl acetate. The combined organic phases were dried over magnesium sulfate, filtered and concentrated to leave the crude product. Chromatography (elution with methanol/dichloromethane) provided 18 mg of product.

Step 2: N-[5-(1H-Benzotriazol-5-yl)-2-fluoro-benzyl]-4-fluoro-N-(1-isopropyl-piperidin-4-yl)-benzamide: Trifluoroacetic acid (TFA, 0.25 mL) was added to a solution of 4-fluoro-N-[2-fluoro-5-(1-trityl-1H-benzotriazol-5-yl)-benzyl]-N-(1-isopropyl-piperidin-4-yl)-benzamide (18 mg, 0.024 mmol) in 1 mL of dichloromethane and the resulting mixture stirred at ambient temperature for 3 h, when an additional 0.5 mL of TFA was added. This was stirred overnight and then the mixture was neutralized by the careful addition of 1M sodium carbonate. The layers were separated, the aqueous phase was extracted with dichloromethane, and the combined organic phases were dried over magnesium sulfate, filtered, and the volatiles were removed in vacuo to leave the crude product. Chromatography (elution with methanol/dichloromethane) provided 6.5 mg of product. LC/MS: Retention time, 2.25 min; (M+H)=490.

Example 68

N-[5-(1H-Benzotriazol-5-yl)-2-fluoro-benzyl]-N-(1-cyclopropyl-piperidin-4-yl)-4-fluoro-benzamide

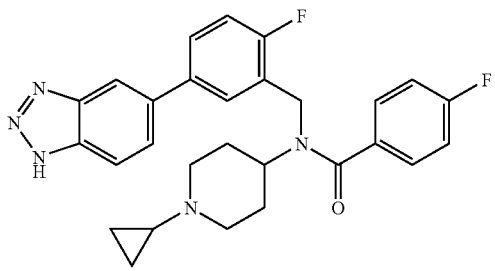

Step 1: N-(1-Cyclopropyl-piperidin-4-yl)-4-fluoro-N-[2-fluoro-5-(1-trityl-1H-benzotriazol-5-yl)-benzyl]-benzamide. Solid supported cyanoborohydride (2.5 mmol/g, 46 mg) was added to a solution of 4-fluoro-N-[2-fluoro-5-(1-trityl-1H-benzotriazol-5-yl)-benzyl]-N-piperidin-4-yl-benzamide (20 mg, 0.029 mmol), (1-ethoxy-cyclopropoxy)-trimethylsilane (25 mg, 0.145 mmol) and acetic acid (1.74 mg, 0.029 mmol) in 1 mL of methanol. The mixture was stirred at 45° C. for 2 h and then at 75° C. overnight. The mixture was cooled and filtered and the filtrate concentrated in vacuo to provide the crude product. Chromatography provided 14 mg of product. LC/MS: Retention time, 3.20 min; (M+H)=730.

Step 2: N-[5-(1H-Benzotriazol-5-yl)-2-fluoro-benzyl]-N-(1-cyclopropyl-piperidin-4-yl)-4-fluoro-benzamide. Trifluoroacetic acid (TFA, 1 mL) was added to a solution of N-(1-cyclopropyl-piperidin-4-yl)-4-fluoro-N-[2-fluoro-5-(1-trityl-1H-benzotriazol-5-yl)-benzyl]-benzamide (14 mg, 0.019 mmol) in 1 mL of dichloromethane and the resulting mixture stirred at ambient temperature overnight and then the mixture was neutralized by careful addition of 1M sodium carbonate. The layers were separated, the aqueous phase was extracted with dichloromethane, and the combined organic phases were dried over magnesium sulfate, filtered, and the volatiles were removed in vacuo to leave the crude product. Chromatography (elution with methanol/dichloromethane) provided 9 mg of the title compound. LC/MS: Retention time, 2.22 min; (M+H)=488.

$^1$H NMR (400 MHz, chloroform-D) δ ppm: 0.17-0.48 (m, 4H) 1.31-2.10 (m, 8H) 2.97 (br s, 2H) 4.74 (br s, 2H) 7.01 (br s, 3H) 7.31-7.60 (m, 5H) 7.71-8.03 (m, 2H).

Example 69

N-[5-(1H-Benzotriazol-5-yl)-2-fluoro-benzyl]-N-(1-methyl-piperidin-4-yl)-4-fluoro-benzamide

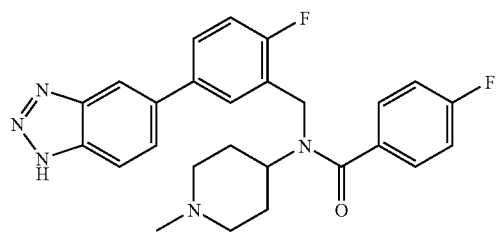

Sodium triacetoxyborohydride (8.5 mg, 0.04 mmol) was added to a mixture of 4-fluoro-N-[2-fluoro-5-(1-trityl-1H-benzotriazol-5-yl)-benzyl]-N-piperidin-4-yl-benzamide (25 mg, 0.04 mmol), formaldehyde (37% aqueous solution, 15 µL, 0.18 mmol) and acetic acid (2.4 mg, 0.04 mmol) in 1 mL of methanol. The mixture was stirred at ambient temperature overnight, and then it was diluted with dichloromethane, and neutralized with the careful addition of 1 M sodium carbonate solution. The layers were separated and the aqueous phase was extracted with dichloromethane. The combined organic phases were washed with brine, dried over magnesium sulfate, filtered and concentrated to leave the crude product. Chromatography provided 15 mg of product. Trifluoroacetic acid (TFA, 0.5 mL) was added to a solution of the material obtained above in 1 mL of dichloromethane and the resulting mixture stirred at ambient temperature for 5 h, and then the mixture was neutralized by the careful addition of 1M sodium carbonate. The layers were separated, the aqueous phase was extracted with dichloromethane, and the combined organic phases were dried over magnesium sulfate, filtered, and the volatiles were removed in vacuo to leave the crude product. Chromatography provided 6.5 mg of product. LC/MS: Retention time, 2.20 min; (M+H)=462.

$^1$H NMR (400 MHz, chloroform-D) δ ppm: 1.54-2.09 (m, 7H) 2.26 (s, 3H) 2.93 (br s, 2H) 4.82 (br s, 2H) 7.00 (br s, 3H) 7.38-7.54 (m, 4H) 7.59 (br s, 1H) 7.86 (d, J=8.57 Hz, 2H) 7.92 (s, 1H).

Example 70

(4-Fluoro-benzyl)-[2-fluoro-5-(1H-indol-5-yl)-benzyl]-(1-methyl-piperidin-4-yl)-amine

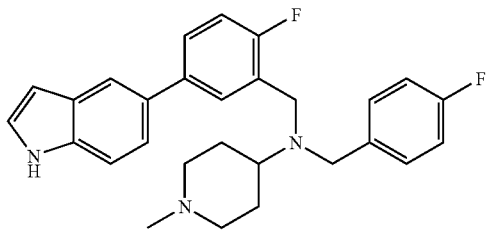

Step 1: [2-Fluoro-5-(1H-indol-5-yl)-benzyl]-(1-methyl-piperidin-4-yl)-amine. Sodium triacetoxyborohydride (400 mg, 1.88 mmol) and then enough acetic acid to bring the pH to 5 were added to a solution of 5-(4-fluoro-3-formylphenyl)-1H-indole (150 mg, 0.63 mmol) and 1-methyl-piperidin-4- ylamine (144 mg, 1.23 mmol) in 15 mL of 1,2-dichloroethane. The mixture was stirred at ambient temperature overnight, and then it was diluted with dichloromethane and washed with water. The aqueous phase extracted with dichloromethane, and the combined organic phases were dried over magnesium sulfate, filtered and concentrated to leave the crude product, which was eluted through an SCX cation exchange column (elution with methanol, followed by 2M ammonia in methanol) to give 250 mg of product.

Step 2: (4-Fluoro-benzyl)-[2-fluoro-5-(1H-indol-5-yl)-benzyl]-(1-methyl-piperidin-4-yl)-amine: Sodium triacetoxyborohydride (470 mg, 2.23 mmol) and then enough acetic acid to bring the pH to 5 were added to a solution of [2-fluoro-5-(1H-indol-5-yl)-benzyl]-(1-methyl-piperidin-4-yl)-amine (250 mg, 0.74 mmol) and 4-fluorobenzaldehyde (183 mg, 1.48 mmol) in 15 mL of 1,2-dichloroethane. The mixture was stirred at ambient temperature overnight, and then it was diluted with dichloromethane, and neutralized with the careful addition of saturated sodium bicarbonate solution. The organic phase was separated and dried over magnesium sulfate, filtered and concentrated to leave the crude product. Chromatography (elution with methanol/ethyl acetate) provided 232 mg of product. LC/MS (long run): Retention time, 6.12 min; (M+H)=446.

$^1$H NMR (400 MHz, chloroform-D) δ ppm: 1.73-1.84 (m, 4H) 1.90 (t, J=11.2 Hz, 2H) 2.23 (s, 3H) 2.46-2.60 (m, 1H) 2.92 (d, 2H) 3.66 (s, 2H) 3.72 (s, 2H) 6.59 (s, 1H) 6.93 (t, J=8.74 Hz, 2H) 7.00 (dd, J=9.78, 8.46 Hz, 1H) 7.22-7.26 (m, 1H) 7.27-7.34 (m, 3H) 7.37-7.46 (m, 2H) 7.66 (dd, J=7.14, 2.31 Hz, 1H) 7.72 (s, 1H) 8.22 (s, 1H).

Examples 71 to 73

Example 70 was substantially repeated in Examples 71 to 73 with the exception of utilizing the respective starting materials and reagents in appropriate quantities in order to prepare the Examples 71 to 73 as tabulated in Table 6. Also summarized in Table 6 are the observed LC/MS data for Examples 71 to 73.

TABLE 6

| Example No. | Chemical Structure and Chemical Name | LC/MS Data | |
|---|---|---|---|
| | | RT (mins.) | M + H |
| 71 | <br>6-(3-{[(1-Ethyl-pyrrolidin-2R-ylmethyl)-(4-fluoro-benzyl)-amino]-methyl}-4-fluoro-phenyl)-3H-benzooxazol-2-one trifluoro-acetate | 2.62$^a$ | 478 |
| 72 | 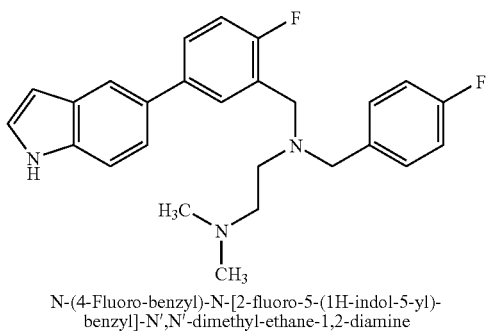<br>N-(4-Fluoro-benzyl)-N-[2-fluoro-5-(1H-indol-5-yl)-benzyl]-N',N'-dimethyl-ethane-1,2-diamine | 7.12$^b$ | 420 |

TABLE 6-continued

| Example No. | Chemical Structure and Chemical Name | LC/MS Data RT (mins.) | M + H |
|---|---|---|---|
| 73 | 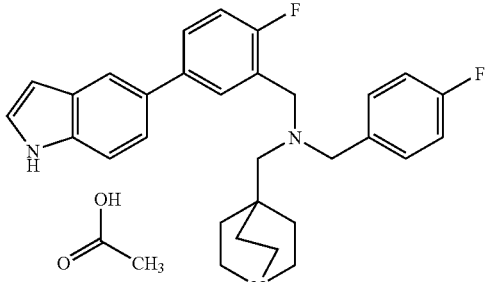<br>(1-Aza-bicyclo[2.2.2]oct-4-ylmethyl)-(4-fluoro-benzyl)-[2-fluoro-5-(1H-indol-5-yl)-benzyl]-amine acetate | 6.53[b] | 472 |

[a] short LC/MS method;
[b] long LC/MS method

Example 74

N-(2-Dimethylamino-ethyl)-4-fluoro-N-[5-(1H-indol-5-yl)-pyridin-3-ylmethyl]-benzamide trifluoroacetate

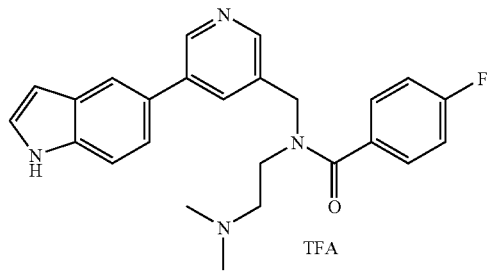

Step 1: 5-(1H-Indol-5-yl)-pyridine-3-carbaldehyde: Indole-5-boronic acid (1 g 6.25 mmol), 5-bromopyridine-3-carboxaldehyde (1.3 g, 6.9 mmol) and $PdCl_2$(dppf).DCM (2.2 g, 2.7 mmol) and 15 ml of dioxane were evenly distributed amongst five 5 mL microwave vessels (Smith Personal Chemistry). The mixtures were degassed (evacuate in vacuo and pressurize with nitrogen). Sodium carbonate in water (2M, 9.38 mL, 18.7 mmol) was evenly distributed amongst the reaction vessels and the mixtures degassed two more times as described above. The mixture was heated to 100° C. for 12 min in a Smith synthesizer. The samples were cooled, combined and washed with water. The aqueous phase was extracted with dichloromethane and the combined organic phases were dried over $MgSO_4$, filtered and evaporated to give crude product. Chromatography (elution with ethyl acetate/cyclohexane) provided 870 mg of product.

Step 2: N'-[5-(1H-Indol-5-yl)-pyridin-3-ylmethyl]-N,N-dimethyl-ethane-1,2-diamine: Sodium triacetoxyborohydride (855 mg, 4.05 mmol) and then enough acetic acid to bring the pH to 5 were added to a solution of 5-(1H-indol-5-yl)-pyridine-3-carbaldehyde (300 mg, 1.35 mmol) and N,N-dimethylethylene diamine (237 mg, 2.7 mmol) in 15 mL of 1,2-dichloroethane. The mixture was stirred at ambient temperature for 48 h, and then the volatiles were removed in the presence of celite. The product was eluted from the celite through silica gel (elution with methanol/dichloromethane) to give 328 mg of product. LC/MS: Retention time, 0.43 min; (M+H)=295.19.

Step 3: N-(2-Dimethylamino-ethyl)-4-fluoro-N-[5-(1H-indol-5-yl)-pyridin-3-ylmethyl]-benzamide: 4-Fluorobenzoyl chloride (111 mg, 0.7 mmol) was added to a solution of N'-[5-(1H-indol-5-yl)-pyridin-3-ylmethyl]-N,N-dimethyl-ethane-1,2-diamine (160 mg, 0.54 mmol) and triethyl amine (109 mg, 1.08 mmol) in 15 mL of dichloromethane at room temperature. The resulting mixture was stirred at ambient temperature overnight, and then a further 111 mg of 4-fluorobenzoyl chloride was added and the mixture stirred for an additional 2 h. The volatiles were removed in vacuo to leave the crude product. Chromatography (elution with methanol/dichloromethane) provided 231 mg of material. This was dissolved in dichloromethane and washed with 1M sodium hydroxide solution. The organic phase was dried over magnesium sulfate, filtered and concentrated to leave material which was further purified by HPLC (elution with acetonitrile/water/TFA) to give 21 mg of product. LC/MS (long run): Retention time, 3.85 min; (M+H)=417.

Example 75 and 76

Example 74 was substantially repeated in Examples 75 and 76 with the exception of utilizing the respective starting materials and reagents in appropriate quantities in order to prepare the Examples 75 and 76 as tabulated in Table 7. Also summarized in Table 7 are the observed LC/MS data for Examples 75 and 76.

TABLE 7

| Example No. | Chemical Structure and Chemical Name | LC/MS Data RT (mins.) | M + H |
|---|---|---|---|
| 75 | 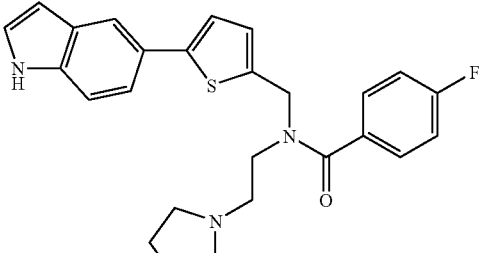<br>4-Fluoro-N-[5-(1H-indol-5-yl)-thiophen-2-ylmethyl]-N-(2-pyrrolidin-1-yl-ethyl)-benzamide | 5.06[b] | 448 |
| 76 | 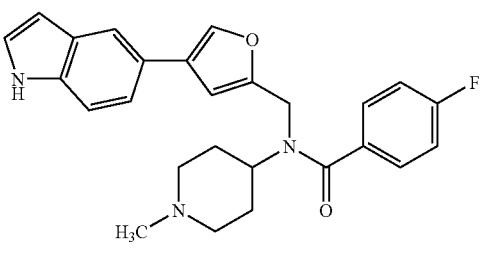<br>4-Fluoro-N-[4-(1H-indol-5-yl)-furan-2-ylmethyl]-N-(1-methyl-piperidin-4-yl)-benzamide | 5.33[b] | 432 |

[b]long LC/MS method

Example 77

N-(1-Aza-bicyclo[2.2.2]oct-3R-yl)-4-fluoro-N-[2-fluoro-5-(1H-indol-6-yl)-benzyl]-benzamide

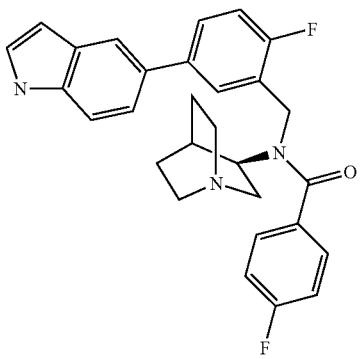

Step 1: (R)-N-(1-Aza-bicyclo[2.2.2]oct-3R-yl)-N-(5-bromo-2-fluoro-benzyl)amine: Sodium triacetoxyborohydride (1.6 g, 7.53 mmol) and enough acetic acid to bring the pH to 5 were added to a solution of 5-bromo-2-fluorobenzaldehyde (510 mg, 2.51 mmol), (R)-(−)-1-aza-bicyclo[2.2.2]oct-3R-ylamine (1.0 g, 5.02 mmol) and triethylamine (508 mg, 5.02 mmol) in 8 mL of 1,2-dichloroethane. The mixture was stirred at ambient temperature for 4.5 h, and then it was quenched by the careful addition of 1 M sodium hydroxide solution. The aqueous phase was extracted with ethyl acetate, and the combined organic phases were dried over magnesium sulfate, filtered and concentrated to leave 816 mg of product.

Step 2: (R)-N-(1-Aza-bicyclo[2.2.2]oct-3R-yl)-N-(5-bromo-2-fluoro-benzyl)-4-fluoro-benzamide: 4-Fluorobenzoyl chloride (597 mg, 3.77 mmol) was added to a solution of the material obtained above in 10 mL of pyridine at ambient temperature. The mixture was stirred at room temperature and then 1 M sodium hydroxide solution was added, and the product extracted into ethyl acetate, and the volatiles were removed in vacuo to leave a mixture of starting material and product. This was treated again with 4-fluorobenzoyl chloride (597 mg, 3.77 mmol) in 10 mL of pyridine at ambient temperature. 1 M sodium hydroxide solution was added, and the product extracted into ethyl acetate, and the volatiles were removed in vacuo to leave the crude product. Chromatography (elution with triethylamine/methanol/ethyl acetate) gave 508 mg of product. LC/MS (short run): Retention time, 2.26 min; (M+H)=435/437.

Step 3: N-(1-Aza-bicyclo[2.2.2]oct-3R-yl)-4-fluoro-N-[2-fluoro-5-(1H-indol-6-yl)-benzyl]-benzamide: A mixture of (R)-N-(1-Aza-bicyclo[2.2.2]oct-3R-yl)-N-(5-bromo-2-fluoro-benzyl)-4-fluoro-benzamide (150 mg, 0.345 mmol), 5-indoleboronic acid (83 mg, 0.517 mmol), sodium carbonate in water (2M, 0.69 mL, 1.38 mmol) in 2 mL of dioxane was degassed (evacuate in vacuo and pressurize with nitrogen, four times) PdCl$_2$(dppf).DCM (12 mg, 0.0017 mmol) was added and the mixture degassed four times as described above. The resulting mixture was heated at 80° C. overnight, then it was allowed to cool to room temperature, filtered and the filtrate diluted with dichloromethane and washed with water. The aqueous phases were extracted with dichloromethane and the combined organic phases were dried over MgSO$_4$, filtered and evaporated to give crude product. Chromatography on silica gel (elution with methanol/dichloromethane) afforded 20 mg of the product. LC/MS (short run): Retention time, 2.63 min; (M+H)=472.

¹H NMR (400 MHz, chloroform-D) δ ppm: 1.50-1.76 (m, 2H) 1.98 (br s, 1H) 2.13 (br s, 1H) 2.71-3.00 (m, 4H) 3.02-3.24 (m, 2H) 3.38 (br s, 1H) 4.21 (br s, 1H) 4.76-4.93 (m, 1H) 6.62 (br s, 1H) 7.01-7.12 (m, 3H) 7.26-7.29 (m, 1H) 7.33 (d, 1H, J=8.4 Hz) 7.36-7.54 (m, 5H) 7.75 (br s, 1H).

Examples 78 and 79

Example 77 was substantially repeated in Examples 78 and 79 with the exception of utilizing the respective starting materials and reagents in appropriate quantities in order to prepare the Examples 78 and 79 as tabulated in Table 8. Also summarized in Table 8 are the observed LC/MS data for Examples 78 and 79.

TABLE 8

| Example No. | Chemical Structure and Chemical Name | RT (mins.) | M+H |
|---|---|---|---|
| 78 | 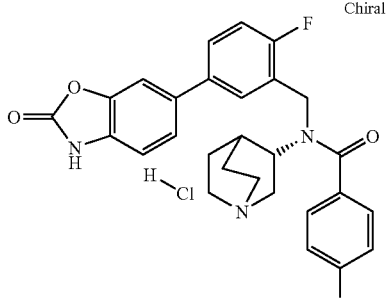<br>N-(1-Aza-bicyclo[2.2.2]oct-3S-yl)-4-fluoro-N-[2-fluoro-5-(2-oxo-2,3-dihydro-benzooxazol-6-yl)-benzyl]-benzamide hydrochloride | 2.35ᵃ | 490 |
| 79 | 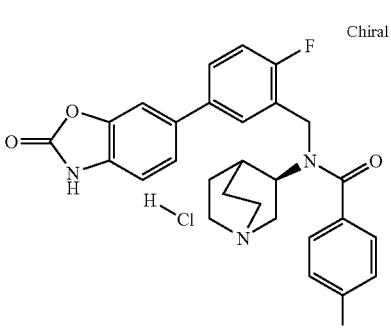<br>N-(1-Aza-bicyclo[2.2.2]oct-3R-yl)-4-fluoro-N-[2-fluoro-5-(2-oxo-2,3-dihydro-benzooxazol-6-yl)-benzyl]-benzamide hydrochloride | 2.37ᵃ | 490 |

ᵃshort LC/MS method

Example 80

[5-(1H-Benzothiazol-5-yl)-2-fluoro-benzyl]-(4-fluoro-benzyl)-pyrrolidin-2R-ylmethyl-amine trihydrochloride

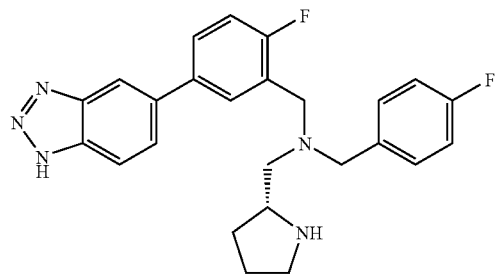

Step 1: (R)-2-[(4-Fluoro-benzylamino)-methyl]-pyrrolidine-1-carboxylic acid tert-butyl ester: Sodium triacetoxyborohydride (15.9 g, 75.4 mmol) and enough acetic acid to bring the pH to 5 were added to a solution of N-tert-butoxycarbonyl-L-prolinal (5 g, 25 mmol) and 4-fluorobenzylamine (6.28 g, 50.3 mmol) in 200 mL of 1,2-dichloroethane. The mixture was stirred at ambient temperature overnight, and then it was diluted with dichloromethane, and washed with saturated sodium bicarbonate solution. The organic phase was dried over magnesium sulfate, filtered and concentrated to leave the crude product. Chromatography (elution with methanol/ethyl acetate) afforded 6.0 g of product.

Step 2: (R)-2-({(4-Fluoro-benzyl)-[2-fluoro-5-(1-trityl-1H-benzotriazol-5-yl)-benzyl]-amino}-methyl)-pyrrolidine-1-carboxylic acid tert-butyl ester: Sodium triacetoxyborohydride (159 mg, 0.75 mmol) and acetic acid (36 mg, 0.6 mmol) were added to a mixture of 5-(4-fluoro-3-formylphenyl)-1-trityl-1H-benzotriazole (145 mg, 0.3 mmol) and (R)-2-[(4-fluoro-benzylamino)-methyl]-pyrrolidine-1-carboxylic acid tert-butyl ester (111 mg, 0.36 mmol) and 4 angstrom molecular sieves in 5 mL of dichloroethane. The mixture was stirred at ambient temperature overnight, and then it was diluted with dichloromethane, and washed with saturated sodium bicarbonate solution and brine, dried over magnesium sulfate, filtered and concentrated to leave the crude product. Chromatography (elution with ethyl acetate/cyclohexane) provided 119 mg of product.

LC/MS: Retention time, 4.02, 4.21 min; (M+H)=776.

Step 3: (R)-[5-(1H-Benzotriazol-5-yl)-2-fluoro-benzyl]-(4-fluoro-benzyl)-pyrrolidin-2-ylmethyl-amine: A solution of hydrochloric acid in dioxane (4M, 2 mL) was added to a solution of (R)-2-({(4-fluoro-benzyl)-[2-fluoro-5-(1-trityl-1H-benzotriazol-5-yl)-benzyl]-amino}-methyl)-pyrrolidine-1-carboxylic acid tert-butyl ester (119 mg, 0.15 mmol) in 5 mL of methanol and the resulting solution stirred at ambient temperature for 24 h. The volatiles were removed in vacuo and purified by HPLC. The product obtained was treated with hydrochloric acid to give 40 mg of product. LC/MS (long run): Retention time, 6.20 min; (M+H)=433.

¹H NMR (400 MHz, methanol-D₄) δ ppm: 1.68-1.85 (m, 1H) 1.97-2.16 (m, 2H) 2.31-2.45 (m, 1H) 3.38 (t, J=7.47 Hz, 2H) 3.60-3.84 (m, 2H) 4.26 (br s, 1H) 4.75 (d, J=13.18 Hz, 1H) 4.53-4.72 (m, 3H) 7.20 (t, J=8.57 Hz, 2H) 7.38 (t, J=9.23

Hz, 1H) 7.76 (br s, 2H) 7.86-7.96 (m, 2H) 8.00 (d, 1H) 8.10-8.22 (m, 1H) 8.24 (s, 1H).

Examples 81 and 82

Example 80 was substantially repeated in Examples 81 and 82 with the exception of utilizing the respective starting materials and reagents in appropriate quantities in order to prepare the Examples 81 and 82 as tabulated in Table 9. Also summarized in Table 9 are the observed LC/MS data for Examples 81 and 82.

to a mixture of 5-(4-fluoro-3-formylphenyl)-indazole-1-carboxylic acid tert-butyl ester (270 mg, 0.8 mmol) and (2-amino-ethyl)-methyl-carbamic acid tert-butyl ester (210 mg, 1.2 mmol) in 8 mL of dichloroethane. The mixture was stirred at ambient temperature overnight, and then it was diluted with water, the layers were separated and the aqueous phase was extracted with dichloromethane. The combined organic layers were washed with sequentially with water, saturated sodium bicarbonate solution and water, dried over magnesium sulfate, filtered and concentrated to leave the

TABLE 9

| | | LC/MS Data | |
|---|---|---|---|
| Example No. | Chemical Structure and Chemical Name | RT (mins.) | M + H |
| 81 | 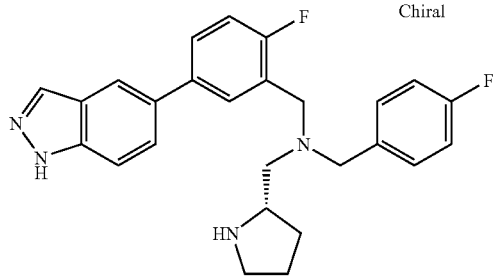<br>(4-Fluoro-benzyl)-[2-fluoro-5-(1H-indazol-5-yl)-benzyl]-pyrrolidin-2S-ylmethyl-amine | 6.51[b] | 433 |
| 82 | 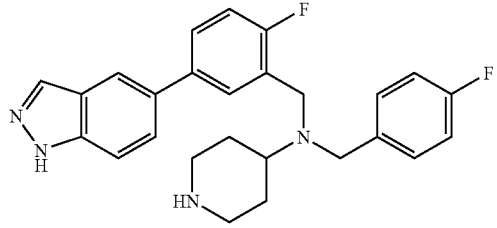<br>(4-Fluoro-benzyl)-[2-fluoro-5-(1H-indazol-5-yl)-benzyl]-piperidin-4-yl-amine | 4.9[b] | 433 |

[b]long LC/MS method

Example 83

N-(4-Fluoro-benzyl)-N-[2-fluoro-5-(1H-indazol-5-yl)-benzyl]-N'-methyl-ethane-1,2-diamine

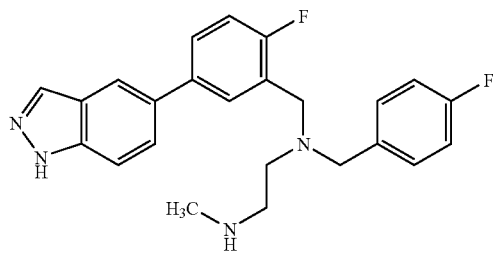

Step 1: 5-(3-{[2-(tert-Butoxycarbonyl-methyl-amino)-ethylamino]-methyl}-4-fluoro-phenyl)-indazole-1-carboxylic acid tert-butyl ester: Sodium triacetoxyborohydride (250 mg, 1.2 mmol) and acetic acid (42 mg, 1.2 mmol) were added crude product. Chromatography (elution with methanol/dichloromethane) provided 400 mg of product. LC/MS: Retention time, 2.66 min; (M+H)=499.

Step 2: 5-(3-{[[2-(tert-Butoxycarbonyl-methyl-amino)-ethyl]-(3-fluoro-benzyl)-amino]-methyl}-4-fluoro-phenyl)-indazole-1-carboxylic acid tert-butyl ester: Sodium triacetoxyborohydride (254 mg, 1.2 mmol) and acetic acid (48 mg, 0.8 mmol) were added to a mixture of 5-(3-{[2-(tert-butoxycarbonyl-methyl-amino)-ethylamino]-methyl}-4-fluoro-phenyl)-indazole-1-carboxylic acid tert-butyl ester (400 mg, 0.8 mmol) and 4-fluorobenzaldehyde (99 mg, 0.8 mmol) in 15 mL of dichloroethane. The mixture was stirred at ambient temperature for 80 h, and then it was diluted with water, the layers were separated and the aqueous phase was extracted with dichloromethane. The combined organic layers were washed with sequentially with water, saturated sodium bicarbonate solution and water, dried over magnesium sulfate, filtered and concentrated to leave the crude product. Chromatography (elution with ethyl acetate/pentane) provided 360 mg of product. LC/MS: Retention time, 4.10 min; (M+H)=607.

Step 3: N-(3-Fluoro-benzyl)-N-[2-fluoro-5-(1H-indazol-5-yl)-benzyl]-N'-methyl-ethane-1,2-diamine: A solution of 2-({(4-fluoro-benzyl)-[2-fluoro-5-(1-trityl-1H-benzotriazol-5-yl)-benzyl]-amino}-methyl)-pyrrolidine-1-carboxylic acid tert-butyl ester (360 mg, 0.59 mmol) in 2 mL of diethyl ether was treated with a solution of hydrochloric acid in dioxane (4M, 12 mL) and the resulting solution stirred at ambient temperature for 4 h. The volatiles were removed in vacuo and the residue was dissolved in water and neutralized with saturated sodium bicarbonate solution. The product was extracted into ethyl acetate and the combined organic layers were washed with sequentially with water, dried over magnesium sulfate, filtered and concentrated to leave the crude product. The residue was dissolved in hot ethyl acetate and the solid obtained upon cooling was collected to give 65 mg of product. LC/MS (long run): Retention time, 6.02 min; (M+H)=407.

$^1$H NMR (400 MHz, chloroform-D) δ ppm: 2.29 (s, 3H) 2.64-2.73 (m, 4H) 3.60 (s, 2H) 3.70 (s, 2H) 6.95 (t, J=8.7 Hz, 2H) 7.08 (t, J=8.7 Hz, 1H) 7.27 (dd, J=8.35, 5.49 Hz, 2H) 7.39-7.46 (m, 1H) 7.48-7.52 (m, 2H) 7.53-7.57 (m, 1H) 7.81 (s, 1H) 8.07 (s, 1H).

Examples 84 to 90

Example 83 was substantially repeated in Examples 84 to 90 with the exception of utilizing the respective starting materials and reagents in appropriate quantities in order to prepare the Examples 84 to 90 as tabulated in Table 10. Also summarized in Table 10 are the observed LC/MS data for Examples 84 to 90.

TABLE 10

| Example No. | Chemical Structure and Chemical Name | LC/MS Data | |
| --- | --- | --- | --- |
| | | RT (mins.) | M + H |
| 84 | 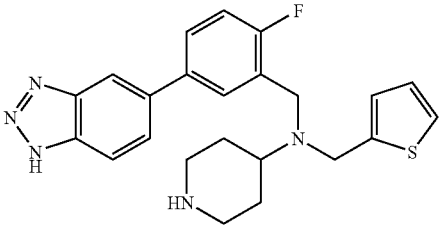 [5-(1H-Benzotriazol-5-yl)-2-fluoro-benzyl]-piperidin-4-yl-thiophen-2-ylmethyl-amine | 4.73$^b$ | 422 |
| 85 | 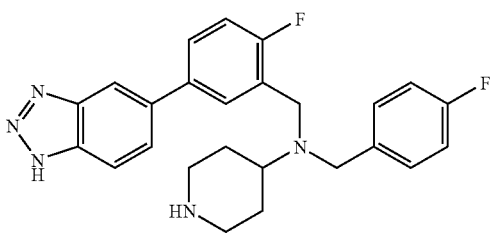 [5-(1H-Benzotriazol-5-yl)-2-fluoro-benzyl]-(4-fluoro-benzyl)-piperidin-4-yl-amine | 4.74$^b$ | 434 |
| 86 | 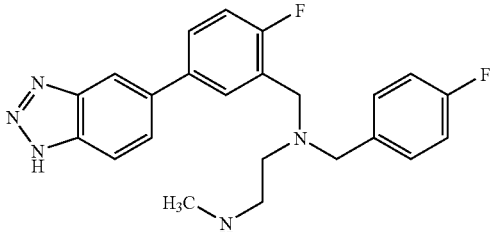 N-[5-(1H-Benzotriazol-5-yl)-2-fluoro-benzyl]-N-(4-fluoro-benzyl)-N'-methyl-ethane-1,2-diamine | 5.71$^b$ | 408 |

TABLE 10-continued

| Example No. | Chemical Structure and Chemical Name | LC/MS Data RT (mins.) | M + H |
|---|---|---|---|
| 87 | 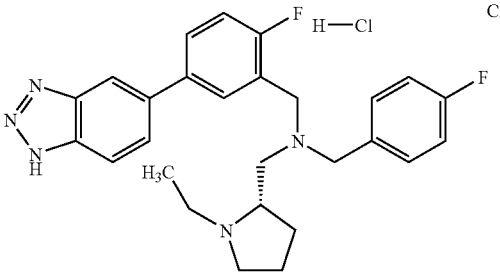<br>[5-(1H-Benzotriazol-5-yl)-2-fluoro-benzyl]-(1-ethyl-pyrrolidin-2S-ylmethyl)-(4-fluoro-benzyl)-amine hydrochloride | Chiral 6.46[b] | 462 |
| 88 | 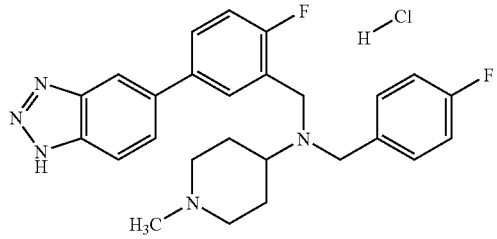<br>[5-(1H-Benzotriazol-5-yl)-2-fluoro-benzyl]-(4-fluoro-benzyl)-(1-methyl-piperidin-4-yl)-amine hydrochloride | 4.95[b] | 448 |
| 89 | 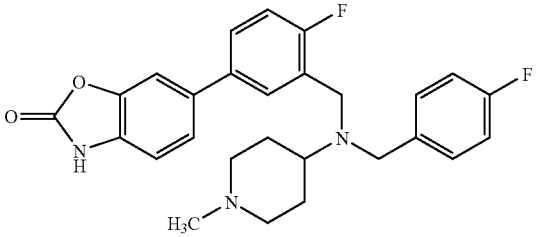<br>6-(4-Fluoro-3-{[(4-fluoro-benzyl)-(1-methyl-piperidin-4-yl)-amino]-methyl}-phenyl)-3H-benzooxazol-2-one | 5.07[b] | 464 |
| 90 | 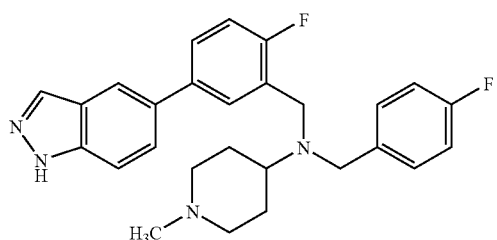<br>(4-Fluoro-benzyl)-[2-fluoro-5-(1H-indazol-5-yl)-benzyl]-(1-methyl-piperidin-4-yl)-amine | 4.71[b] | 447 |

[b] = long LC/MS method

Example 91

5-{5-[2S-(4-Fluoro-phenyl)-4-methyl-piperazin-1-ylmethyl]-pyridin-3-yl}-1H-indole acetate

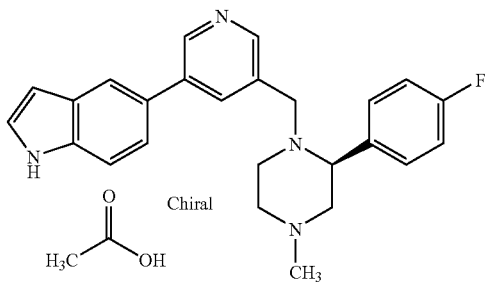

Step 1: (S)-4-(5-Bromo-pyridin-3-ylmethyl)-3-(4-fluorophenyl)-piperazine-1-carboxylic acid tert-butyl ester: Sodium triacetoxyborohydride (1.27 g, 6 mmol) and acetic acid (120 mg, 2 mmol) were added to a mixture of 5-bromo-pyridine-3-carboxaldehyde (372 mg, 2 mmol) and 3S-(4-fluorophenyl)-piperazine-1-carboxylic acid tert-butyl ester (560 mg, 2 mmol) in 10 mL of dichloroethane. The mixture was stirred at ambient temperature overnight, and then it was diluted with dichloromethane and water, the layers were separated and organic layer was washed with brine, dried over sodium sulfate, filtered and concentrated to leave the crude product. Chromatography (elution with ethyl acetate/pentane) provided 625 mg of product. LC/MS: Retention time, 4.2 min; (M+H) 452.

Step 2: (S)-1-(5-Bromo-pyridin-3-ylmethyl)-2-(4-fluorophenyl)-piperazine: A mixture of trifluoroacetic acid and water (TFA:water=19:1, 10 mL) was added to a solution of (S)-4-(5-bromo-pyridin-3-ylmethyl)-3-(4-fluoro-phenyl)-piperazine-1-carboxylic acid tert-butyl ester (300 mg, 0.67 mmol) in 3 mL of dichloromethane and the resulting mixture stirred at ambient temperature for 1.5 h, and then the volatiles were removed in vacuo to leave 470 mg of product. LC/MS: Retention time, 2.13 min; (M+H)=351.

Step 3: (S)-1-(5-Bromo-pyridin-3-ylmethyl)-2-(4-fluorophenyl)-4-methyl-piperazine: Sodium triacetoxyborohydride (1.5 g, 7 mmol) was added to a mixture of (S)-1-(5-bromo-pyridin-3-ylmethyl)-2-(4-fluoro-phenyl)-piperazine (as tris(trifluoroacetate) salt) (820 mg, 1.2 mmol) and formaldehyde (37% aqueous solution, 3 mL, 36.9 mmol) in 20 mL of methanol. The mixture was stirred at ambient temperature overnight, and then the volatiles were removed in vacuo and the residue dissolved in water and the pH was adjusted to 11 by the addition of 10 M sodium hydroxide solution. The product was extracted into dichloromethane and the combined organic layers were washed with brine, dried over sodium sulfate, filtered and concentrated to leave 431 mg of product. LC/MS: Retention time, 2.15 min; (M+H)=366.

Step 4: 5-{5-[2S-(4-Fluoro-phenyl)-4-methyl-piperazin-1-ylmethyl]-pyridin-3-yl}-1H-indole: A mixture of (S)-1-(5-bromo-pyridin-3-ylmethyl)-2-(4-fluoro-phenyl)-4-methyl-piperazine (181 mg, 0.5 mmol), 5-indoleboronic acid (100 mg, 0.62 mmol), cesium carbonate in water (2M, 1 mL, 2 mmol) in 8 mL of dioxane was degassed (evacuate in vacuo and pressurize with nitrogen, three times) $PdCl_2(dppf) \cdot DCM$ (40 mg, 0.05 mmol) was added and the mixture degassed two more times as described above. The resulting mixture was heated at 90° C. for 6 h, then it was allowed to cool to room temperature and the volatiles were removed in vacuo. The residue was triturated with water, the water was decanted and the residue dissolved in methanol. This was filtered and the filtrate evaporated to give crude product. Chromatography on silica gel (elution with $DCE:MeOH:AcOH:H_2O=240:15:3:2$) afforded 110 mg of the product. LC/MS (long run): Retention time, 3.97 min; (M+H)=401.

Examples 92 to 94

Example 91 was substantially repeated in Examples 92 to 94 with the exception of utilizing the respective starting materials and reagents in appropriate quantities in order to prepare the Examples 92 to 94 as tabulated in Table 11. Also summarized in Table 11 are the observed LC/MS data for Examples 92 to 94.

TABLE 11

| Example No. | Chemical Structure and Chemical Name | LC/MS Data RT (mins.) | M + H |
|---|---|---|---|
| 92 | Chiral<br>5-{4-Fluoro-3-[2S-(4-fluoro-phenyl)-4-methyl-piperazin-1-ylmethyl]-phenyl}-1H-indole | 7.02[b] | 418 |

TABLE 11-continued

| Example No. | Chemical Structure and Chemical Name | | LC/MS Data RT (mins.) | M + H |
|---|---|---|---|---|
| 93 | 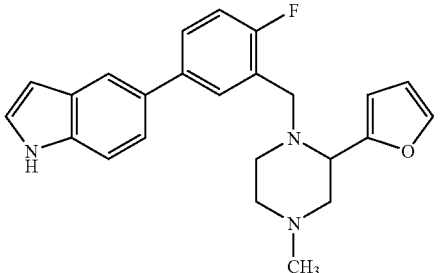<br>5-[4-Fluoro-3-(2-furan-2-yl-4-methyl-piperazin-1-ylmethyl)-phenyl]-1H-indole | | 5.43[b] | 390 |
| 94 | 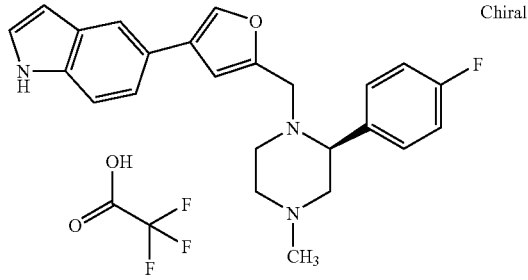<br>5-{5-[2S-(4-Fluoro-phenyl)-4-methyl-piperazin-1-ylmethyl]-furan-3-yl}-1H-indole; compound with trifluoro-acetate | Chiral | 5.6[b] | 390 |

[b] = long LC/MS method

Example 95

6-{5-[2S-(4-Fluorophenyl)-4-methylpiperazine-1-ylmethyl]-furan-3-yl}-3H-benzoxazol-2-one

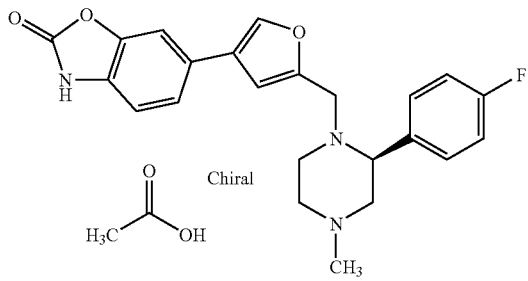

Step 1: 6-Bromo-3H-benzoxazol-2-one: To a mixture of 3H-benzooxazol-2-one (20 g, 0.15 mol) in DCM (500 mL) was added bromine (8.34 mL, 0.16 mol). After stifling at room temperature for 19.5 h, the orange precipitate that had formed was filtered off and washed with DCM until the orange color was washed out. The filtrate was concentrated to approximately 33% of its original volume and filtered and washed as before. The combined solids weighed 28.36 g and contained ca. 8-9% starting material.

Step 2: 6-Bromo-3-trityl-benzoxazol-2-one: To a solution of 6-bromo-3H-benzooxazol-2-one (15 g; ca. 0.07 mol, containing 8-9% 3H-benzooxazol-2-one) and triethylamine (11.1 mL, 0.08 mol) in DCM (250 mL) was added trityl chloride (21.5 g, 0.08 mol). The solution was stirred at room temperature for 18 h and was then washed with distilled water (3×250 mL), brine (250 mL) and dried (MgSO$_4$), filtered and evaporated to give an off-white colored solid. The product was dissolved in refluxing EtOAc then allowed to cool to room temperature with constant stirring for several hours. The solids were collected (21.16 g) and the filtrate was concentrated until precipitation occurred, re-heated (reflux) for several hours and allowed to cool with stirring to encourage a second crystallization (7.88 g).

Step 3: 6-(4,4,5,5-Tetramethyl-[1,3,2]dioxaborolan-2-yl)-3-trityl-3H-benzooxazol-2-one: A mixture of 6-bromo-3-trityl-benzoxazol-2-one (2.5 g, 5.48 mmol), bis(pinacolato)diboron (1.53 g, 6.03 mmol), potassium acetate (2.15 g, 21.91 mmol) and PdCl$_2$(dppf).DCM (447 mg, 0.55 mmol) in degassed, anhydrous DMSO was evacuated and then repressurized with nitrogen. This process was repeated several times to minimize the amount of oxygen in the reaction mixture. The mixture was heated at 85° C. (oil bath temperature) under a nitrogen atmosphere for 2.5 h. The reaction was diluted with DCM (700 mL) and washed twice with distilled water (300 mL each), brine (300 mL), dried (MgSO$_4$), filtered and evaporated to give a dark brown syrup.

The reaction was repeated and the product was combined with that prepared above and chromatographed on a column of silica gel, eluting with 20% Et$_2$O in heptane giving the desired product as a white powder (3.76 g, 68%).

Step 4: 4-(4-Bromofuran-2-ylmethyl)-3S-(4-fluorophenyl)-piperazine-1-carboxylic acid tert-butyl ester: 3S-(4-Fluorophenyl)-piperazine-1-carboxylic acid tert-butyl ester (1.0 g, 3.57 mmol) and 4-bromo-2-furaldehyde (0.63 g, 3.6 mmol) was dissolved in DCE (15 mL) and glacial acetic acid was added (0.23 mL, 3.55 mmol) followed by sodium triacetoxyborohydride (2.30 g, 10.85 mmol). The reaction was stirred overnight at room temperature. DCM (50 mL) was added and the mixture was washed with water (1×50 mL) and brine (1×50 mL) and dried over $Na_2SO_4$. The solvent was removed in vacuo to give an oil, which solidified on standing to provide 1.6 g of product. LC/MS: Retention time, 4.32 min; (M+H)=439.

Step 5: 1-(4-bromofuran-2-ylmethyl)-2S-(4-fluorophenyl)-piperazine-trifluoroacetate: 4-(4-Bromofuran-2-ylmethyl)-3S-(4-fluorophenyl)-piperazine-1-carboxylic acid tert-butyl ester (0.68 g, 1.55 mmol) was taken up in a mixture of 95% TFA aq. and DCM [70:30] and was stirred for 30 mins. The solvent was removed in vacuo to yield a gum (0.90 g, quantitative crude yield). LCMS: Retention time, 2.33 min; (M+H)=339.23.

Step 6: 1-(4-Bromofuran-2-ylmethyl)-2S-(4-fluorophenyl)-4-methylpiperazine: A solution of 1-(4-bromofuran-2-ylmethyl)-2S-(4-fluorophenyl)-piperazine di-trifluoroacetate (0.60 g, 1.06 mmol) in methanol (15 mL) was treated with 37% aqueous formaldehyde (2.5 mL, ~30 mmol) followed by sodium triacetoxyborohydride (1.25 g, 5.5 mmol). The reaction was stirred at room temperature overnight after which the solvent was removed in vacuo to give a gum. Water (20 mL) was added and adjusted to pH 11 with 10M NaOH aq. The mixture was extracted with DCM and the combined DCM layers were washed with brine and dried over $Na_2SO_4$. Solvent removal in vacuo afforded an oil (0.35 g, 94%). This compound was purified via flash silica gel chromatography using DCM:MeOH:AcOH:water (240:15:3:2) as eluent. LC/MS: Retention time, 2.28 min; (M+H)=353.

Step 7: 6-{5-[2S-(4-Fluorophenyl)-4-methylpiperazine-1-ylmethyl]-furan-3-yl}-3-trityl-3H-benzoxazol-2-one: 1-(4-Bromofuran-2-ylmethyl)-2S-(4-fluorophenyl)-4-methylpiperazine (0.164 g, 0.33 mmol) and 6-(4,4,5,5-tetramethyl-[1,3,2]dioxaborolan-2-yl)-3-trityl-3H-benzooxazol-2-one (0.105 g, 0.30 mmol) were dissolved in dioxane (8 mL) and 2M $Cs_2CO_3$ aq. (0.65 mL, 1.3 mmol) was added. The mixture was de-gassed and nitrogen was introduced (three times) when $PdCl_2$(dppf).DCM (0.027 g, 0.03 mmol) was added. After a further de-gassing, the reaction was heated at 100° C. for 4 hours. DCM (20 mL) was added to the mixture and was washed with water and brine. The organic layer was dried over $MgSO_4$ and the solvent removed in vacuo. Chromatography using DCM:MeOH:AcOH:water (240:15:3:2) as eluent gave 0.11 g of the product (68%).

LC/MS: Retention time, 3.13 min; (M+H)=650

Step 8: 6-{5-[2S-(4-Fluorophenyl)-4-methylpiperazine-1-ylmethyl]-furan-3-yl}-3H-benzoxazol-2-one: 6-{5-[2S-(4-Fluorophenyl)-4-methylpiperazine-1-ylmethyl]-furan-3-yl}-3-trityl-3H-benzoxazol-2-one (0.33 g, 0.51 mmol) was taken up in 90% TFA aq. (20 mL) and stirred at room temperature for 2 hours. The solvent was removed in vacuo and co-evaporation of residual TFA was achieved using water (3×~2 mL) to afford a brown solid. Chromatography using DCM:MeOH:AcOH:water (180:20:3:2) as eluent provided 0.15 g of the product (73%). LC/MS (long run): Retention time, 4.39 min; (M+H)=408.

$^1$H NMR (400 MHz, methanol-$D_4$) δ ppm: 2.73 (td, J=12.58, 2.75 Hz, 1H) 2.83 (s, 3H) 3.04 (t, J=11.76 Hz, 1H) 3.16-3.26 (m, 2H) 3.33-3.42 (m, 2H) 3.50 (dd, J=12.09, 1.98 Hz, 1H) 3.65-3.71 (m, 2H) 6.54 (s, 1H) 7.07 (d, J=8.13 Hz, 1H) 7.20 (t, J=8.79 Hz, 2H) 7.33 (dd, J=8.13, 1.54 Hz, 1H) 7.39 (d, J=1.54 Hz, 1H) 7.56 (dd, J=8.46, 5.39 Hz, 2H) 7.83 (d, J=0.88 Hz, 1H).

Examples 96 to 99

Example 95 was substantially repeated in Examples 96 to 99 with the exception of utilizing the respective starting materials and reagents in appropriate quantities in order to prepare the Examples 96 to 99 as tabulated in Table 12. Also summarized in Table 12 are the observed LC/MS data for Examples 96 to 99.

TABLE 12

| Example No. | Chemical Structure and Chemical Name | LC/MS Data | |
|---|---|---|---|
| | | RT (mins.) | M + H |
| 96 | 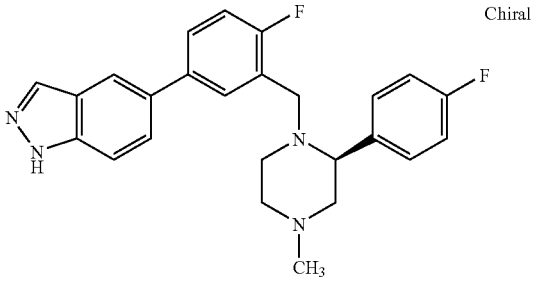<br>5-{4-Fluoro-3-[2S-(4-fluoro-phenyl)-4-methyl-piperazin-1-ylmethyl]-phenyl}-1H-indazole<br>Chiral | 6.22$^b$ | 419 |

TABLE 12-continued

| Example No. | Chemical Structure and Chemical Name | LC/MS Data RT (mins.) | M + H |
|---|---|---|---|
| 97 | 6-{4-Fluoro-3-[2S-(4-fluoro-phenyl)-4-methyl-piperazin-1-ylmethyl]-phenyl}-3H-benzooxazol-2-one | 6.19[b] | 436 |
| 98 | 6-{5-[2S-(4-Fluoro-phenyl)-4-methyl-piperazin-1-ylmethyl]-pyridin-3-yl}-3H-benzooxazol-2-one acetate | 3.85[b] | 419 |
| 99 | 5-{5-[2S-(4-Fluoro-phenyl)-4-methyl-piperazin-1-ylmethyl]-pyridin-3-yl}-1H-indazole | 3.55[b] | 402 |

[b] = long LC/MS method

Example 100

4-Fluoro-N-[2-fluoro-5-(1H-indazol-5-yl)-benzyl]-N-(3-pyrrolidin-1-yl-propyl)-benzamide

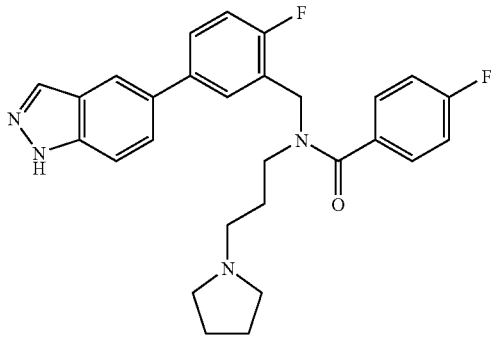

Step 1: 5-{4-Fluoro-3-[(3-pyrrolidin-1-yl-propylamino)-methyl]-phenyl}-indazole-1-carboxylic acid tert-butyl ester: Sodium triacetoxyborohydride (190 mg, 0.88 mmol) was added to a mixture of 5-(4-fluoro-3-formylphenyl)-indazole-1-carboxylic acid tert-butyl ester (100 mg, 0.29 mmol) and N-(3-aminopropyl)pyrrolidine (74 mg, 0.59 mmol) and acetic acid (105 mg, 1.8 mmol) in dichloroethane. The mixture was stirred at ambient temperature overnight, and then it was diluted with dichloromethane and washed with 1 M sodium carbonate solution. The layers were separated and the aqueous phase extracted with dichloromethane. The combined organic layers were dried over magnesium sulfate, filtered and concentrated to leave the crude product. Chromatography (elution with methanol/dichloromethane) provided 130 mg of product. LC/MS: Retention time, 1.98 min; (M+H)=453.

Step 2: 4-Fluoro-N-[2-fluoro-5-(1H-indazol-5-yl)-benzyl]-N-(3-pyrrolidin-1-yl-propyl)-benzamide: HATU (100 mg, 0.28 mmol) was added to a solution of 5-{4-fluoro-3-[(3-pyrrolidin-1-yl-propylamino)-methyl]-phenyl}-indazole-1-carboxylic acid tert-butyl ester (125 mg, 0.28 mmol), 4-fluorobenzoic acid (39 mg, 0.28 mmol) and diisopropylethylamine (89 mg, 0.69 mmol) in 3 mL of dimethylformamide, and the resulting mixture stirred at ambient temperature for 5 h. The mixture was diluted with ethyl acetate washed with 1 M sodium carbonate solution. The layers were separated and the aqueous phase extracted with ethyl acetate. The combined organic phases were washed with brine, dried over magnesium sulfate, filtered and concentrated to leave the crude product. Chromatography (elution with methanol/dichloromethane) provided 100 mg of product. 2 mL of TFA was added to 98 mg of this material in 2 mL of dichloromethane and the mixture stirred at room temperature for 5 h, and the volatiles were removed in vacuo. Chromatography (elution with methanol/dichloromethane) provided 64 mg of product. LC/MS: Retention time, 2.65 min; (M+H)=475.

$^1$H NMR (400 MHz, chloroform-D) δ ppm: 1.98-2.21 (m, 6H) 2.76 (br s, 2H) 3.17 (br s, 2H) 3.59 (br s, 2H) 3.80 (br s, 2H) 4.67 (br s, 2H) 7.07-7.16 (m, 3H) 7.34 (br s, 1H) 7.41-7.72 (m, 5H) 7.84 (br s, 1H) 8.11 (br s, 1H) 12.98 (br s, 1H).

Examples 101 and 102

Example 100 was substantially repeated in Examples 101 and 102 with the exception of utilizing the respective starting materials and reagents in appropriate quantities in order to prepare the Examples 101 and 102 as tabulated in Table 13. Also summarized in Table 13 are the observed LC/MS data for Examples 101 and 102.

TABLE 13

| Example No. | Chemical Structure and Chemical Name | LC/MS Data RT (mins.) | M + H |
|---|---|---|---|
| 101 | N-[5-(1H-Benzotriazol-5-yl)-2-fluoro-benzyl]-4-fluoro-N-(2-pyrrolidin-1-yl-ethyl)-benzamide | 4.87[b] | 462 |
| 102 | 4-Fluoro-N-[2-fluoro-5-(1H-indazol-5-yl)-benzyl]-N-(1-methyl-piperidin-4-yl)-benzamide | 5[b] | 461 |

[b] = long LC/MS method

Example 103

N-(1-Aza-bicyclo[2.2.2]oct-3R-yl)-4-fluoro-N-[2-fluoro-5-(1H-indazol-5-yl)-benzyl]-benzamide

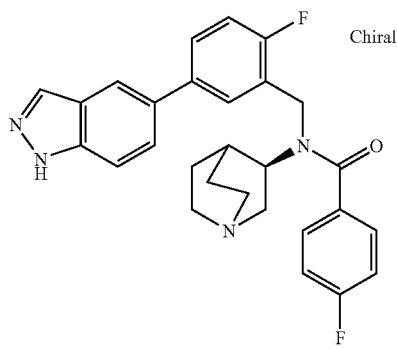

Step 1: 5-(4,4,5,5-Tetramethyl-[1,3,2]dioxaborolan-2-yl)-indazole-1-carboxylic acid tert-butyl ester: A mixture of 5-bromo-indazole-1-carboxylic acid tert-butyl ester (1.8 g, 6.19 mmol), bis(pinacolato)diboron (1.73 g, 6.80 mmol), potassium acetate (2.43 g, 24.7 mmol) and PdCl$_2$(dppf).DCM (505 mg, 0.62 mmol) in degassed, anhydrous DMSO was evacuated and then repressurized with nitrogen. This process was repeated several times to minimize the amount of oxygen in the reaction mixture. The mixture was heated at 85° C. for 4.5 h. The reaction was diluted with DCM and washed with water and brine, dried over MgSO$_4$, filtered and evaporated to give a dark brown syrup. Chromatography on silica gel, eluting with 75% diethyl ether/heptane gave 1.47 g of the product.

Step 2: N-(1-Aza-bicyclo[2.2.2]oct-3R-yl)-4-fluoro-N-[2-fluoro-5-(1H-indazol-5-yl)-benzyl]-benzamide: A mixture of (R)-N-(1-aza-bicyclo[2.2.2]oct-3-yl)-N-(5-bromo-2-fluoro-benzyl)-4-fluoro-benzamide (180 mg, 0.41 mmol), 5-(4,4,5,5-tetramethyl-[1,3,2]dioxaborolan-2-yl)-indazole-1-carboxylic acid tert-butyl ester (170 mg, 0.50 mmol), cesium carbonate in water (2M, 0.82 mL, 1.65 mmol) in 2 mL of dioxane was degassed (evacuate in vacuo and pressurize with nitrogen) PdCl$_2$(dppf).DCM (34 mg, 0.04 mmol) was added and the mixture degassed as above. The resulting mixture was heated at 85° C. for 4 h, then it was allowed to cool to room temperature diluted with chloroform and water. The layers were separated and the organic phase was washed with brine, dried over MgSO$_4$, filtered and evaporated to give crude product. Chromatography on silica gel (elution with methanol/dichloromethane) afforded 100 mg of the product. This material was dissolved in 95% aqueous TFA and stirred at room temperature for 4 h. The volatiles were removed in vacuo to leave the crude product. Chromatography (elution with methanol/dichloromethane) afforded 38 mg of product. LC/MS (long run): Retention time, 5.88 min; (M+H)=473.

$^1$H NMR (400 MHz, methanol-D$_4$) δ ppm: 1.82-1.93 (m, 1H) 1.94-2.06 (m, 2H) 2.30-2.53 (m, 2H) 3.22-3.40 (m, 1H) 3.58-3.68 (m, 1H) 3.72 (ddd, J=13.24, 6.65, 2.09 Hz, 1H) 3.82-3.91 (m, 1H) 4.25-4.33 (m, 1H) 4.80 (d, J=16.93, 1H) 4.91 (d, J=16.93, 1H) 7.14-7.25 (m, 3H) 7.37 (dd, J=7.25, 2.20 Hz, 1H) 7.54-7.67 (m, 5H) 7.93 (s, 1H) 8.11 (s, 1H).

Example 104

N-(2-Dimethylamino-ethyl)-4-fluoro-N-[2-fluoro-5-(2-oxo-2,3-dihydro-benzooxazol-6-yl)-benzyl]-benzamide

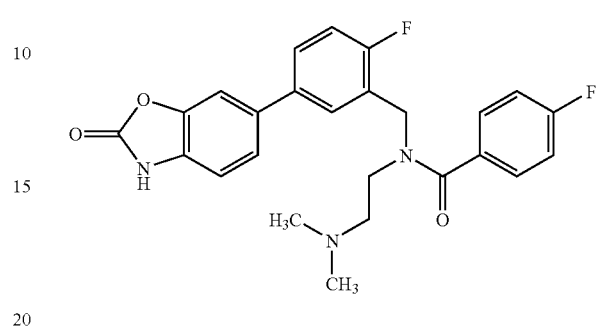

Sodium triacetoxyborohydride (440 mg, 2.1 mmol) was added to a mixture of 2-fluoro-5-(2-oxo-2,3-dihydro-benzooxazol-6-yl)-benzaldehyde (180 mg, 0.7 mmol) and N',N'-dimethylaminoethylenediamine (184 mg, 2.1 mmol) and acetic acid (84 mg, 1.4 mmol) in 5 mL of dichloroethane. The mixture was stirred at ambient temperature overnight, and then it was diluted with dichloromethane and washed with 1 M sodium carbonate solution. The layers were separated and the aqueous phase extracted with dichloromethane. The combined organic layers were washed with brine, dried over magnesium sulfate, filtered and concentrated to leave the crude product. Chromatography (elution with methanol/dichloromethane) provided 130 mg of product. HATU (76 mg, 0.2 mmol) was added to a solution of the above material (65 mg, 0.2 mmol), 4-fluorobenzoic acid (28 mg, 0.2 mmol) and diisopropylethylamine (65 mg, 0.5 mmol) in 3 mL of dimethylformamide, and the resulting mixture stirred at ambient temperature for 4 h. The mixture was diluted with ethyl acetate washed with 1 M sodium carbonate solution. The layers were separated and the aqueous phase extracted with ethyl acetate. The combined organic phases were washed with brine, dried over magnesium sulfate, filtered and concentrated to leave the crude product. Chromatography (two times, elution with methanol/dichloromethane) provided 36 mg of product. The product was dissolved in ethyl acetate and washed with 1 M sodium carbonate solution. The aqueous phase was extracted with ethyl acetate, and the combined organic phases were washed with brine, dried over magnesium sulfate, filtered and concentrated to leave 26 mg of product. LC/MS (long run): Retention time: 5.64 min; (M+H)=452.

$^1$H NMR (400 MHz, methanol-D$_4$) δ ppm: 2.03 (br s, 3H) 2.27 (br s, 3H) 2.38-2.68 (m, 2H) 3.44 (br s, 1H) 3.64 (br s, 1H) 4.70 (br s, 1H) 4.89 (br s, 1H) 7.15 (d, J=8.13 Hz, 2H) 7.17-7.27 (m, 2H) 7.34-7.43 (m, 2H) 7.46 (s, 1H) 7.48-7.54 (m, 2H) 7.54-7.61 (m, 1H).

Examples 105 to 112

Example 104 was substantially repeated in Examples 105 to 112 with the exception of utilizing the respective starting materials and reagents in appropriate quantities in order to prepare the Examples 105 to 112 as tabulated in Table 14. Also summarized in Table 14 are the observed LC/MS data for Examples 105 to 112.

TABLE 14

| Example No. | Chemical Structure and Chemical Name | LC/MS Data RT (mins.) | M + H |
|---|---|---|---|
| 105 | 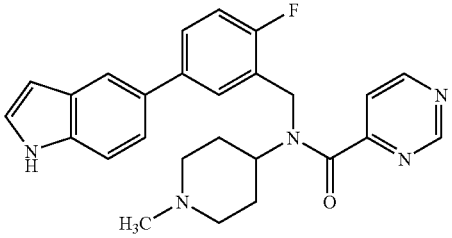<br>Pyrimidine-4-carboxylic acid [2-fluoro-5-(1H-indol-5-yl)-benzyl]-(1-methyl-piperidin-4-yl)-amide | 5.24[b] | 444 |
| 106 | 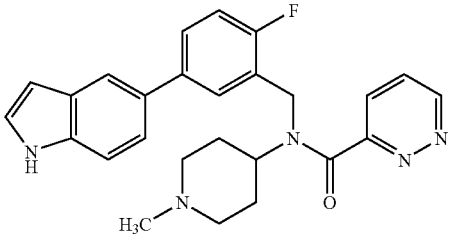<br>Pyridazine-3-carboxylic acid [2-fluoro-5-(1H-indol-5-yl)-benzyl]-(1-methyl-piperidin-4-yl)-amide | 5.18[b] | 444 |
| 107 | 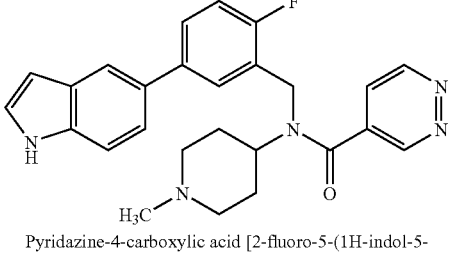<br>Pyridazine-4-carboxylic acid [2-fluoro-5-(1H-indol-5-yl)-benzyl]-(1-methyl-piperidin-4-yl)-amide | 5.05[b] | 444 |
| 108 | 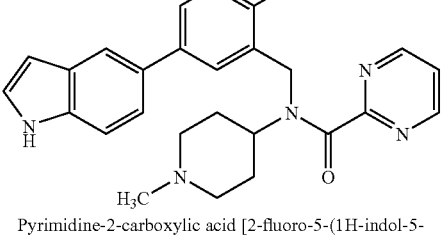<br>Pyrimidine-2-carboxylic acid [2-fluoro-5-(1H-indol-5-yl)-benzyl]-(1-methyl-piperidin-4-yl)-amide | 5[b] | 444 |
| 109 | 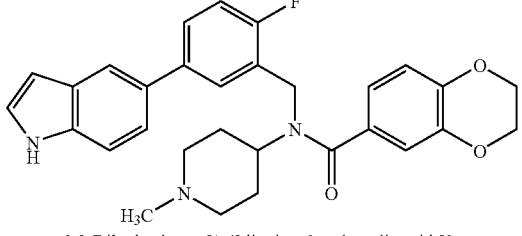<br>2,3-Dihydro-benzo[1,4]dioxine-6-carboxylic acid [2-fluoro-5-(1H-indol-5-yl)-benzyl]-(1-methyl-piperidin-4-yl)-amide | 6.38[b] | 500 |

TABLE 14-continued

| Example No. | Chemical Structure and Chemical Name | LC/MS Data RT (mins.) | M + H |
|---|---|---|---|
| 110 | N-[2-Fluoro-5-(1H-indol-5-yl)-benzyl]-4-isopropoxy-N-(1-methyl-piperidin-4-yl)-benzamide | 7.14[b] | 500 |
| 111 | N-[2-Fluoro-5-(1H-indol-5-yl)-benzyl]-3-isopropoxy-N-(1-methyl-piperidin-4-yl)-benzamide | 7.1[b] | 500 |
| 112 | N-[2-Fluoro-5-(1H-indol-5-yl)-benzyl]-N-(1-methyl-piperidin-4-yl)-4-trifluoromethoxy-benzamide | 7.37[b] | 526 |

[b] = long LC/MS method

Example 113

5-{5-[2S-(4-Fluoro-phenyl)-piperazin-1-ylmethyl]-pyridin-3-yl}-1H-indazole

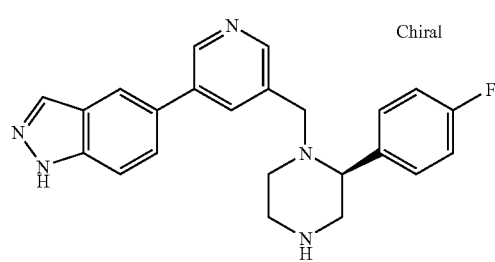

Step 1: 5-{5-[4-tert-Butoxycarbonyl-2S-(4-fluoro-phenyl)-piperazin-1-ylmethyl]-pyridin-3-yl}-indazole-1-carboxylic acid tert-butyl ester: 4-(5-Bromo-pyridin-3-ylmethyl)-3-(4-fluoro-phenyl)-piperazine-1-carboxylic acid tert-butyl ester (225 mg, 0.5 mmol) and 5-(4,4,5,5-tetramethyl-[1,3,2]dioxaborolan-2-yl)-indazole-1-carboxylic acid tert-butyl ester (172 mg, 0.5 mmol) were dissolved in dioxane (8 mL) and 2M $Cs_2CO_3$ aq. (1 mL, 2 mmol) was added. The mixture was de-gassed and nitrogen was introduced (three times) when $PdCl_2$(dppf).DCM (30 mg, 0.036 mmol) was added. The reaction was heated at 90° C. for 4 hours. The volatiles were removed in vacuo and the residue was dissolved in dichloromethane. The organic phase was washed with water and brine. The organic layer was dried over $Na_2SO_4$ and the solvent removed in vacuo. Purification was achieved via flash silica gel chromatography (elution with ethyl acetate/pentane) to give 175 mg of product. LC/MS: Retention time, 4.05 min; (M+H)=587.

Step 2: 5-{5-[2S-(4-Fluoro-phenyl)-piperazin-1-ylmethyl]-pyridin-3-yl}-1H-indazole: 7 mL of 95% aqueous TFA was added to a solution of 5-{5-[4-tert-butoxycarbonyl-2S-(4-fluoro-phenyl)-piperazin-1-ylmethyl]-pyridin-3-yl}-indazole-1-carboxylic acid tert-butyl ester (170 mg, 0.29 mmol) in 3 mL of dichloromethane, and the resulting mixture was stirred at room temperature for 1 h. The solvent was removed to afford the crude product. Purification was achieved via flash silica gel chromatography using DCM:MeOH:AcOH:water as eluent. The pooled fractions were combined and the solvent was removed in vacuo with co-evaporation of residual AcOH using water (3×~2 mL) and MeOH:DCM (1:1, 10 mL) to give 125 mg of product. LCMS (long run): Retention time, 3.6 min; (M+H)=388.

Examples 114 to 117

Example 113 was substantially repeated in Examples 114 to 117 with the exception of utilizing the respective starting materials and reagents in appropriate quantities in order to prepare the Examples 114 to 117 as tabulated in Table 15. Also summarized in Table 15 are the observed LC/MS data for Examples 114 to 117.

TABLE 15

| Example No. | Chemical Structure and Chemical Name | | RT (mins.) | M + H |
|---|---|---|---|---|
| 114 | 5-{5-[2S-(4-Fluoro-phenyl)-piperazin-1-ylmethyl]-pyridin-3-yl}-1H-indole acetate | Chiral | 3.72[b] | 387 |
| 115 | 5-{5-[2S-(4-Fluoro-phenyl)-piperazin-1-ylmethyl]-furan-3-yl}-1H-indole | Chiral | 5.52[b] | 376 |
| 116 | 5-{5-[2S-(4-Fluoro-phenyl)-piperazin-1-ylmethyl]-furan-3-yl}-1H-indazole | Chiral | 4.86[b] | 377 |
| 117 | 6-{5-[2S-(4-Fluoro-phenyl)-piperazin-1-ylmethyl]-furan-3-yl}-3H-benzooxazol-2-one acetate | Chiral | 4.27[b] | 394 |

[b] = long LC/MS method

Example 118

6-(5-{[(4-Fluoro-benzyl)-(1-methyl-piperidin-4-yl)-amino]-methyl}-furan-3-yl)-3H-benzooxazol-2-one

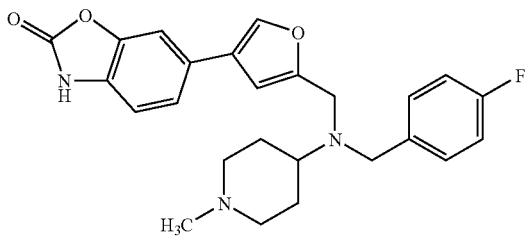

Step 1: 6-{5-[(1-Methyl-piperidin-4-ylamino)-methyl]-furan-3-yl}-3-trityl-3H-benzooxazol-2-one: Sodium triacetoxyborohydride (339 mg, 1.6 mmol) was added to a solution of 4-(2-oxo-3-trityl-2,3-dihydro-benzooxazol-6-yl)-furan-2-carbaldehyde (377 mg, 0.8 mmol) and 1-methyl-piperidin-4-ylamine (219 mg, 1.92 mmol) and acetic acid (192 mg, 3.2 mmol) in 10 mL of 1,2-dichloroethane. The mixture was stirred at ambient temperature for 21 h, and then it was diluted with dichloromethane and washed with saturated sodium carbonate solution. The aqueous phase was extracted with dichloromethane, and the combined organic phases were washed with water and brine, dried over magnesium sulfate, filtered and concentrated to leave the crude product. Chromatography (elution with dichloromethane/methanol/acetic acid/water) gave 189 mg of product. LC/MS: Retention time, 2.38 min; (M+H)=570.

Step 2: 6-(5-{[(4-Fluoro-benzyl)-(1-methyl-piperidin-4-yl)-amino]-methyl}-furan-3-yl)-3-trityl-3H-benzooxazol-2-one: Sodium triacetoxyborohydride (71 mg, 0.33 mmol) was added to a solution of 6-{5-[(1-methyl-piperidin-4-ylamino)-methyl]-furan-3-yl}-3-trityl-3H-benzooxazol-2-one (95 mg, 0.17 mmol) and 4-fluorobenzaldehyde (21 mg, 0.2 mmol) and acetic acid (20 mg, 0.33 mmol) in 1.5 mL of 1,2-dichloroethane. The mixture was stirred at ambient temperature for 20 h, and then it was diluted with chloroform and washed with saturated sodium carbonate solution. The aqueous phase was extracted with chloroform, and the combined organic phases were washed with water and brine, dried over magnesium sulfate, filtered and concentrated to leave the crude product. Chromatography (elution with dichloromethane/methanol) gave 64 mg of product.
LC/MS: Retention time, 2.99 min; (M+H)=678.

Step 3: 6-(5-{[(4-Fluoro-benzyl)-(1-methyl-piperidin-4-yl)-amino]-methyl}-furan-3-yl)-3H-benzooxazol-2-one: 1 mL of 95% aqueous TFA was added to a solution of 6-(5-{[(4-fluoro-benzyl)-(1-methyl-piperidin-4-yl)-amino]-methyl}-furan-3-yl)-3-trityl-3H-benzooxazol-2-one (64 mg, 0.09 mmol) in 2 mL of dichloromethane, and the resulting mixture was stirred at room temperature for 1 h. The solvent was removed to afford the crude product. Purification was achieved via flash silica gel chromatography (elution with DCM:MeOH:AcOH:water). The pooled fractions were combined and the solvent was removed in vacuo with co-evaporation of residual AcOH using toluene to give 16 mg of product. LC/MS (long run): Retention time, 3.83 min; (M+H)=436.

$^1$H NMR (400 MHz, methanol-D$_4$) δ ppm: 1.86 (q, J=13.14 Hz, 2H) 2.14 (d, J=13.8 Hz, 2H) 2.84 (s, 3H) 2.92-3.08 (m, 3H) 3.55 (d, J=13.14 Hz, 2H) 3.75 (s, 2H) 3.79 (s, 2H) 6.62 (s, 1H) 6.68-7.11 (m, 3H), 7.34 (d, J=8.06 Hz, 1H) 7.38-7.44 (m, 3H) 7.82 (s, 1H).

Example 119

(4-Fluoro-benzyl)-[4-(1H-indazol-5-yl)-furan-2-ylmethyl]-(1-methyl-piperidin-4-yl)-amine

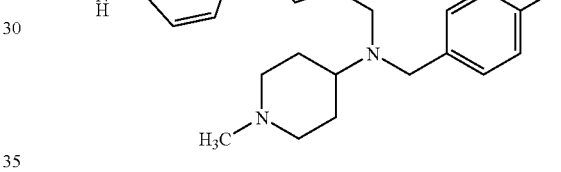

Example 118 was substantially repeated in Example 119 with the exception of utilizing the respective starting materials and reagents in appropriate quantities in order to prepare the Example 119. LC/MS (long run): Retention time, 4.07 min; (M+H)=419.

Examples 120 to 169

The following Examples 120 to 169 were prepared following various procedures as described herein with the exception of utilizing the respective starting materials and reagents in appropriate quantities in order to prepare the Examples 120 to 169 as tabulated in Table 16. Also summarized in Table 16 are the synthetic method used for the preparation of respective Example and the observed LC/MS data.

TABLE 16

| Example No. | Synthetic Method Used | Chemical Structure and Chemical Name | LC/MS Data RT (mins.) | M + H |
|---|---|---|---|---|
| 120 | Example 1 | 5-[3-(4-Methyl-piperazin-1-ylmethyl)-phenyl]-1H-indole | n.a. | n.a. |

TABLE 16-continued

| Example No. | Synthetic Method Used | Chemical Structure and Chemical Name | LC/MS Data RT (mins.) | M + H |
|---|---|---|---|---|
| 121 | Example 1 | 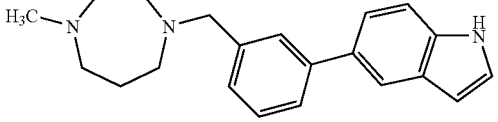<br>5-[3-(4-Methyl-[1,4]diazepan-1-ylmethyl)-phenyl]-1H-indole | n.a. | n.a. |
| 122 | Example 1 | 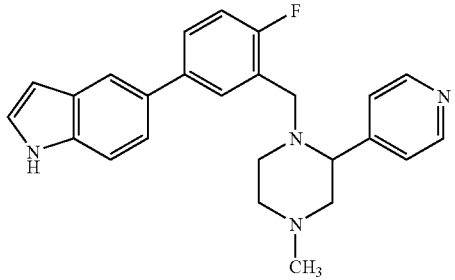<br>5-[4-Fluoro-3-(4-methyl-2-pyridin-4-yl-piperazin-1-ylmethyl)-phenyl]-1H-indole | 4.91[b] | 401 |
| 123 | Example 1 | Chiral<br>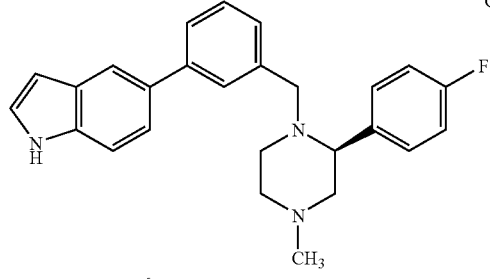<br>5-{3-[2S-(4-Fluoro-phenyl)-4-methyl-piperazin-1-ylmethyl]-phenyl}-1H-indole | 7.02[b] | 400 |
| 124 | Example 17 | 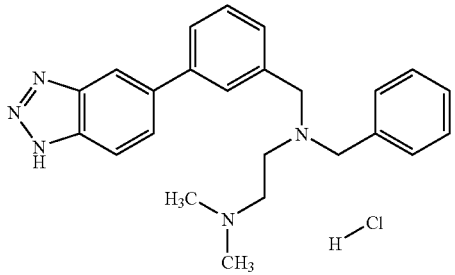<br>N-[3-(1H-Benzotriazol-5-yl)-benzyl]-N-benzyl-N',N'-dimethyl-ethane-1,2-diamine hydrochloride | n.a. | n.a. |
| 125 | Example 20 | 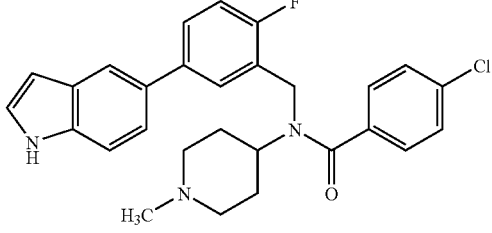<br>4-Chloro-N-[2-fluoro-5-(1H-indol-5-yl)-benzyl]-N-(1-methyl-piperidin-4-yl)-benzamide | 6.72[b] | 476 |

TABLE 16-continued

| Example No. | Synthetic Method Used | Chemical Structure and Chemical Name | RT (mins.) | M + H |
|---|---|---|---|---|
| 126 | Example 20 | 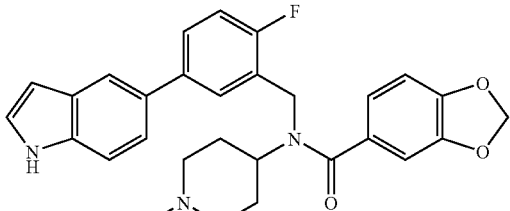 Benzo[1,3]dioxole-5-carboxylic acid [2-fluoro-5-(1H-indol-5-yl)-benzyl]-(1-methyl-piperidin-4-yl)-amide | 6.15[b] | 486 |
| 127 | Example 20 | 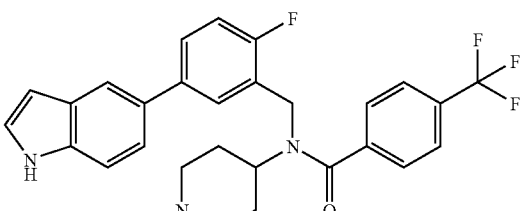 N-[2-Fluoro-5-(1H-indol-5-yl)-benzyl]-N-(1-methyl-piperidin-4-yl)-4-trifluoromethyl-benzamide | 7.06[b] | 510 |
| 128 | Example 20 | 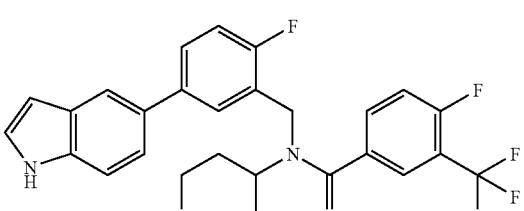 4-Fluoro-N-[2-fluoro-5-(1H-indol-5-yl)-benzyl]-N-(1-methyl-piperidin-4-yl)-3-trifluoromethyl-benzamide | 7.11[b] | 528 |
| 129 | Example 20 | 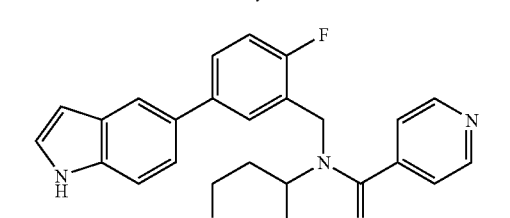 N-[2-Fluoro-5-(1H-indol-5-yl)-benzyl]-N-(1-methyl-piperidin-4-yl)-isonicotinamide | 4.99[b] | 443 |
| 130 | Example 20 | 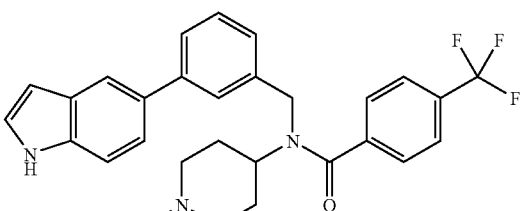 N-[3-(1H-Indol-5-yl)-benzyl]-N-(1-methyl-piperidin-4-yl)-4-trifluoromethyl-benzamide | 6.92[b] | 492 |

TABLE 16-continued

| Example No. | Synthetic Method Used | Chemical Structure and Chemical Name | LC/MS Data RT (mins.) | M + H |
|---|---|---|---|---|
| 131 | Example 20 | 4-Fluoro-N-[4-fluoro-3-(1H-indol-5-yl)-benzyl]-N-(2-pyrrolidin-1-yl-ethyl)-benzamide | 6.73[b] | 460 |
| 132 | Example 20 | N-[2-Fluoro-5-(1H-indol-5-yl)-benzyl]-N-(2-pyrrolidin-1-yl-ethyl)-4-trifluoromethyl-benzamide | 6.85[b] | 510 |
| 133 | Example 20 | 4-Fluoro-N-[3-fluoro-5-(1H-indol-5-yl)-benzyl]-N-(2-pyrrolidin-1-yl-ethyl)-benzamide | 6.75[b] | 460 |
| 134 | Example 20 | N-[3-(1H-Indol-5-yl)-benzyl]-N-(2-pyrrolidin-1-yl-ethyl)-4-trifluoromethyl-benzamide | 7.07[b] | 492 |

TABLE 16-continued

| Example No. | Synthetic Method Used | Chemical Structure and Chemical Name | LC/MS Data RT (mins.) | M + H |
|---|---|---|---|---|
| 135 | Example 20 | N-[3-(1H-Indol-5-yl)-benzyl]-N-(2-pyrrolidin-1-yl-ethyl)-isonicotinamide | 5.05[b] | 425 |
| 136 | Example 20 | N-[4-Fluoro-3-(1H-indol-5-yl)-benzyl]-N-(2-pyrrolidin-1-yl-ethyl)-4-trifluoromethyl-benzamide | 7.16[b] | 510 |
| 137 | Example 42 | 5-[4-Fluoro-3-(2R-thiophen-2-yl-piperazin-1-ylmethyl)-phenyl]-1H-indazole acetate | 5.16[b] | 393 |
| 138 | Example 53 | 4-Fluoro-N-[4-(1H-indazol-5-yl)-furan-2-ylmethyl]-N-(1-methyl-piperidin-4-yl)-benzamide | 4.61[b] | 433 |

TABLE 16-continued

| Example No. | Synthetic Method Used | Chemical Structure and Chemical Name | LC/MS Data RT (mins.) | M + H |
|---|---|---|---|---|
| 139 | Example 53 | 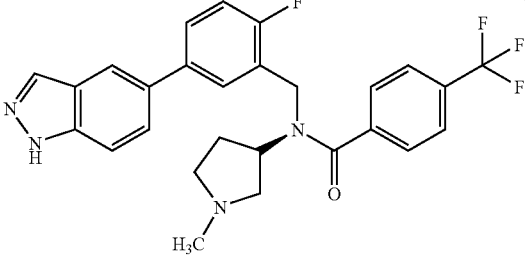 N-[2-Fluoro-5-(1H-indazol-5-yl)-benzyl]-N-(1-methyl-pyrrolidin-3R-yl)-4-trifluoromethyl-benzamide | Chiral 6.64[b] | 497 |
| 140 | Example 70 | 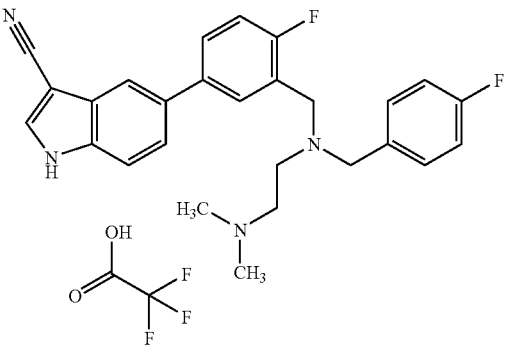 5-(3-{[(2-Dimethylamino-ethyl)-(4-fluoro-benzyl)-amino]-methyl}-4-fluoro-phenyl)-1H-indole-3-carbonitrile trifluoro-acetate | 5.78[b] | 445 |
| 141 | Example 77 | 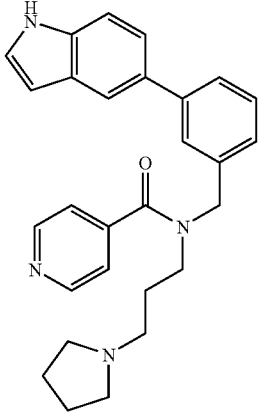 N-[3-(1H-Indol-5-yl)-benzyl]-N-(3-pyrrolidin-1-yl-propyl)-isonicotinamide | 2.12[c] | 439 |

TABLE 16-continued

| | Synthetic | | LC/MS Data | |
|---|---|---|---|---|
| Example No. | Method Used | Chemical Structure and Chemical Name | RT (mins.) | M + H |
| 142 | Example 77 | N-[4-Fluoro-3-(1H-indol-5-yl)-benzyl]-N-(3-pyrrolidin-1-yl-propyl)-isonicotinamide | 2.15[c] | 457 |
| 143 | Example 77 | Pyridine-2-carboxylic acid [3-(1H-indol-5-yl)-benzyl]-(3-pyrrolidin-1-yl-propyl)-amide | 2.3[c] | 439 |
| 144 | Example 77 | N-[3-(1H-Indol-5-yl)-benzyl]-N-(3-pyrrolidin-1-yl-propyl)-4-trifluoromethyl-benzamide | 2.73[c] | 506 |

TABLE 16-continued

| Example No. | Synthetic Method Used | Chemical Structure and Chemical Name | RT (mins.) | M + H |
|---|---|---|---|---|
| 145 | Example 77 | 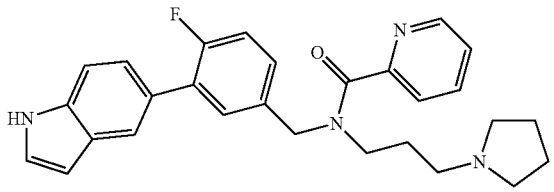<br>Pyridine-2-carboxylic acid [4-fluoro-3-(1H-indol-5-yl)-benzyl]-(3-pyrrolidin-1-yl-propyl)-amide | 2.35$^c$ | 457 |
| 146 | Example 77 | 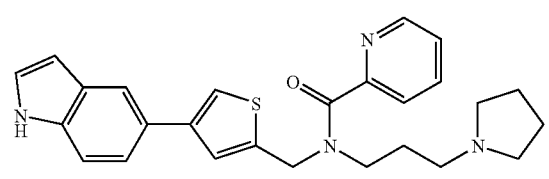<br>Pyridine-2-carboxylic acid [4-(1H-indol-5-yl)-thiophen-2-ylmethyl]-(3-pyrrolidin-1-yl-propyl)-amide | 2.64$^c$ | 445 |
| 147 | Example 77 | 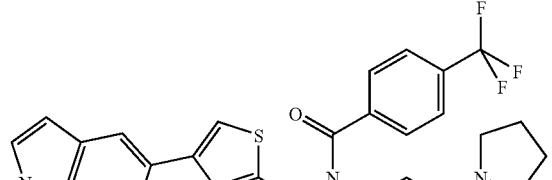<br>N-[4-(1H-Indol-5-yl)-thiophen-2-ylmethyl]-N-(3-pyrrolidin-1-yl-propyl)-4-trifluoromethyl-benzamide | 3.0$^c$ | 512 |
| 148 | Example 77 | 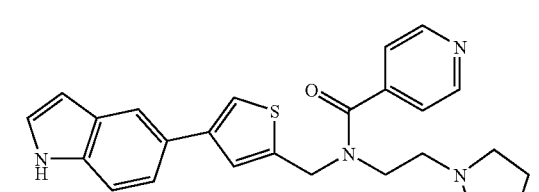<br>N-[4-(1H-Indol-5-yl)-thiophen-2-ylmethyl]-N-(2-pyrrolidin-1-yl-ethyl)-isonicotinamide | 2.47$^c$ | 431 |
| 149 | Example 77 | 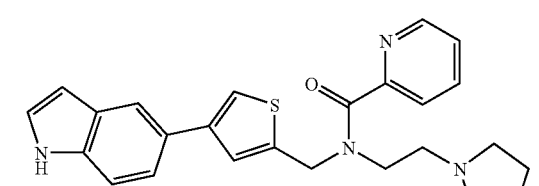<br>Pyridine-2-carboxylic acid [4-(1H-indol-5-yl)-thiophen-2-ylmethyl]-(2-pyrrolidin-1-yl-ethyl)-amide | 2.67$^c$ | 431 |

TABLE 16-continued

| Example No. | Synthetic Method Used | Chemical Structure and Chemical Name | LC/MS Data RT (mins.) | M + H |
|---|---|---|---|---|
| 150 | Example 77 | 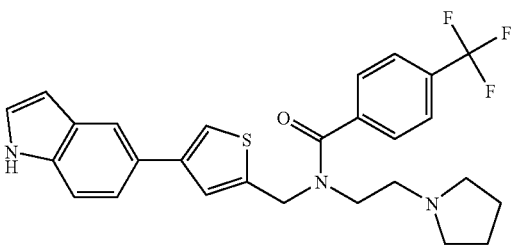<br>N-[4-(1H-Indol-5-yl)-thiophen-2-ylmethyl]-N-(2-pyrrolidin-1-yl-ethyl)-4-trifluoromethyl-benzamide | 3.01$^c$ | 498 |
| 151 | Example 77 | 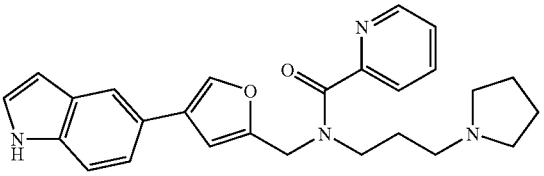<br>Pyridine-2-carboxylic acid [4-(1H-indol-5-yl)-furan-2-ylmethyl]-(3-pyrrolidin-1-yl-propyl)-amide | 2.55$^c$ | 429 |
| 152 | Example 77 | 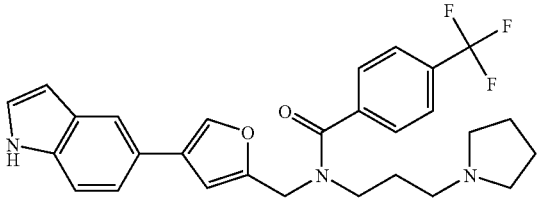<br>N-[4-(1H-Indol-5-yl)-furan-2-ylmethyl]-N-(3-pyrrolidin-1-yl-propyl)-4-trifluoromethyl-benzamide | 2.95$^c$ | 496 |
| 153 | Example 77 | 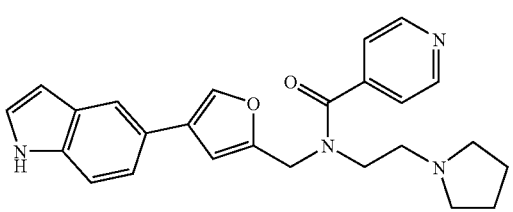<br>N-[4-(1H-Indol-5-yl)-furan-2-ylmethyl]-N-(2-pyrrolidin-1-yl-ethyl)-isonicotinamide | 2.37$^c$ | 415 |
| 154 | Example 77 | 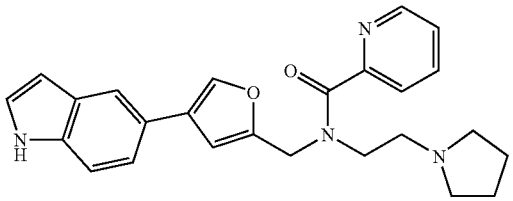<br>Pyridine-2-carboxylic acid [4-(1H-indol-5-yl-furan-2-ylmethyl]-(2-pyrrolidin-1-yl-ethyl)-amide | 2.55$^c$ | 415 |

TABLE 16-continued

| Example No. | Synthetic Method Used | Chemical Structure and Chemical Name | LC/MS Data RT (mins.) | M + H |
|---|---|---|---|---|
| 155 | Example 77 | 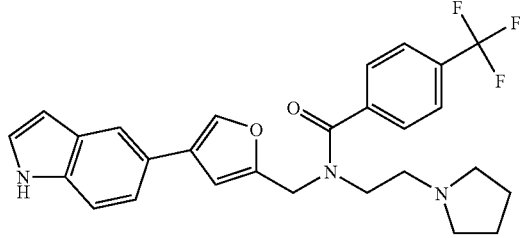 N-[4-(1H-Indol-5-yl)-furan-2-ylmethyl]-N-(2-pyrrolidin-1-yl-ethyl)-4-trifluoromethyl-benzamide | 2.94$^e$ | 482 |
| 156 | Example 77 | 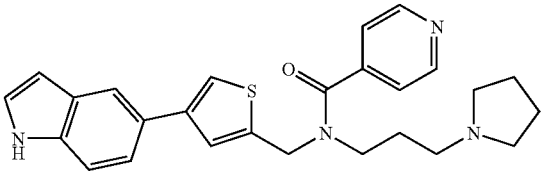 N-[4-(1H-Indol-5-yl)-thiophen-2-ylmethyl]-N-(3-pyrrolidin-1-yl-propyl)-isonicotinamide | 2.44$^e$ | 445 |
| 157 | Example 77 | 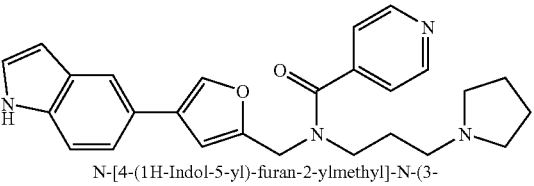 N-[4-(1H-Indol-5-yl)-furan-2-ylmethyl]-N-(3-pyrrolidin-1-yl-propyl)-isonicotinamide | 2.39$^e$ | 429 |
| 158 | Example 77 | 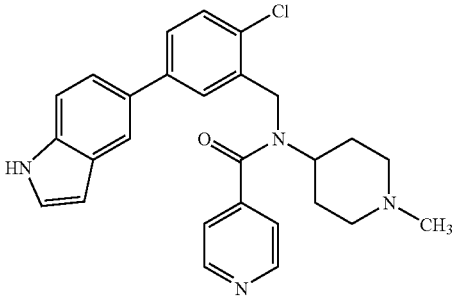 N-[2-Chloro-5-(1H-indol-5-yl)-benzyl]-N-(1-methyl-piperidin-4-yl)-isonicotinamide | 2.54$^e$ | 459 |
| 159 | Example 95 | Chiral 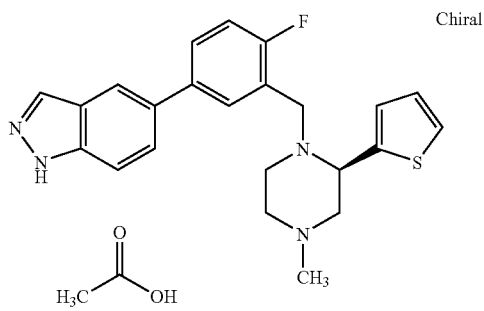 5-[4-Fluoro-3-(4-methyl-2R-thiophen-2-yl-piperazin-1-ylmethyl)-phenyl]-1H-indazole acetate | 6.11$^b$ | 407 |

TABLE 16-continued

| Example No. | Synthetic Method Used | Chemical Structure and Chemical Name | | LC/MS Data RT (mins.) | M + H |
|---|---|---|---|---|---|
| 160 | Example 95 | 5-[4-Fluoro-3-(4-methyl-2R-thiophen-2-yl-piperazin-1-ylmethyl)-phenyl]-1H-indazole acetate | Chiral | 6.04[b] | 407 |
| 161 | Example 103 | 5-{5-[2S-(4-Fluoro-phenyl)-4-methyl-piperazin-1-ylmethyl]-furan-3-yl}-1H-indazole | Chiral | 4.91[b] | 391 |
| 162 | Example 104 | Pyrazine-2-carboxylic acid [2-fluoro-5-(1H-indol-5-yl)-benzyl]-(1-methyl-piperidin-4-yl)-amide | | 5.63[b] | 444 |
| 163 | Example 104 | Pyridine-2-carboxylic acid [2-fluoro-5-(1H-indol-5-yl)-benzyl]-(1-methyl-piperidin-4-yl)-amide | | 5.55[b] | 443 |

TABLE 16-continued

| Example No. | Synthetic Method Used | Chemical Structure and Chemical Name | LC/MS Data RT (mins.) | M + H |
|---|---|---|---|---|
| 164 | Example 104 | 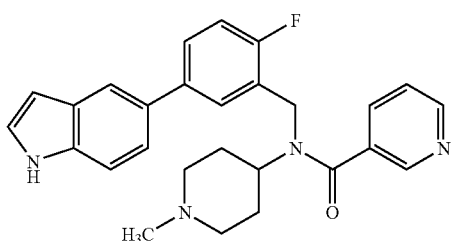<br>N-[2-Fluoro-5-(1H-indol-5-yl)-benzyl]-N-(1-methyl-piperidin-4-yl)-nicotinamide | 5.15[b] | 443 |
| 165 | Example 104 | 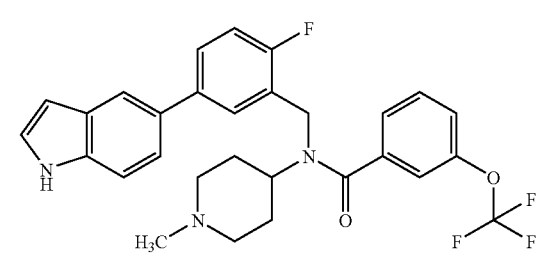<br>N-[2-Fluoro-5-(1H-indol-5-yl)-benzyl]-N-(1-methyl-piperidin-4-yl)-3-trifluoromethoxy-benzamide | 7.06[b] | 526 |
| 166 | Example 104 | 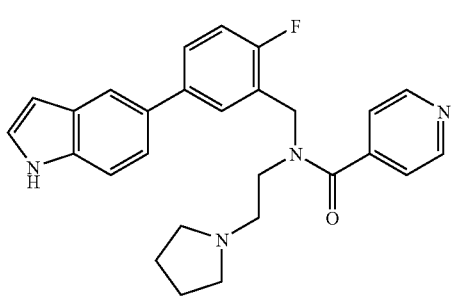<br>N-[2-Fluoro-5-(1H-indol-5-yl)-benzyl]-N-(2-pyrrolidin-1-yl-ethyl)-isonicotinamide | 5.19[b] | 443 |
| 167 | Example 104 | 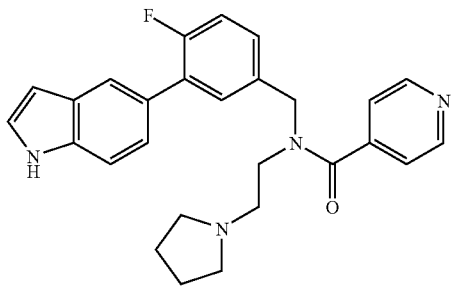<br>N-[4-Fluoro-3-(1H-indol-5-yl)-benzyl]-N-(2-pyrrolidin-1-yl-ethyl)-isonicotinamide | 5.22[b] | 443 |

TABLE 16-continued

| Example No. | Synthetic Method Used | Chemical Structure and Chemical Name | LC/MS Data RT (mins.) | M + H |
|---|---|---|---|---|
| 168 | Example 104 | 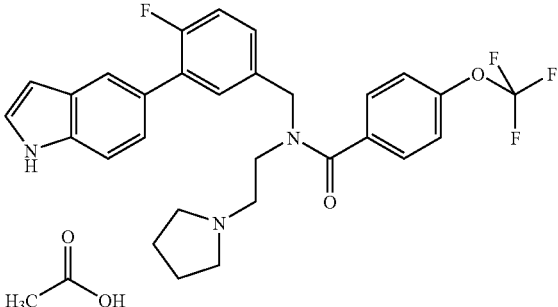<br>N-[4-Fluoro-3-(1H-indol-5-yl)-benzyl]-N-(2-pyrrolidin-1-yl-ethyl)-4-trifluoromethoxy-benzamide acetate | 7.34[b] | 460 |
| 169 | Example 104 | 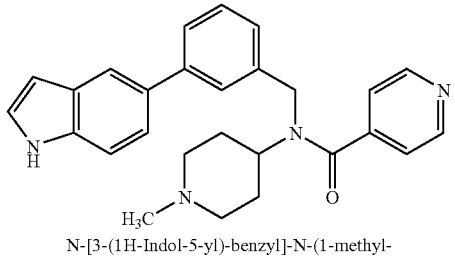<br>N-[3-(1H-Indol-5-yl)-benzyl]-N-(1-methyl-piperidin-4-yl)-isonicotinamide | 4.69[b] | 425 |

[a] = short LC/MS method;
[b] = long LC/MS method;
[c] = method 3;
n.a. = not available.

Example 170

5-{4-Fluoro-3-[2S-(4-fluoro-phenyl)-4-methyl-piperazin-1-ylmethyl]-phenyl}-3-methyl-1H-indole

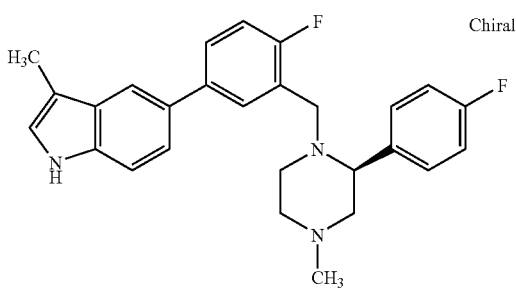

Step 1: (S)-2-(4-Fluoro-phenyl)-1-[2-fluoro-5-(4,4,5,5-tetramethyl-[1,3,2]dioxaborolan-2-yl)-benzyl]-4-methyl-piperazine: A mixture of (S)-1-(5-bromo-2-fluoro-benzyl)-2-(4-fluoro-phenyl)-4-methyl-piperazine (0.87 g, 2.28 mmol), bis(pinacolato)diboron (0.61 g, 2.39 mmol), potassium acetate (0.89 g, 9.11 mmol) and PdCl₂(dppf).DCM (186 mg, 0.23 mmol) in degassed, anhydrous DMSO was evacuated and then repressurized with nitrogen. This process was repeated several times to minimize the amount of oxygen in the reaction mixture. The mixture was heated at 85° C. for 4 h. The reaction was diluted with DCM and washed with water and brine, dried over MgSO₄, filtered and evaporated to give a dark brown syrup. Chromatography on silica gel, eluting with 2% isopropanol/DCM gave 709 mg of the product.

Step 2: 5-{4-Fluoro-3-[2S-(4-fluoro-phenyl)-4-methyl-piperazin-1-ylmethyl]-phenyl}-3-methyl-1H-indole. Fibre-Cat 1001 (4 mg, 0.0006 mmol) was added to a mixture of 5-bromo-3-methylindole (30 mg, 0.14 mmol), (S)-2-(4-fluoro-phenyl)-1-[2-fluoro-5-(4,4,5,5-tetramethyl-[1,3,2]dioxaborolan-2-yl)-benzyl]-4-methyl-piperazine (60 mg, 0.14 mmol), tetrabutylammonium bromide (45 mg, 0.14 mmol), and cesium carbonate (2M, 280 μL, 0.56 mmol) in 4 mL of 50% aqueous dioxane. The mixture was heated at 150° C. for 5 min. with microwave irradiation. The mixture was filtered and the volatiles were removed in vacuo. The residue was partitioned between ethyl acetate and water, the phases were separated and the organics were dried over magnesium sulfate, filtered and concentrated. The residue was chromatographed (silica gel, elution with methanol/DCM) to give 32 mg of product. LC/MS (long run): Retention time, 6.54 min; (M+H)=432.2

Example 171

[2-Fluoro-5-(1H-indol-5-yl)-phenyl]-[2S-(4-fluoro-phenyl)-4-methyl-piperazin-1-yl]-methanone

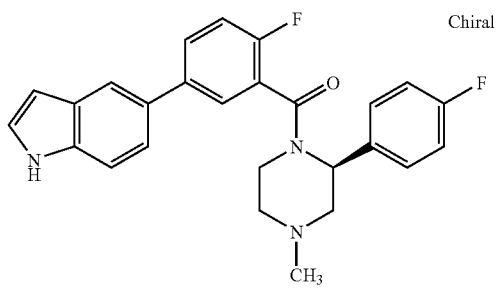

Step 1: (5-Bromo-2-fluoro-phenyl)-[(S)-2-(4-fluoro-phenyl)-piperazin-1-yl]-methanone: Diisopropylamine (0.47 g, 3.7 mmol) and HATU (0.69 g, 1.8 mmol) were added to a mixture of 5-bromo-2-fluorophenylcarboxylic acid 90.4 g, 1.8 mmol) and (S)-3-(4-fluoro-phenyl)-piperazine-1-carboxylic acid tert-butyl ester (0.34 g, 1.8 mmol) in 50 mL of dimethylformamide. The mixture was stirred at ambient temperature for 15 h. The volatiles were removed in vacuo, and the residue was partitioned between ethyl acetate and 1M sodium bicarbonate solution. The organic phase was washed with water, dried over magnesium sulfate, filtered and concentrated to leave 0.46 g of product. This material was dissolved in 4.5 mL of dichloromethane and added to 10 mL of 95% trifluoroacetic acid/water. This mixture was stirred at room temperature for 1.5 h and then the volatiles were removed in vacuo. The residue was purified by chromatography on silica gel (elution with 3% ethanol/dichloromethane) to give 0.32 g of product. LC/MS: Retention time, 2.08 min; (M+H)=381/383

Step 2: (5-Bromo-2-fluoro-phenyl)-[(S)-2-(4-fluoro-phenyl)-4-methyl-piperazin-1-yl]-methanone: Formaldehyde (1.47 mL, 19.4 mmol of 37% aqueous solution) was added to (5-Bromo-2-fluoro-phenyl)-[(S)-2-(4-fluoro-phenyl)-piperazin-1-yl]-methanone (0.32 g, 0.65 mmol) in 10 mL of methanol. The mixture was stirred at ambient temperature for 1 h and then sodium triacetoxyborohydride (0.82 g, 3.9 mmol) was added and the resulting mixture was stirred overnight. The volatiles were removed in vacuo, and the residue was portioned between ethyl acetate and 1M sodium bicarbonate solution. The organic phase was washed with 1M sodium bicarbonate solution and brine, dried over magnesium sulfate, filtered and concentrated to leave 0.21 g of product. LC/MS: Retention time, 2.14 min; (M+H)=395/397.

Step 3 [2-Fluoro-5-(1H-indol-5-yl)-phenyl]-[2S-(4-fluoro-phenyl)-4-methyl-piperazin-1-yl]-methanone: A mixture of (5-bromo-2-fluoro-phenyl)-[(S)-2-(4-fluoro-phenyl)-4-methyl-piperazin-1-yl]-methanone (0.2 g, 0.51 mmol) indole-5-boronic acid (0.086 g, 0.53 mmol), cesium carbonate in water (2M, 1.01 mL, 2.0 mmol) in 10 mL of dioxane was degassed (evacuate in vacuo and pressurize with nitrogen, 3 times). PdCl$_2$(dppf).DCM (0.037 g, 0.0513 mmol) was added and the mixture was heated at 110-110° C. for 1.5 h. The volatiles were removed in vacuo, and the residue was partitioned between ethyl acetate and water. The organic phase was washed with water, dried over MgSO$_4$, filtered and evaporated to give a dark brown syrup. Chromatography on silica gel, eluting with 2% ethanol/DCM gave 74 mg of the product. LC/MS (long run): Retention time, 5.24 min; (M+H)=432

Example 172

4-Fluoro-N-[2-fluoro-5-(1H-pyrrolo[2,3-c]pyridin-5-yl)-benzyl]-N-(2-pyrrolidin-1-yl-ethyl)-benzamide

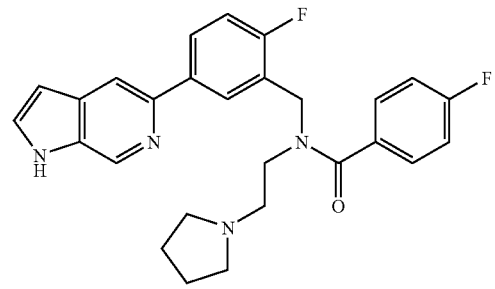

Step 1: N-{5-[4-((E)-2-Dimethylamino-vinyl)-5-nitro-pyridin-2-yl]-2-fluoro-benzyl}-4-fluoro-N-(2-pyrrolidin-1-yl-ethyl)-benzamide: 4-Fluoro-N-[2-fluoro-5-(4-methyl-5-nitro-pyridin-2-yl)-benzyl]-N-(2-pyrrolidin-1-yl-ethyl)-benzamide (prepared according to example 20, 600 mg, 1.25 mmol) in 15 mL of dimethylformamide was treated with dimethylformamide dimethyl acetal (0.23 mL, 1.68 mmol), and the resulting mixture was heated at 80° C. for 5 h. The mixture was allowed to cool and the volatiles were removed. The residue was partitioned between ethyl acetate and water. The organic phase was washed with water, dried over MgSO$_4$, filtered and evaporated to give an oil. The above process was repeated to give 485 mg of product.

Step 2: 4-Fluoro-N-[2-fluoro-5-(1H-pyrrolo[2,3-c]pyridin-5-yl)-benzyl]-N-(2-pyrrolidin-1-yl-ethyl)-benzamide: N-{5-[4-((E)-2-Dimethylamino-vinyl)-5-nitro-pyridin-2-yl]-2-fluoro-benzyl}-4-fluoro-N-(2-pyrrolidin-1-yl-ethyl)-benzamide (485 mg, 0.9 mmol) in 30 mL of ethyl acetate was treated with 100 mg of 10% Pd/C under 3 bar of hydrogen for 18 h. The mixture was filtered through celite and the filtrate was concentrated in vacuo. The residue was chromatographed (alumina, elution with 2% methanol/dichloromethane) to afford 230 mg of product. LC/MS: Retention time, 1.79 min; (M+H)=461. $^1$H NMR (400 MHz, DMSO-D$_6$) δ ppm: 1.61 (br s, 4H) 2.37 (br ss, 2H) 2.56-2.71 (br s, 2H) 3.45 (t, J=6.26 Hz, 2H) 4.75 (s, 2H) 6.55 (s, 1H) 7.17-7.28 (m, 3H) 7.45-7.52 (m, 2H) 7.56 (t, J=2.64 Hz, 1H) 8.00 (ddd, J=8.30, 5.44, 2.31 Hz, 2H) 8.07 (d, J=7.47 Hz, 1H) 8.82 (s, 1H) 11.40 (s, 1H).

Example 173

5-{6-[2S-(4-Fluoro-phenyl)-4-methyl-piperazin-1-ylmethyl]-pyrazin-2-yl}-1H-indole acetate

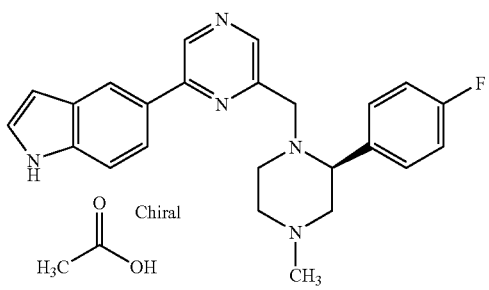

Step 1: 6-Chloro-pyrazine-2-carboxylic acid ethyl ester: Ethyl pyrazine carboxylate (4.0 g, 13.14 mmol) in 200 mL of DCM was treated at 0° C. with meta-chloroperbenzoic acid (57-80%, 5.67 g). The mixture was allowed to warm to ambient temperature and stirred for 72 h, when an additional 4.28 g of meta-chloroperbenzoic acid was added. After an additional 4 d, 6 mL of acetone was added and stored for 2.5 d. Then 2.2 g of sodium metabisulfite in 5 mL of water was added and stirred for 2 h. Ethyl acetate was added and the mixture was washed with brine, dried over sodium sulfate, filtered and concentrated to leave a solid which was purified by chromatography (silica gel, elution with ethyl acetate/pentane), affording 3.35 g of the N-oxide. The N-oxide thus prepared (2.0 g, 11.89 mmol) in 10.53 mL of phosphorous oxychloride and 18 mL of toluene was heated at 100° C. for 1.5 h. The mixture was carefully treated with ice and then with saturated aqueous sodium carbonate solution. The product was extracted into ethyl acetate, and the combined organic layers were washed with brine, dried over sodium sulfate, filtered and concentrated. The residue was purified by column chromatography (elution with ethyl acetate/pentane) to give 1.27 g of 6-chloro-pyrazine-2-carboxylic acid ethyl ester.

Step 2: 6-(1H-Indol-5-yl)-pyrazine-2-carboxylic acid ethyl ester: 6-Chloro-pyrazine-2-carboxylic acid ethyl ester (1.35 g, 7.23 mmol) was added to indole-5-boronic acid (1.16 g, 7.23 mmol), cesium carbonate (9.43 g, 28.9 mmol) and PdCl$_2$(dppf).DCM (591 mg, 0.72 mmol) in 30 mL of dioxane. The mixture was degassed (evacuate in vacuo and pressurize with nitrogen), 14.5 mL of water was added and the mixture degassed. The mixture was heated at 85° C. for 2.5 h. and the mixture was allowed to cool and the layers were separated. The aqueous phase was extracted with chloroform and the combined organic layers were washed with brine, dried over sodium sulfate, filtered and evaporated. Chromatography of the residue on silica gel, eluting with ethyl acetate/pentane afforded 1.07 g of product. LC/MS: Retention time, 3.21 min; (M+H)=268.1.

Step 3: 6-(1H-Indol-5-yl)-pyrazin-2-yl methanol: A chilled solution of 6-(1H-indol-5-yl)-pyrazine-2-carboxylic acid ethyl ester (1.07 g, 4.0 mmol) in 20 mL of THF was added to a solution of lithium aluminum hydride (243 mg, 6.4 mmol) in 20 mL of THF at −78° C. The mixture was stirred at −78° C. for 45 min, and then it was warmed to 0° C. and stirred for a further 45 min, and finally it was stirred at room temperature for 1.5 h. 0.25 mL of water and 0.25 mL of 15% sodium hydroxide solution followed by an additional 0.75 mL of water was added, the mixture was filtered through celite and the filter cake was washed with DCM. The filtrate was concentrated and the residue dissolved in chloroform, washed with water and brine, dried over sodium sulfate, filtered and concentrated in vacuo. The residue was recrystallized from hot ethyl acetate to give 486 mg of a solid. Chromatography (silica gel, elution with methanol/DCM) afforded 308 mg of 6-(1H-indol-5-yl)-pyrazin-2-yl methanol.

Step 4: 5-{6-[2S-(4-Fluoro-phenyl)-4-methyl-piperazin-1-ylmethyl]-pyrazin-2-yl}-1H-indole acetate: Methanesulfonic anhydride (226 mg, 1.3 mmol) was added to 6-(1H-indol-5-yl)-pyrazin-2-yl methanol (146 mg, 0.65 mmol) in THF. Triethylamine (0.27 mL, 1.94 mmol) was added and the mixture allowed to stir at ambient temperature for 45 min. at which time (S)-3-(4-fluoro-phenyl)-1-methyl-piperazine (315 mg, 1.62 mmol) was added and the mixture was stirred for an additional 18 h, when the volatiles were removed in vacuo and combined with the product from an additional reaction performed with 140 mg of the alcohol. This was diluted with DCM, and the organic phase was washed with water and brine, dried over sodium sulfate, filtered and concentrated. The residue was purified by column chromatography on silica gel (elution with DCM/methanol/acetic acid/water) to provide 110 mg of the title compound. LC/MS (long run): Retention time, 2.34 min; (M+H)=402.

$^1$H NMR (400 MHz, methanol-D$_4$) δ ppm: 1.97 (s, 3H) 2.51 (s, 3H) 2.57 (t, J=11.7 Hz, 1H) 2.66-2.74 (m, 2H) 3.04 (dd, J=11.65, 2.42 Hz, 1H) 3.10-3.17 (m, 2H) 3.43 (d, J=14.6 Hz, 1H) 3.69 (dd, J=10.88, 2.97 Hz, 1H) 3.88 (d, J=14.6 Hz, 1H) 6.57 (m, 1H) 7.12 (t, J=8.79 Hz, 2H) 7.31 (d, J=3.08 Hz, 1H) 7.50 (d, J=8.57 Hz, 1H) 7.55 (dd, J=8.46, 5.39 Hz, 2H) 7.82 (dd, J=8.57, 1.76 Hz, 1H) 8.28 (d, J=1.32 Hz, 1H) 8.34 (s, 1H) 8.93 (s, 1H).

Example 174

5-{4-Fluoro-3-[2S-(4-fluoro-phenyl)-piperazin-1-ylmethyl]-phenyl}-1H-indole acetate

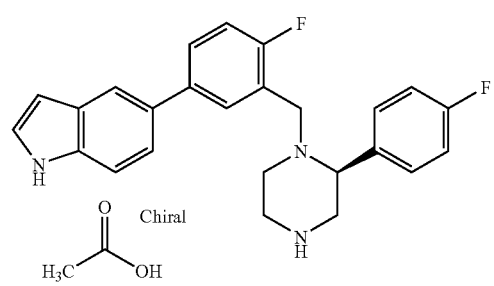

The title compound was prepared by the methods of example 91, without the methylation in step 3. LC/MS (long run): Retention time, 5.76 min; (M+H)=404.

Example 175

5-{4-Fluoro-3-[2S-(4-fluoro-phenyl)-4-methyl-piperazin-1-ylmethyl]-phenyl}-1H-indole-3-carbonitrile

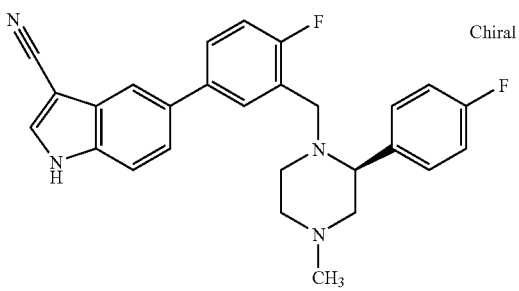

A mixture of 5-{4-fluoro-3-[2S-(4-fluoro-phenyl)-piperazin-1-ylmethyl]-phenyl}-1H-indole-3-carbonitrile (prepared according to the methods in example 113, 79 mg, 0.18 mmol), formaldehyde (37% aq. solution, 0.13 mL), acetic acid (0.011 mL, 0.18 mmol) in 2.5 mL of methanol was treated with sodium triacetoxyborohydride (214 mg, 1.01 mmol) overnight. The volatiles were removed in vacuo and saturated sodium bicarbonate solution was added. The product was extracted into DCM and the combined organics were washed with water, dried over sodium sulfate, filtered and concentrated. Chromatography (reverse phase preparative HPLC, elution with acetonitrile/water provided 52 mg of product. LC/MS (long run): Retention time, 5.96 min; (M+H)=443.

Biological Examples

Example 176

Receptor Binding Assay

Cell Culture: BHK cells stably expressing the human $5HT_{2A}$ receptor were maintained in Dulbecco's Modified Eagle's Medium supplemented with 0.4/ml Geneticin, 1% Sodium Pyruvate, 1% Pen-Strep and 10% Fetal Calf Serum, and treated with 5 mM sodium butyrate for 24 h to increase receptor expression before harvesting. Cells were harvested by mechanical scraping, washed with Phosphate Buffered Saline, and stored at −80° C. in 10% DMSO in 1 mg/mil aliquots until used. Protein determination was made according to Lowry.

Membranes from cell lines expressing the human dopamine $D_{2L}$, and α-adrenergic$_{1A}$ ((α1A) receptors were prepared as previously described (Kongsamut et al., 1996 and Brooks et al., 1999). Membranes from cell lines expressing the human $5HT_{2C}$ receptor were obtained from Packard Bioscience.

Receptor Binding Assays: The $5HT_{2A}$ and $D_{2L}$ assays were conducted at 37° C. in a Tris buffer containing salts (50 mM Tris Buffer, pH 7.7; 120 mM NaCl; 5 mM KCl; 2 mM $CaCl_2$; 1 mM $MgCl_2$). Cell membranes (previously prepared and frozen) were rapidly thawed. Membranes were diluted to an appropriate concentration (to produce 100 μg protein/assay point for $5HT_{2A}$, and 58 μg protein/assay point for $D_{2L}$) in Tris buffer and homogenized. Assays were conducted on 96-well plates, using 2.5 and 1 nM [$^3$H]N-methyl spiperone as radioligand for $5HT_{2A}$ and $D_{2L}$ assays, respectively. Plates were incubated at 37° C. in a shaking water bath for 30 and 60 min, for $5HT_{2A}$ and $D_{2L}$, respectively. Nonspecific binding was defined using 100 μM methylsergide and eticlopride, for $5HT_{2A}$ and $D_{2L}$, respectively.

The $5HT_{2C}$ assay was conducted at 37° C. in a Tris buffer (50 mM Tris, 4 mM $CaCl_2$ and 1% ascorbate, pH 7.4). Cell membranes (purchased from Packard Bioscience) were rapidly thawed. Membranes were diluted to an appropriate concentration (to produce 1 unit protein/assay point) in Tris buffer and homogenized. Assays were conducted on 96-well plates, using 5 nM [$^3$H]mesulergine as radioligand. Plates were incubated at 37° C. in a shaking water bath for 60 min. Nonspecific binding was defined using 100 μM mianserin.

The $α_{1A}$ assay was conducted at 37° C. in a Tris buffer (50 mM Tris HCL, pH 7.7 containing 0.1% Ascorbic acid). Cell membranes (previously prepared and frozen) were rapidly thawed. Membranes were diluted to an appropriate concentration (to produce 130 μg protein/assay point) in Tris buffer and homogenized. Assays were conducted on 96-well plates, using 1 nM [$^3$H]prazosin as radioligand. Plates were incubated at 37° C. in a shaking water bath for 60 min. Nonspecific binding was defined using 100 μM phentolamine.

Assays were terminated by rapid filtration through Millipore MAFB or MAFC ($5HT_{2C}$) filter plates (presoaked in 50 mM Tris HCl, pH 7.7, with 0.1% Brij) using a Millipore Cell Harvester. The filter plates were then washed with ice-cold 50 mM Tris buffer, pH 7.7, and allowed to dry overnight. 50 μl of Microscint scintillation cocktail were added and the plates were counted in a Packard Topcount scintillation counter.

$IC_{50}$ and $K_i$ calculations were performed using nonlinear regression one-site competition analysis (GraphPad, Prism), with top and bottom limits held constant at 0% and 100% inhibition, respectively. The percent inhibition at each drug concentration was the average of duplicate determinations. Except where indicated, each determination was performed 2 to 5 times.

5-$HT_{2A}$ Functional Assay: BHK cells were maintained as described above, and seeded overnight in 96 well collagen coated plates (black-wall, clear bottom) at a density of 45000/75 μl of medium in 0.5% serum. The following day, the calcium dye kit (Molecular Probes) was prepared in Hank's Balanced Salt Solution with the addition of 5 mM probenecid (pH 7.4), and cells were incubated with this solution for 1 hour at 37° C. Compounds were prepared as a 10 mM DMSO stock and diluted from there; the agonist (serotonin) were prepared fresh daily.

Dye loaded cells were excited at 488 nm and the emission detected at 525 nm using a 515 nm cut-off filter and a high photomultiplier setting on a Molecular Devices FLEXstation™. Wells were read (1 column at a time) at 2 second intervals for a total period of 375 seconds. Compound or vehicle were added at 15 seconds followed by the addition of 5-HT (1 μM final) at 315 seconds (5 min pretreatment), or compound was added during dye loading (60 min pretreatment).

The signal was calculated by subtracting the peak response from the mean of the baseline fluorescence. The percentage of the maximum response to 1 μM 5-HT was then calculated in order to generate $IC_{50}$ curves.

REFERENCES

Brooks K. M., Cai J., Sandrasagra A., Roehr J. E., Errazo R., Vargas H. M.; Interaction of clozapine and other antipsychotic drugs with human alpha 1-adrenergic receptor subtypes, Proc. West Pharmacol. Soc. 1999; 42:67-69.

Kongsamut S., Roehr J. E., Cai J., Hartman H. B., Weissensee P., Kerman L. L., Tang L., Sandrasagra A.; Iloperidone binding to human and rat dopamine and 5-HT receptors, Eur. J. Pharmacol. 1996; 317(2-3):417-423.

The observed $K_i$ values (expressed in nanomolar concentration, nM) at the receptor site $5HT_{2A}$ for the compounds of this invention are tabulated in Table 17.

TABLE 17

| Example No. | $5\text{-}HT_{2A}\ K_i$ (nM) |
| --- | --- |
| 1 | 10.8 |
| 2 | 2.4 |
| 3 | 0.9 |
| 4 | 33.5 |
| 5 | 217.6 |
| 6 | 2.7 |
| 7 | 210.0 |
| 8 | 35.4 |
| 9 | 227.0 |
| 10 | 13.8 |
| 11 | 16.2 |
| 13 | 3.3 |
| 14 | 1.4 |
| 15 | 13.8 |
| 16 | 4.9 |
| 17 | 7.2 |
| 18 | 74.8 |
| 19 | 76.5 |
| 20 | 0.32 |
| 21 | 0.26 |
| 23 | 0.37 |
| 24 | 0.56 |
| 25 | 0.6 |
| 26 | 0.68 |
| 27 | 0.7 |
| 28 | 0.7 |
| 29 | 0.7 |
| 30 | 0.77 |
| 31 | 0.92 |
| 32 | 1.1 |
| 33 | 1.19 |
| 34 | 1.25 |
| 35 | 2.8 |
| 36 | 4.1 |
| 37 | 4.1 |
| 38 | 14.4 |
| 39 | 1.1 |
| 40 | 0.58 |
| 42 | 0.61 |
| 43 | 0.6 |
| 45 | 0.99 |
| 47 | 1.24 |
| 48 | 0.6 |
| 49 | 0.4 |
| 50 | 2.5 |
| 51 | 9.2 |
| 52 | 3.1 |
| 53 | 2.13 |
| 54 | 0.9 |
| 55 | 0.31 |
| 56 | 6.51 |
| 57 | 0.71 |
| 58 | 1.23 |
| 59 | 0.89 |
| 60 | 1.13 |
| 61 | 0.7 |
| 62 | 0.75 |
| 63 | 0.58 |
| 64 | 0.6 |
| 65 | 0.9 |
| 66 | 0.67 |
| 67 | 2.16 |
| 68 | 3.14 |
| 69 | 1.35 |
| 70 | 0.72 |
| 71 | 0.49 |
| 72 | 2.37 |
| 74 | 1.05 |
| 75 | 2.14 |
| 76 | 4.74 |
| 77 | 0.49 |
| 78 | 0.76 |
| 79 | 0.61 |
| 80 | 14.9 |
| 81 | 2.0 |
| 82 | 0.51 |
| 83 | 0.82 |
| 84 | 0.37 |
| 85 | 0.42 |
| 86 | 1.68 |
| 87 | 14.2 |
| 88 | 1.16 |
| 89 | 1.0 |
| 90 | 0.42 |
| 91 | 0.6 |
| 93 | 0.6 |
| 95 | 1.9 |
| 96 | 0.89 |
| 97 | 0.77 |
| 98 | 1.2 |
| 99 | 0.29 |
| 100 | 0.6 |
| 101 | 0.39 |
| 102 | 0.88 |
| 103 | 1.01 |
| 104 | 0.31 |
| 105 | 3.8 |
| 106 | 9.0 |
| 107 | 85.0 |
| 108 | 16.0 |
| 110 | 85.0 |
| 111 | 85.0 |
| 112 | 6.0 |
| 113 | 0.4 |
| 114 | 0.48 |
| 115 | 2.88 |
| 116 | 1.79 |
| 117 | 4.79 |
| 118 | 1.1 |
| 119 | 0.78 |
| 120 | 65.0 |
| 121 | 82.0 |
| 140 | 22.6 |
| 171 | 85.0 |
| 174 | 0.9 |
| 175 | 3.2 |

Example 177

Head Twitch Assay

This Example 177 illustrates the study of efficacy of the compounds of this invention at the $5HT_{2A}$ receptor site in animal models. In this Example 177, the inhibition of dimethyltryptamine (DMT) induced head twitch in the mouse was measured using the compound of this invention as set forth below.

5-MeODMT (5-Methoxy-N,N-dimethyltryptamine) Inhibition: Groups of male mice are administered test compounds at selected doses. At an appropriate interval thereafter, 5-MeODMT (dissolved in 0.5% ascorbic acid) is administered at a dose of 30 mg/kg i.p. Immediately after administration of 5-MeODMT, and continuing for the following 6 min, the number of head twitches for each animal is counted. For inhibitory effects, animals exhibiting no head twitches during 6 min period are considered blocked. The $ED_{50}$ is calculated as the dose necessary to block head twitch in 50% of the test animals. All experiments are performed with at least 10 animals per condition.

The observed ED$_{50}$ values (expressed as mg/kg) for the compounds of this invention are tabulated in Table 18.

TABLE 18

| Example No. | ED$_{50}$ mg/kg, sc |
|---|---|
| 3 | <1 (100% effect @ 1 mg/kg) |
| 20 | 0.27 |
| 21 | <3 (60% effect @ 3 mg/kg) |
| 23 | 0.16 |
| 26 | 0.82 |
| 27 | 0.59 |
| 34 | 1.09 |
| 42 | 1.73 |
| 44 | 0.54 |
| 47 | ~3 (50% effect @ 3 mg/kg) |
| 91 | 0.41 |
| 92 | 0.53 |
| 94 | ~3 (50% effect @ 3 mg/kg) |
| 95 | 0.5 |
| 98 | 0.49 |
| 104 | 6.36 |
| 133 | 0.92 |
| 159 | 0.04 |
| 161 | 0.16 |

Example 178

Sleep Maintenance Insomnia Studies

This Example 178 illustrates the study of efficacy of the compounds of this invention in improving the sleep quality in animal models.

To record cortical electro-encephalogram (EEG), male Sprague-Dawley rats are fitted with four miniature screw electrodes placed through the skull (1.5 mm either side of the central suture, 1.5, 3.0, 4.5 and 6.0 mm anterior to lambda) and allowed to recover for 7 days. Freely moving animals are then placed (in their own home cage) in a soundproof, temperature and humidity-controlled recording room. For each rat, recordings are made from the two leads providing the largest theta rhythm amplitude. Theta rhythm (5-9 Hz) and slower electrical activities (0-4 Hz) are recorded in waking animals (W). Only slow waves (0-4 Hz) and sleep spindles (12-14 Hz) are observed during slow wave sleep (SWS). Theta rhythm alone is recorded during paradoxical sleep (PS). For each rat and each vigilance level (W, SWS, PS), a minimum of 90 averaged power spectra, corresponding to visually identified episodes, are summed in order to obtain an averaged reference spectrum. The effects of the compounds of this invention on each of these rhythms are measured.

The compounds of this invention are administered either 5 hours after lights on or 18 hours after lights-on. Six animals are included in each treatment group. All of the compounds of this invention are administered intraperitoneally. A vehicle control and positive reference compound are included in each study. A satellite group of animals are dosed to examine pharmacokinetics; blood, from which, plasma fractions are obtained, and brain samples are collected from these animals.

Example 179

Obstructive Sleep Apnea Studies

Intraperitoneal application of L-tryptophan (10 mg/kg) and pargyline (50 mg/kg) to anaesthetized newborn rats depresses the amplitude of the inspiratory discharges of the genioglossal muscle and induces obstructive apneas (OA). The following procedure describes how to determine the efficacy of the compounds of this invention when compared with the efficacy of theophylline.

Experiments are carried out on newborn Sprague Dawley rats. The animals are anaesthetized by intraperitoneal injection of low doses of sodium pentobarbitone (7-10 mg/kg), kept lying (dorsal cubitus) on a warming blanket and are spontaneously ventilating.

The electromyogram (EMG) activity of the genioglossal muscles and the diaphragm are recorded with fine insulated wires (bipolar recordings) inserted within the muscles, filtered (100-3,000 Hz), amplified (×5-10,000) and integrated (time constant 50 ms). The rib cage movements are recorded via a captor gently touching the lower ribs and/or the abdominal wall. The air flow changes resulting from the respiratory chest movements are recorded via a facial mask and a highly sensitive pressure recorder.

Effects of a compound of this invention on depression of genioglossal EMG induced by 1-tryptophan and pargyline can be measured as follows: Ten to fifteen minutes after induction of anesthesia, the animals receive first an intraperitoneal injection of a compound of this invention, and a control recording is taken to define the mean amplitude of the integrated EMGs. Then, the animal receives an intraperitoneal injection of L-tryptophan plus pargyline ("L-Trp+Parg") 10 mg/kg and 50 mg/kg, respectively, and the changes in EMG amplitudes are checked every 10 minutes and are expressed as percent (%) of control values.

In general, the pre-treatment with a compound of this invention at dosage levels of about 0.1 mg/kg to about 1.0 mg/kg can prevent the depression of genioglossal (GG) discharge induced by injection of L-Trp+Parg.

Effects of the compound pretreatment on the occurrence of obstructive apnea (OAs) induced by 1-tryptophan and pargyline injection can be measured as follows: The respiratory movements and resulting air flow changes are measured in 30 newborn rats which receive first a pre-treatment with a compound of this invention at either 0.1, 1 or 3 mg/kg and 10 min later L-Trp+Parg injection. Generally, L-Trp+Parg injection induces OAs in newborn rats. The rats which receives the compound of this invention are expected to display short lasting OAs to no OAs depending on the dosage administered. For instance, the rats receiving 0.1 mg/kg to 1 mg/kg of the compound of this invention may exhibit short lasting OAs. Whereas the rats receiving higher dosages of about 3 mg/kg are expected show no OAs.

Effects of theophylline pre-treatment on the occurrence of obstructive apneas induced by 1-tryptophan and pargyline injection are measured as follows: Five newborn rats receive theophylline at 10 mg/kg and 5 other animals receive theophylline at 30 mg/kg. In both cases, L-Trp+Prg injection depresses the amplitude of GG inspiratory discharges and this effect is not prevented by either dose of theophylline. In a second set of experiments, induction of OAs after L-Trp+Prg injection also is not prevented by theophylline at 10 or 30 mg/kg.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound, including enantiomers, stereoisomers, and tautomers of said compound and pharmaceutically acceptable salts thereof, with said compound having the general structure shown in formula I:

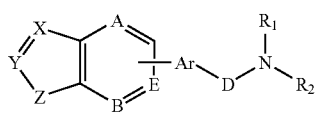

wherein:

$X = Y$ denotes a single bond between X and Y;
X is O or S;
Y is CHR or CO;
Z is NR;
A, B and E are the same or different and independently from each other are CR;
D is either $CH_2$ or CO;
Ar is selected from the group consisting of substituted or unsubstituted phenyl, pyridinyl, pyrazinyl, furanyl and thiophenyl wherein the substituents are selected from the group consisting of fluorine, chlorine, $C_{1-4}$ alkyl, $C_{1-4}$ alkoxy and $-CF_3$;
each R is independently chosen from hydrogen, halogen, CN, $C(O)NR_3R_4$, $C_{1-4}$alkyl, $C_{1-4}$alkoxy, $C_{1-4}$alkenyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1; wherein
$R_3$ and $R_4$ are hydrogen or $C_1$alkyl; and
$R_1$ and $R_2$ taken together with the nitrogen atom to which they are attached form an unsubstituted or at least mono-substituted piperazine or diazepane; and wherein the substituents are selected from the group consisting of phenyl, fluorophenyl, trifluoromethylphenyl, pyridinyl, thiophenyl, furanyl $C_{3-8}$cycloalkyl, $C_{1-4}$alkyl, $C_{1-4}$alkoxy, $C_{1-4}$alkenyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, $-NO_2$, $-NH_2$, $-NH(C_{1-4}alkyl)$, $-N(C_{1-4}alkyl)_2$, $-CN$, $-C(O)R_5$, $-NHC(O)(C_{1-4}alkyl)$, $-SO_2Cl$, $-SO_2(C_{1-4}alkyl)$, halogen and hydroxy; wherein
$R_5$ is hydroxy, $C_{1-3}$alkoxy, $-O$-phenyl, $-NH_2$, $-NH(C_{1-3}alkyl)$, $-N(C_{1-3}alkyl)_2$ or phenyl.

2. The compound as set forth in claim 1, wherein:
D is $CH_2$;
Ar is substituted or unsubstituted phenyl, pyridinyl, pyrazinyl, furanyl or thiophenyl; wherein the substituents are selected from the group consisting of fluorine, chlorine, $C_{1-4}$alkyl, $C_{1-4}$alkoxy and $-CF_3$;
each R is independently chosen from hydrogen, CN or $C_{1-4}$alkyl; and
$R_1$ and $R_2$ taken together with the nitrogen atom to which they are attached form a unsubstituted or at least mono-substituted piperazine or diazepane; wherein the substituents are selected from the group consisting of phenyl, fluorophenyl, trifluoromethylphenyl, pyridinyl, thiophenyl, furanyl and $C_{1-4}$alkyl.

3. The compound as set forth in claim 2, wherein:

$X = Y$ denotes a single bond between X and Y;
X is O or S;
Y is CO;
Z is NR;
A, B and E are CH;
Ar is phenyl, fluorophenyl, chlorophenyl, pyridinyl, pyrazinyl, furanyl or thiophenyl;
each R is independently chosen from hydrogen, methyl or ethyl;
$R_1$ and $R_2$ taken together with the nitrogen atom to which they are attached form a unsubstituted or at least mono-substituted piperazine or diazepane; wherein the substituents are selected from the group consisting of phenyl, fluorophenyl, trifluoromethylphenyl, pyridinyl, thiophenyl, furanyl and methyl.

4. The compound as set forth in claim 3 selected from the group consisting of:
6-[3-(4-methyl-piperazin-1-ylmethyl)-phenyl]-3H-benzooxazol-2-one;
6-{5-[2R-(4-fluoro-phenyl)-4-methyl-piperazin-1-ylmethyl]-furan-3-yl}-3H-benzooxazol-2-one;
6-{5-[2S-(4-fluoro-phenyl)-4-methyl-piperazin-1-ylmethyl]-furan-2-yl}-3H-benzooxazol-2-one;
6-{5-[2S-(4-fluoro-phenyl)-4-methyl-piperazin-1-ylmethyl]-thiophen-3-yl}-3H-benzooxazol-2-one;
6-[4-fluoro-3-(2-thiophen-2-yl-piperazin-1-ylmethyl)-phenyl]-3H-benzooxazol-2-one;
6-{5-[2S-(4-fluorophenyl)-4-methylpiperazine-1-ylmethyl]-furan-3-yl}-3H-benzoxazol-2-one;
6-{5-[2S-(4-fluoro-phenyl)-piperazin-1-ylmethyl]-furan-3-yl}-3H-benzooxazol-2-one acetate;
6-{4-fluoro-3-[2S-(4-fluoro-phenyl)-4-methyl-piperazin-1-ylmethyl]-phenyl}-3H-benzooxazol-2-one; and
6-{5-[2S-(4-fluoro-phenyl)-4-methyl-piperazin-1-ylmethyl]-pyridin-3-yl}-3H -benzooxazol-2-one acetate;
or a pharmaceutically acceptable salt thereof or an optical or stereoisomer thereof.

5. A pharmaceutical composition comprising one or more compounds of formula I, including enantiomers, stereoisomers, and tautomers of said compound and pharmaceutically acceptable salts thereof, in combination with one or more pharmaceutically acceptable carriers, diluents or excipients:

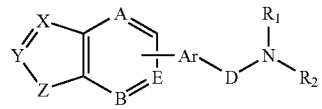

wherein:

$X = Y$ denotes a single bond between X and Y;
X is O or S;
Y is CHR or CO;
Z is NR;

A, B and E are the same or different and independently from each other are CR;

D is either CH$_2$ or CO;

Ar is selected from the group consisting of substituted or unsubstituted phenyl, pyridinyl, pyrazinyl, furanyl and thiophenyl wherein the substituents are selected from the group consisting of fluorine, chlorine, C$_{1-4}$ alkyl, C$_{1-4}$ alkoxy and —CF$_3$;

each R is independently chosen from hydrogen, halogen, CN, C(O)NR$_3$R$_4$, C$_{1-4}$alkyl, C$_{1-4}$alkoxy, C$_{1-4}$alkenyl, fluoroalkyl or fluoroalkoxy of the formula C$_n$H$_x$F$_y$ or OC$_n$H$_x$F$_y$, wherein n is an integer from 1 to 4, x is an integer from 0 to 8, y is an integer from 1 to 9 and sum of x and y is 2n+1; wherein R$_3$ and R$_4$ are hydrogen or C$_{1-4}$alkyl;

R$_1$ and R$_2$ taken together with the nitrogen atom to which they are attached form an unsubstituted or at least mono-substituted piperazine or diazepane; and wherein the substituents are selected from the group consisting of phenyl, fluorophenyl, trifluoromethylphenyl, pyridinyl, thiophenyl, furanyl C$_{3-8}$cycloalkyl, C$_{1-4}$alkyl, C$_{1-4}$alkoxy, C$_{1-4}$alkenyl, fluoroalkyl or fluoroalkoxy of the formula C$_n$H$_x$F$_y$ or OC$_n$H$_y$F$_y$, wherein n is an integer from 1 to 4, x is an integer from 0 to 8, y is an integer from 1 to 9 and sum of x and y is 2n+1, —NO$_2$, —NH$_2$, —NH(C$_{1-4}$alkyl), —N(C$_{1-4}$alkyl)$_2$, —CN, —C(O)R$_5$, —NHC(O)(C$_{1-4}$alkyl), —SO$_2$Cl, —SO$_2$(C$_{1-4}$alkyl), halogen and hydroxy; wherein R$_5$ is hydroxy, C$_{1-3}$alkoxy, —O-phenyl, —NH$_2$, —NH(C$_{1-3}$alkyl), —N(C$_{1-3}$alkyl)$_2$ or phenyl.

6. The composition as set forth in claim 5, wherein the compound of formula (I) is having:

D is CH$_2$;

Ar is substituted or unsubstituted phenyl, pyridinyl, pyrazinyl, furanyl or thiophenyl; wherein the substituents are selected from the group consisting of fluorine, chlorine, C$_{1-4}$alkyl, C$_{1-4}$alkoxy and —CF$_3$;

each R is independently chosen from hydrogen, CN or C$_{1-4}$alkyl; and

R$_1$ and R$_2$ taken together with the nitrogen atom to which they are attached form a unsubstituted or at least mono-substituted piperazine or diazepane; wherein the substituents are selected from the group consisting of phenyl, fluorophenyl, trifluoromethylphenyl, pyridinyl, thiophenyl, furanyl and C$_{1-4}$ alkyl.

7. The composition as set forth in claim 5, wherein the compound of formula (I) is selected from the group consisting of:

6-[3-(4-methyl-piperazin-1-ylmethyl)-phenyl]-3H-benzooxazol-2-one;

6-{5-[2R-(4-fluoro-phenyl)-4-methyl-piperazin-1-ylmethyl]-furan-3-yl}-3H-benzooxazol-2-one;

6-{5-[2S-(4-fluoro-phenyl)-4-methyl-piperazin-1-ylmethyl]-furan-2-yl}-3H-benzooxazol-2-one;

6-{5-[2S-(4-fluoro-phenyl)-4-methyl-piperazin-1-ylmethyl]-thiophen-3-yl}-3H-benzooxazol-2-one;

6-[4-fluoro-3-(2-thiophen-2-yl-piperazin-1-ylmethyl)-phenyl]-3H-benzooxazol-2-one;

6-{5-[2S-(4-fluorophenyl)-4-methylpiperazine-1-ylmethyl]-furan-3-yl}-3H-benzooxazol-2-one;

6-{5-[2S-(4-fluoro-phenyl)-piperazin-1-ylmethyl]-furan-3-yl}-3H-benzooxazol-2-one acetate;

6-{4-fluoro-3-[2S-(4-fluoro-phenyl)-4-methyl-piperazin-1-ylmethyl]-phenyl}-3H-benzooxazol-2-one; and 6-{5-[2S-(4-fluoro-phenyl)-4-methyl-piperazin-1-ylmethyl]-pyridin-3-yl}-3H-benzooxazol-2-one acetate;

or a pharmaceutically acceptable salt thereof or an optical or stereoisomer thereof.

8. A method of treating a sleep disorder selected from the group consisting of insomnia, primary insomnia and obstructive sleep apnea in a patient comprising administering to said patient a therapeutically effective amount of a compound of formula I, including enantiomers, stereoisomers, and tautomers of said compound and pharmaceutically acceptable salts thereof, optionally in combination with one or more pharmaceutically acceptable carriers, diluents or excipients:

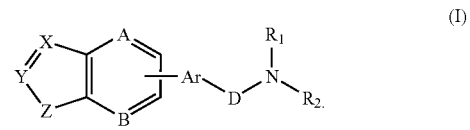

wherein:

$$X = Y$$

denotes a single bond between X and Y;

X is O or S;

Y is CHR or CO;

Z is NR;

A, B and E are the same or different and independently from each other are CR;

D is either CH$_2$ or CO;

Ar is selected from the group consisting of substituted or unsubstituted phenyl, pyridinyl, pyrazinyl, furanyl and thiophenyl wherein the substituents are selected from the group consisting of fluorine, chlorine, C$_{1-4}$ alkyl, C$_{1-4}$alkoxy and —CF$_3$;

each R is independently chosen from hydrogen, halogen, CN, C(O)NR$_3$R$_4$, C$_{1-4}$alkyl, C$_{1-4}$alkoxy, C$_{1-4}$alkenyl, fluoroalkyl or fluoroalkoxy of the formula C$_n$H$_x$F$_y$ or OC$_n$H$_x$F$_y$, wherein n is an integer from 1 to 4, x is an integer from 0 to 8, y is an integer from 1 to 9 and sum of x and y is 2n+1; wherein R$_3$ and R$_4$ are hydrogen or C$_1$alkyl; and R$_1$ and R$_2$ taken together with the nitrogen atom to which they are attached form an unsubstituted or at least mono-substituted piperazine or diazepane; and wherein the substituents are selected from the group consisting of phenyl, fluorophenyl, trifluoromethylphenyl, pyridinyl, thiophenyl, furanyl C$_{3-8}$cycloalkyl, C$_{1-4}$alkyl, C$_{1-4}$alkoxy, C$_{1-4}$alkenyl, fluoroalkyl or fluoroalkoxy of the formula C$_n$H$_x$F$_y$ or OC$_n$H$_x$F$_y$, wherein n is an integer from 1 to 4, x is an integer from 0 to 8, y is an integer from 1 to 9 and sum of x and y is 2n+1, —NO2, —NH$_2$, —NH (C$_{1-4}$alkyl), —N(C$_{1-4}$alkyl)$_2$, —CN, —C(O)R$_5$, —NHC(O)(C$_{1-4}$alkyl), —SO$_2$Cl, —SO$_2$(C$_{1-4}$alkyl), halogen and hydroxy; wherein R$_5$ is hydroxy, C$_{1-3}$alkoxy, —O-phenyl, —NH$_2$, —NH(C$_{1-3}$alkyl), —N(C$_{1-3}$alkyl)$_2$ or phenyl.

9. The method as set forth in claim 8, wherein the compound of formula (I) is having:

D is CH$_2$;

Ar is substituted or unsubstituted phenyl, pyridinyl, pyrazinyl, furanyl or thiophenyl; wherein the substituents are selected from the group consisting of fluorine, chlorine, C$_{1-4}$alkyl, C$_{1-4}$alkoxy and —CF$_3$;

each R is independently chosen from hydrogen, CN or $C_{1-4}$alkyl; and $R_1$ and $R_2$ taken together with the nitrogen atom to which they are attached form a unsubstituted or at least mono-substituted piperazine or diazepane; wherein the substituents are selected from the group consisting of phenyl, fluorophenyl, trifluoromethylphenyl, pyridinyl, thiophenyl, furanyl and $C_{1-4}$alkyl.

10. The method as set forth in claim 8, wherein the sleep disorder is insomma.

11. The method as set forth in claim 8, wherein the sleep disorder is primary insomnia.

12. The method set forth in claim 8, wherein the sleep disorder is an obstructive sleep apnea.

* * * * *

UNITED STATES PATENT AND TRADEMARK OFFICE
CERTIFICATE OF CORRECTION

PATENT NO. : 7,625,889 B2
APPLICATION NO. : 11/782923
DATED : December 1, 2009
INVENTOR(S) : Paul Robert Eastwood et al.

It is certified that error appears in the above-identified patent and that said Letters Patent is hereby corrected as shown below:

On the title page, item (75), in column 1, in "Inventors", line 2, delete "David Mark Fink" and insert -- David Marc Fink --, therefor.

In column 14, line 43, delete "benzothiazol" and insert -- benzotriazol --, therefor.

In column 27, line 52, delete "XXI" and insert -- XXIII --, therefor.

In column 33, line 38, delete "0.0011" and insert -- 0.001 --, therefor.

In column 58, line 39-40, delete "tris-acetoxyborohyduide" and insert -- tris-acetoxyborohydride --, therefor.

In column 77, line 48, delete "(1 g 6.25 mmol)," and insert -- (1 g, 6.25 mmol), --, therefor.

In column 89, line 33, delete "(M+H) 452." and insert -- (M+H) = 452. --, therefor.

In column 91, line 58, delete "stifling" and insert -- stirring --, therefor.

In column 137, line 48, delete "mg/mil" and insert -- mg/ml --, therefor.

In column 140, line 53, delete "compound" and insert -- compounds --, therefor.

In column 140, line 64, after "during" insert -- this --.

In column 143, line 36, in claim 1, delete "$C_1$alkyl;" and insert -- $C_{1-4}$alkyl; --, therefor.

In column 145, line 15, in claim 5, after "$C_{1-4}$alkyl;" insert -- and --.

Signed and Sealed this
Twenty-seventh Day of December, 2011

David J. Kappos
*Director of the United States Patent and Trademark Office*

CERTIFICATE OF CORRECTION (continued)
U.S. Pat. No. 7,625,889 B2

In column 146, line 15, in claim 8, delete " 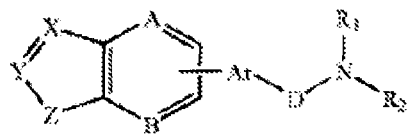 " and insert -- 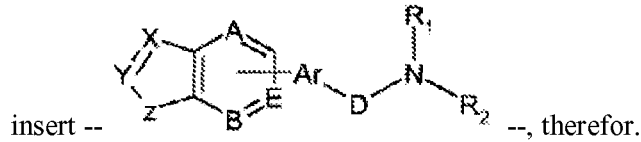 --, therefor.

In column 146, line 44, in claim 8, delete "$C_1$alkyl;" and insert -- $C_{1-4}$alkyl; --, therefor.

In column 146, line 54, in claim 8, delete "—NO2," and insert -- —$NO_2$, --, therefor.